(12) United States Patent
Badovinac-Crnjevic et al.

(10) Patent No.: US 12,252,549 B2
(45) Date of Patent: Mar. 18, 2025

(54) PERTUZUMAB PLUS TRASTUZUMAB FIXED DOSE COMBINATION

(71) Applicants: Genentech, Inc., South San Francisco, CA (US); Hoffmann-La Roche Inc., Little Falls, NJ (US)

(72) Inventors: Tanja Badovinac-Crnjevic, Basel (CH); Yu Chien Fredriksson, Basel (CH); Sarah Heeson, Welwyn Garden (GB); Ihsan Hamdi Nijem, Brisbane, CA (US); Whitney Paige Kirschbrown, San Mateo, CA (US); Eleonora Restuccia, Basel (CH)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 151 days.

(21) Appl. No.: 17/304,909

(22) Filed: Jun. 28, 2021

(65) Prior Publication Data

US 2021/0403599 A1    Dec. 30, 2021

Related U.S. Application Data

(60) Provisional application No. 63/065,795, filed on Aug. 14, 2020, provisional application No. 63/045,712, filed on Jun. 29, 2020.

(51) Int. Cl.
| | | |
|---|---|---|
| *A61P 35/00* | (2006.01) | |
| *C07K 16/32* | (2006.01) | |
| *C12N 9/26* | (2006.01) | |
| *A61K 38/00* | (2006.01) | |
| *A61K 39/00* | (2006.01) | |

(52) U.S. Cl.
CPC .............. *C07K 16/32* (2013.01); *A61P 35/00* (2018.01); *C12N 9/2474* (2013.01); *A61K 38/00* (2013.01); *A61K 2039/505* (2013.01); *C12Y 302/01035* (2013.01)

(58) Field of Classification Search
CPC ......... C07K 16/32; A61P 35/00; A61K 38/00; A61K 2039/505; C12N 9/2474
See application file for complete search history.

(56) References Cited

U.S. PATENT DOCUMENTS

| | | | |
|---|---|---|---|
| 4,968,603 A | 6/1990 | Slamon et al. | |
| 5,183,884 A | 2/1993 | Kraus et al. | |
| 5,470,954 A | 11/1995 | Neslund et al. | |
| 5,480,968 A | 2/1996 | Kraus et al. | |
| 5,641,869 A | 6/1997 | Vandlen et al. | |
| 5,648,237 A | 7/1997 | Carter | |
| 5,677,171 A | 10/1997 | Hudziak et al. | |
| 5,720,937 A | 2/1998 | Hudziak et al. | |
| 5,720,954 A | 2/1998 | Hudziak et al. | |
| 5,770,195 A | 6/1998 | Hudziak et al. | |
| 5,772,997 A | 6/1998 | Hudziak et al. | |
| 5,783,186 A | 7/1998 | Arakawa et al. | |
| 5,725,856 A | 10/1998 | Hudziak et al. | |
| 5,821,337 A | 10/1998 | Carter et al. | |
| 5,824,311 A | 10/1998 | Greene et al. | |
| 6,015,567 A | 1/2000 | Hudziak et al. | |
| 6,127,526 A | 3/2000 | Blank et al. | |
| 6,054,297 A | 4/2000 | Carter et al. | |
| 6,165,464 A | 12/2000 | Hudziak et al. | |
| 6,267,958 B1 | 7/2001 | Andya et al. | |
| 6,333,169 B1 | 12/2001 | Hudziak et al. | |
| 6,333,398 B1 | 12/2001 | Blank | |
| 6,339,142 B1 | 1/2002 | Basey et al. | |
| 6,489,447 B1 | 3/2002 | Basey et al. | |
| 6,399,063 B1 | 4/2002 | Hudziak et al. | |
| 6,387,371 B1 | 5/2002 | Hudziak et al. | |
| 6,407,213 B1 | 6/2002 | Carter et al. | |
| 6,417,335 B1 | 9/2002 | Basey et al. | |
| 6,573,043 B1 | 3/2003 | Cohen et al. | |
| 6,627,196 B1 | 9/2003 | Baughman et al. | |
| 6,632,979 B2 | 10/2003 | Erickson et al. | |
| 6,639,055 B1 | 10/2003 | Carter et al. | |
| 6,695,940 B2 | 2/2004 | Devoe et al. | |
| 6,685,940 B2 | 3/2004 | Andya et al. | |
| 6,719,971 B1 | 4/2004 | Carter et al. | |

(Continued)

FOREIGN PATENT DOCUMENTS

| | | |
|---|---|---|
| EP | 3570884 B1 | 9/2020 |
| WO | 97/04801 A1 | 2/1997 |

(Continued)

OTHER PUBLICATIONS

Diaz-Redondo et al (Different Pathological Complete Response Rates According to PAM50 Subtype in HER2+ Breast Cancer Patients Treated With Neoadjuvant Pertuzumab/Trastuzumab vs. Trastuzumab Plus Standard Chemotherapy: An Analysis of Real-World Data, Frontiers in Oncology, vol. 9, 2019, pp. 1-7) (Year: 2019).*

Agus, D., et al., "Clinical Activity in a Phase I Trial of HER-2-Targeted rhuMAb 2C4 (pertuzumab) in Patients with Advanced Solid Malignancies (AST)" Proceedings of the American Society of Clinical Oncology (Abstract No. 771), 22:192 ( 2003).

(Continued)

*Primary Examiner* — Mark Halvorson
*Assistant Examiner* — Dennis J Sullivan
(74) *Attorney, Agent, or Firm* — Wendy M. Lee

(57) ABSTRACT

The invention disclosed concerns a fixed dose combination (FDC) of pertuzumab, trastuzumab, and, optionally, recombinant human hyaluronidase (rHuPH20), which is administered subcutaneously to patients. The final efficacy and safety data for the FeDeriCa clinical trial, United States Prescribing Information (USPI) (including home-use) methods, and primary analysis of the PHranceSCa clinical trial are disclosed and claimed.

10 Claims, 25 Drawing Sheets

Specification includes a Sequence Listing.

(56) References Cited

U.S. PATENT DOCUMENTS

| | | |
|---|---|---|
| 6,800,738 B1 | 5/2004 | Carter et al. |
| 6,797,814 B2 | 9/2004 | Blank |
| 6,821,151 B2 | 11/2004 | Lai et al. |
| 6,821,515 B1 | 11/2004 | Cleland et al. |
| 6,905,830 B2 | 6/2005 | Cohen et al. |
| 6,949,245 B1 | 9/2005 | Sliwkowski et al. |
| 7,018,809 B1 | 3/2006 | Carter |
| 7,060,268 B2 | 6/2006 | Andya et al. |
| 7,097,840 B2 | 8/2006 | Erickson et al. |
| 7,041,292 B1 | 9/2006 | Sliwkowski |
| 6,984,494 B2 | 10/2006 | Ralph |
| 7,074,404 B2 | 11/2006 | Basey et al. |
| 7,279,287 B2 | 9/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 3/2009 | Adams et al. |
| 7,485,704 B2 | 3/2009 | Fahrner et al. |
| 7,498,030 B2 | 3/2009 | Adams et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,501,122 B2 | 10/2009 | Adams et al. |
| 7,618,631 B2 | 11/2009 | Sliwkowski |
| 7,531,645 B2 | 12/2009 | Basey et al. |
| 7,682,609 B2 | 3/2010 | Andya et al. |
| 7,700,299 B2 | 4/2010 | Moecks et al. |
| 7,807,799 B2 | 5/2010 | Fahrner et al. |
| 7,846,441 B1 | 7/2010 | Hellmann |
| 7,674,589 B2 | 9/2010 | Cohen et al. |
| 7,811,773 B2 | 12/2010 | Ralph |
| 7,850,966 B2 | 12/2010 | Lowman et al. |
| 7,879,325 B2 | 1/2011 | Kao et al. |
| 7,892,549 B2 | 2/2011 | Paton et al. |
| 7,862,817 B2 | 4/2011 | Adams et al. |
| 7,993,834 B2 | 9/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus et al. |
| 8,337,856 B2 | 12/2012 | Blattler et al. |
| 8,404,234 B2 | 3/2013 | Allison et al. |
| 8,597,654 B2 | 3/2013 | Bryant |
| 8,425,908 B2 | 4/2013 | Hellman |
| 8,440,402 B2 | 5/2013 | Mass |
| 8,529,901 B2 | 10/2013 | Hasmann et al. |
| 8,604,014 B2 | 10/2013 | Belvin et al. |
| 8,591,897 B2 | 11/2013 | Bryant |
| 8,592,152 B2 | 11/2013 | Mass |
| 8,372,396 B2 | 12/2013 | Andya et al. |
| 8,652,474 B2 | 2/2014 | Harris et al. |
| 8,652,479 B2 | 2/2014 | Ebens, Jr. et al. |
| 8,642,036 B2 | 4/2014 | Hellmann |
| 8,663,643 B2 | 4/2014 | Berry et al. |
| 8,710,196 B2 | 4/2014 | Emery et al. |
| 8,758,747 B2 | 6/2014 | Kallmeyer et al. |
| 8,691,232 B2 | 8/2014 | Derynck et al. |
| 8,840,896 B2 | 9/2014 | Lowman et al. |
| 9,017,671 B2 | 4/2015 | Andya et al. |
| 9,181,346 B2 | 10/2015 | Harris et al. |
| 9,345,661 B2 | 5/2016 | Adler et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,896,478 B2 | 2/2018 | Lebreton et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 7/2019 | Baughman et al. |
| 10,385,405 B2 | 8/2019 | Lee-Hoeflich et al. |
| 10,849,849 B2 | 1/2020 | Eng-Wong et al. |
| 10,689,457 B2 | 6/2020 | Paton et al. |
| 11,077,189 B2 | 8/2021 | Benyunes et al. |
| 11,638,756 B2 | 5/2023 | Benyunes et al. |
| 11,654,105 B2 | 5/2023 | Eng-Wong et al. |
| 11,655,305 B2 | 5/2023 | Paton et al. |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0064785 A1 | 5/2002 | Mass |
| 2002/0090662 A1 | 7/2002 | Ralph |
| 2003/0078388 A1 | 4/2003 | Basey et al. |
| 2003/0134344 A1 | 7/2003 | Mass |
| 2003/0147884 A1 | 8/2003 | Paton et al. |
| 2003/0152987 A1 | 8/2003 | Cohen et al. |
| 2003/0162796 A1 | 8/2003 | Hilberg et al. |
| 2003/0170234 A1 | 9/2003 | Hellmann |
| 2003/0202972 A1 | 10/2003 | Andya et al. |
| 2004/0037823 A9 | 2/2004 | Paton et al. |
| 2004/0082047 A1 | 4/2004 | Emery et al. |
| 2004/0106161 A1 | 6/2004 | Bossenmaier et al. |
| 2004/0258685 A1 | 12/2004 | Brunetta et al. |
| 2005/0002928 A1 | 1/2005 | Hellmann |
| 2005/0025753 A1 | 2/2005 | Han et al. |
| 2005/0063972 A1 | 3/2005 | Basey et al. |
| 2005/0100944 A1 | 5/2005 | Cohen et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0276812 A1 | 12/2005 | Ebens et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 2/2006 | Ralph |
| 2006/0067930 A1 | 3/2006 | Adams et al. |
| 2006/0083739 A1 | 4/2006 | Sliwkowski |
| 2006/0088523 A1 | 4/2006 | Andya et al. |
| 2006/0073143 A1 | 6/2006 | Adams et al. |
| 2006/0165702 A1 | 7/2006 | Allison et al. |
| 2006/0198843 A1 | 7/2006 | Adams et al. |
| 2006/0275305 A1 | 7/2006 | Bryant |
| 2006/0121044 A1 | 8/2006 | Amler et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0099201 A1 | 11/2006 | Andya et al. |
| 2006/0228745 A1 | 12/2006 | Mass |
| 2007/0020261 A1 | 1/2007 | Sliwkowski et al. |
| 2007/0026001 A1 | 1/2007 | Ashkenazi et al. |
| 2007/0037228 A1 | 2/2007 | Moecks et al. |
| 2007/0166753 A1 | 7/2007 | Mass et al. |
| 2007/0184055 A1 | 8/2007 | Sliwkowski |
| 2007/0202516 A1 | 8/2007 | Mass et al. |
| 2007/0224203 A1 | 9/2007 | Friess et al. |
| 2007/0009976 A1 | 11/2007 | Lenz et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0241146 A1 | 2/2008 | Ashkenazi et al. |
| 2008/0160026 A1 | 3/2008 | Ashkenazi et al. |
| 2008/0102069 A1 | 5/2008 | Friess et al. |
| 2008/0112958 A1 | 5/2008 | Mass |
| 2008/0171040 A1 | 7/2008 | Ebens et al. |
| 2008/0187533 A1 | 7/2008 | Hellmann |
| 2008/0108096 A1 | 8/2008 | Ralph |

(56) References Cited

U.S. PATENT DOCUMENTS

| | | |
|---|---|---|
| 2008/0226659 A1 | 9/2008 | Erickson et al. |
| 2008/0286280 A1 | 11/2008 | Kallmeyer et al. |
| 2008/0317753 A1 | 12/2008 | Amler et al. |
| 2009/0087432 A1 | 2/2009 | Sliwkowski |
| 2009/0081223 A1 | 3/2009 | Allison et al. |
| 2009/0220492 A1 | 3/2009 | Basey et al. |
| 2009/0098135 A1 | 4/2009 | Belvin et al. |
| 2009/0099344 A1 | 4/2009 | Fahrner et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0239236 A1 | 9/2009 | Mass |
| 2009/0226455 A1 | 10/2009 | Filvaroff |
| 2009/0148401 A1 | 11/2009 | Mrsny |
| 2009/0148402 A1 | 11/2009 | Brunetta et al. |
| 2009/0148435 A1 | 11/2009 | Lebreton et al. |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0120053 A1 | 5/2010 | Cohen et al. |
| 2010/0196363 A1 | 5/2010 | Vanhauwere et al. |
| 2010/0112603 A1 | 6/2010 | Moecks et al. |
| 2010/0158899 A1 | 6/2010 | Andya et al. |
| 2010/0285010 A1 | 11/2010 | Friess et al. |
| 2010/0298156 A1 | 11/2010 | Lee-Hoeflich et al. |
| 2011/0044977 A1 | 2/2011 | Adler et al. |
| 2011/0129464 A1 | 2/2011 | Adams et al. |
| 2011/0027190 A1 | 3/2011 | Hasmann et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0151454 A1 | 6/2011 | Lee-Hoeflich et al. |
| 2011/0159014 A1 | 6/2011 | Lowman et al. |
| 2011/0245103 A1 | 6/2011 | Amler et al. |
| 2011/0246399 A1 | 6/2011 | Amler et al. |
| 2011/0165157 A1 | 7/2011 | Derynck et al. |
| 2011/0223159 A1 | 9/2011 | Friess et al. |
| 2011/0223619 A1 | 9/2011 | Belvin et al. |
| 2011/0236383 A1 | 9/2011 | Andya et al. |
| 2011/0033460 A1 | 10/2011 | Fendly et al. |
| 2011/0250194 A1 | 10/2011 | Hellmann |
| 2012/0065381 A1 | 3/2012 | Emery et al. |
| 2012/0107302 A1 | 3/2012 | Berry et al. |
| 2012/0107391 A1 | 3/2012 | Kelsey |
| 2012/0093838 A1 | 4/2012 | Mass |
| 2012/0251530 A1 | 4/2012 | Sliwkowski et al. |
| 2012/0003217 A1 | 5/2012 | Bryant |
| 2012/0121586 A1 | 5/2012 | Kiermaier et al. |
| 2012/0034213 A1 | 9/2012 | Hellmann |
| 2012/0034609 A1 | 9/2012 | Mass |
| 2013/0195845 A1 | 1/2013 | Fendly et al. |
| 2013/0195851 A1 | 1/2013 | Alavattam et al. |
| 2013/0039909 A1 | 2/2013 | Amler et al. |
| 2013/0108620 A1 | 2/2013 | Blattler et al. |
| 2013/0071384 A1 | 3/2013 | Andya et al. |
| 2013/0095172 A1 | 4/2013 | Alavattam et al. |
| 2013/0323180 A1 | 5/2013 | Hasmann et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 3/2014 | Dobosz et al. |
| 2014/0186343 A1 | 3/2014 | Harris et al. |
| 2014/0186347 A1 | 3/2014 | Derynck et al. |
| 2014/0186867 A1 | 3/2014 | Harris et al. |
| 2014/0248274 A1 | 4/2014 | Kallmeyer et al. |
| 2014/0248609 A1 | 4/2014 | Mass |
| 2014/0140993 A1 | 5/2014 | Ross et al. |
| 2014/0212411 A1 | 7/2014 | Blattler et al. |
| 2014/0128580 A1 | 8/2014 | Ebens, Jr. et al. |
| 2014/0227255 A1 | 8/2014 | Bauss et al. |
| 2014/0308277 A1 | 10/2014 | Gennaro et al. |
| 2014/0322202 A1 | 10/2014 | Cohen |
| 2014/0341886 A1 | 11/2014 | Hellmann |
| 2016/0175438 A1 | 6/2016 | Alavattam et al. |
| 2016/0376377 A1 | 12/2016 | Basey et al. |
| 2017/0029527 A1 | 2/2017 | Paton et al. |
| 2017/0073777 A1 | 3/2017 | Lee-Hoeflich et al. |
| 2017/0136026 A1 | 5/2017 | Sliwkowski et al. |
| 2017/0166656 A1 | 6/2017 | Lowman et al. |
| 2017/0174785 A1 | 6/2017 | Harris et al. |
| 2017/0190786 A1 | 6/2017 | Fendly et al. |
| 2017/0035907 A1 | 9/2017 | Green et al. |
| 2017/0037147 A1 | 9/2017 | Allison et al. |
| 2017/0008971 A1 | 12/2017 | Dennis et al. |
| 2018/0118781 A1 | 3/2018 | Lebreton et al. |
| 2018/0280408 A1 | 4/2018 | Belvin et al. |
| 2018/0282428 A1 | 4/2018 | Fendly et al. |
| 2018/0134803 A1 | 5/2018 | Douthwaite et al. |
| 2018/0162951 A1 | 6/2018 | Cohen |
| 2018/0250397 A1 | 6/2018 | Benyunes et al. |
| 2018/0251557 A1 | 6/2018 | Chui et al. |
| 2018/0201692 A1 | 7/2018 | Lowman et al. |
| 2018/0037660 A1 | 8/2018 | Gennaro et al. |
| 2018/0037661 A1 | 8/2018 | Gennaro et al. |
| 2018/0037662 A1 | 8/2018 | Gennaro et al. |
| 2018/0228895 A1 | 8/2018 | Adler et al. |
| 2018/0236072 A1 | 8/2018 | Derynck et al. |
| 2018/0236093 A1 | 8/2018 | Bryant |
| 2018/0244715 A1 | 8/2018 | Emery et al. |
| 2018/0221481 A1 | 9/2018 | Beattie et al. |
| 2018/0221488 A1 | 9/2018 | Andya et al. |
| 2018/0274038 A1 | 9/2018 | Belousov et al. |
| 2018/0296470 A1 | 10/2018 | Eng-Wong et al. |
| 2018/0327510 A1 | 11/2018 | Allison et al. |
| 2019/0055317 A1 | 2/2019 | Baughman et al. |
| 2019/0117769 A1 | 4/2019 | Benyunes et al. |
| 2019/0145985 A1* | 5/2019 | Zemo ................ G01N 33/6854 436/543 |
| 2019/0070291 A1 | 7/2019 | Mass |
| 2019/0240185 A1 | 8/2019 | Desmond-Hellman et al. |
| 2020/0206348 A1 | 2/2020 | Benyunes et al. |
| 2020/0172631 A1 | 4/2020 | Seshagiri et al. |
| 2020/0157208 A1* | 5/2020 | Barrington ........... C07K 16/244 |
| 2020/0157238 A1 | 5/2020 | Gennaro et al. |
| 2020/0237910 A1 | 7/2020 | Beattie et al. |
| 2020/0239595 A1 | 7/2020 | Allison et al. |
| 2020/0179515 A1 | 11/2020 | Andya et al. |
| 2021/0085597 A1 | 3/2021 | Eng-Wong et al. |
| 2021/0330789 A1 | 10/2021 | Benyunes et al. |
| 2022/0362379 A1 | 11/2022 | Benyunes et al. |
| 2023/0047103 A1 | 2/2023 | Gennaro et al. |
| 2023/0212311 A1 | 7/2023 | Allison et al. |
| 2023/0250187 A1 | 8/2023 | Paton et al. |
| 2023/0263895 A1 | 8/2023 | Andya et al. |
| 2023/0277663 A1 | 9/2023 | Ross et al. |
| 2023/0277664 A1 | 9/2023 | Ross et al. |
| 2023/0310455 A1 | 10/2023 | Schutzman et al. |
| 2023/0314420 A1 | 10/2023 | Avenal et al. |
| 2023/0416401 A1 | 12/2023 | Harris et al. |
| 2024/0252634 A1 | 8/2024 | Benyunes et al. |
| 2024/0262932 A1 | 8/2024 | Harris et al. |
| 2024/0269064 A1 | 8/2024 | Eng-Wong et al. |

FOREIGN PATENT DOCUMENTS

| | | |
|---|---|---|
| WO | 99/31140 A1 | 6/1999 |
| WO | 01/89566 A1 | 11/2001 |
| WO | 2004/078140 A2 | 9/2004 |
| WO | 2006/044908 A2 | 4/2006 |

(56) References Cited

FOREIGN PATENT DOCUMENTS

| WO | 2006/078307 | A1 |   | 7/2006 |             |
|----|-------------|----|---|--------|-------------|
| WO | 2006/091871 | A1 |   | 8/2006 |             |
| WO | 2008/031531 | A1 |   | 3/2008 |             |
| WO | 2011/012637 | A2 |   | 2/2011 |             |
| WO | 2011/012637 | A3 |   | 2/2011 |             |
| WO | 2011/012637 | A4 |   | 2/2011 |             |
| WO | 2011/069074 | A2 |   | 6/2011 |             |
| WO | 2016/044334 | A1 |   | 3/2016 |             |
| WO | 2016/044396 | A1 |   | 3/2016 |             |
| WO | 2018/136412 | A2 |   | 7/2018 |             |
| WO | WO-2019175125 | A1 | * | 9/2019 | ....... A61K 39/39541 |
| WO | 2023/178019 | A1 |   | 9/2023 |             |

OTHER PUBLICATIONS

Agus, D., et al., "Phase I clinical study of pertuzumab, a novel HER dimerization inhibitor, in patients with advanced cancer" J Clin Oncol 23(11):2534-2543 (Apr. 10, 2005).

Agus, D., et al., "Targeting ligand-activated ErbB2 signaling inhibits breast and prostate tumor growth" Cancer Cell 2(2):127-137 (Aug. 1, 2002).

Allison, D., et al., "Pharmacokinetics of HER2-targeted rhuMAb 2C4 (pertuzumab) in patients with advanced solid malignancies: Phase Ia results" Pro Am Soc Clin Oncol 22:197 (Jun. 3, 2003).

Arming, S. et al., "In vitro Mutagenesis of PH-20 Hyaluronidase from Human Sperm" Eur J Biochem 247(3):810-814 (Aug. 1, 1997).

Arthur, A., "Innovations in subcutaneous infusions" J Infus Nurs 38(3):179-187 (May 31, 2015).

Assouline, S., et al., "Pharmacokinetics and safety of subcutaneous rituximab plus fludarabine and cyclophosphamide for patients with chronic lymphocytic leukaemia" Br J Clin Pharmacol 80(5):1001-1009 (Nov. 1, 2015).

Aulton, M. Aulton's Pharmaceutics—The Design and Manufacture of Medicines "Excerpt pp. 317-319" Third edition,Churchill Livingstone,: 1-5 (Jan. 1, 2007).

Baselga, J., et al., "Objective response rate in a phase II multicenter trial of pertuzumab (P), a HER2 dimerization inhibiting monoclonal antibody, in combination with trastuzumab (T) in patients (pts) with HER2-positive metastatic breast cancer (MBC) which has progressed during treatment with T" J Clin Oncol (Abstract 1004; 2007 ASCO Annual Meeting), 25(18S):1-2 (Jun. 20, 2007).

Baselga, J., et al., "Pertuzumab plus trastuzumab plus docetaxel for metastatic breast cancer" N Engl J Med 366(2):109-119 (Jan. 12, 2012).

Baselga, J., et al., "Phase II study of weekly intravenous recombinant humanized anti-p185HER2 monoclonal antibody in patients with HER2/neu-overexpressing metastatic breast cancer" J Clin Oncol 14(3):737-744 (Mar. 1, 1996).

BC Cancer Drug Agency et al., "BC Cancer Agency Cancer Drug Manual" (Drug Name: Pertuzumab; Common Trade Name(s): PERJETA),:1-6 (Jan. 1, 2014).

Beaute, J., et al., "Economic evaluation of immunoglobulin replacement in patients with primary antibody deficiencies" Clin Exp Immunol 160(2):240-245 (May 1, 2010).

Berger, M., et al., "Bioavailability of IgG Administered by the Subcutaneous Route" J Clin Immunol 33(5):984-990 (Mar. 1, 2013).

Bittner, B., et al., "Development of a subcutaneous formulation for trastuzumab—nonclinical and clinical bridging approach to the approved intravenous dosing regimen" ARZNEIMIT-TELFORSCHUNG 62(9):401-409 (Sep. 1, 2012).

Bittner, B., et al., "Non-Clinical Pharmacokinetic/Pharmacodynamic and Early Clinical Studies Supporting Development a Novel Subcutaneous Formulation for the Monoclonal Antibody Rituximab" Drug Res (Stuttg). 64(11):569-575 (Nov. 1, 2014).

Bookbinder, L.H., et al., "A recombinant human enzyme for enhanced interstitial transport of therapeutics" J Control Release 114(2):230-241 (Aug. 28, 2006).

Bywaters, E. G. L. et al., "Reconstitution of the Dermal Barrier to Dye Spread After Hyaluronidase Injection" Brit Med J 2(4741):1178-1183 (Nov. 17, 1951).

Carpenter, J.F., et al. Rational Design of Stable Protein Formulations, Theory and Practice "Excerpt pp. 66, 187-188" New York:Kluwer Academic/Plenum Publishers,:7 ( 2002).

Celltrion Press Release, "Remsima SC joins the existing market for subcutaneous injections . . . signaling a drastic change in autoimmune treatments" MoneyToday-Korea (Interview, CEO—SEO, Jung-Jin; Korean with Eng. Transl.; Web page Access Date: Aug. 6, 2020),:1-5 (Nov. 26, 2019) https://news.mt.co.kr/mtview.php?no=2019112610162881129.

Chain, E., et al., "A Mucolytic Enzyme in Testes Extracts" Nature 144(3658):977-978 (Dec. 9, 1939).

Cherr, G. N. et al., "The PH-20 Protein in Cynomolgus Macaque Spermatozoa: Identification of Two Different Forms Exhibiting Hyaluronidase Activity" Dev Biol 175(1):142-153 (Apr. 10, 1996).

Cherry, R.S., et al., "Physical Mechanisms of Cell Damage in Microcarrier Cell Culture Bioreactors" Biotechnol Bioeng 32(8):1001-1014 (Oct. 5, 1988).

Cho, H.S., et al., "Structure of the extracellular region of HER2 alone and in complex with the Herceptin Fab" Nature 421(6924):756-760 (Feb. 13, 2003).

Clinicaltrials.gov, "A Dose-Finding Study of Pertuzumab (Perjeta) in Combination With Trastuzumab (Herceptin) in Early Breast Cancer (EBC)" (History of Changes for Study: NCT02738970; Submitted date: Jul. 1, 2016 (v4); Latest version submitted Jun. 11, 2018; Printed Jun. 29, 2021) pp. 1-10, retrieved from https://clinicaltrials.govlct2/history/NCT02738970'?V_4=View#StudyPageTop.

ClinicalTrials.gov, "A Dose-Finding Study of Pertuzumab (Perjeta) in Combination With Trastuzumab (Herceptin) in Healthy Male Participants and Women With Early Breast Cancer (EBC)" (History of Changes for Study: NCT02738970; Submitted: Jul. 1, 2016 (v4); Latest Version: Jun. 11, 2018; Printed: Jun. 2, 2021) pp. 1-12, Retrieved from: https://www.clinicaltrials_gov/ct2/show/NCT02738970.

ClinicalTrials.gov, "A Study of Pertuzumab and Trastuzumab Treatment in Combination With a Taxane in Participants With Human Epidermal Growth Factor Receptor 2 (HER2)-positive Metastatic Breast Cancer " (History of Changes for Study:NCT02019277; Submitted: Nov. 1, 2016 (v56); Latest Version: Sep. 11, 2018, Printed: Jun. 2, 2021) pp. 1-13, Retrieved from: http://clinicaltrials.gov/ct2/show/NCT02019277.

Clinicaltrials.gov, "A Study of Pertuzumab and Trastuzumab Treatment in Combination with a Taxane in Participants with Human Epidermal Growth Factor Receptor 2 (HER2)-positive Metastatic Breast Cancer" (History of Changes for Study: NCT02019277; Submitted Date: Nov. 1, 2016 (v56); Latest Version Submitted: Sep. 11, 2018; Printed: Jun. 29, 2021) pp. 1-10, Retrieved from: http://clinicaltrials.gov/ct2/history/NCT02019277'?V_56=View#StudyPageTop.

ClinicalTrials.gov, "A Study of Pertuzumab in Combination With Herceptin in Patients With HER2 Positive Breast Cancer" (History of Changes for NCT00545688; first posted: Oct. 17, 2007; Submitted Date: Nov. 1, 2016 (v120); Latest Version Submitted Jul. 5, 2017) pp. 1-85.

ClinicalTrials.gov, "Phase IIIb Study to Evaluate the Safety and Tolerability of Herceptin SC With Perjeta and Docetaxel in Patients With HER2-positive Advanced Breast Cancer" (History of Changes for Study: NCT02402712; Submitted: Nov. 1, 2016 (v23); Latest Version Submitted: Sep. 4, 2019; Printed Jun. 29, 2021) pp. 1-15, Retrieved from: https://clinicaltrials.gov/ct2/history/NCT02402712'?V_23=View#StudyPageTop.

ClinicalTrials.gov, "A Study of Pertuzumab in Addition to Chemotherapy and Trastuzumab as Adjuvant Therapy in Participants With Human Epidermal Growth Factor Receptor 2 (HER2)-Positive Primary Breast Cancer (APHINITY)" (ClinicalTrials.gov Identifier: NCT0135887; Study IDs: BO25126, TOC4939G; First Posted: May 24, 2011; Results First Posted: Jan. 5, 2018; Last Update Posted: Mar. 3, 2021),:1-48 (Mar. 1, 2021) https://clinicaltrials.gov/ct2/show/study/NCT01358877.

(56) References Cited

OTHER PUBLICATIONS

ClinicalTrials.gov, "A Study to Compare Subcutaneous (SC) Versus Intravenous (IV) Administration of Herceptin (Trastuzumab) in Women With Human Epidermal Growth Factor Receptor (HER) 2-Positive Early Breast Cancer" (ClinicalTrials.gov Identifier: NCT00950300; Study ID:BO22227, HannaH study; First Posted: Jul. 31, 2009; Results First Posted: Jan. 23, 2017; Last Updated Posted: Jan. 23, 2018),:1-75 (Dec. 21, 2017) https://clinicaltrials.gov/ct2/show/study/NCT00950300.
ClinicalTrials.gov., A Study to Evaluate Pertuzumab + Trastuzumab + Docetaxel vs. Placebo + Trastuzumab + Docetaxel in Previously Untreated HER2-Positive Metastatic Breast Cancer (Cleopatra) (ClinicalTrials.gov Identifier: NCT00567190) (first posted: Dec. 4, 2007, Version of Apr. 6, 2016 (v32); Latest Version Submitted Dec. 12, 2019) pp. 1-37.
Cortes, J., et al., "Pertuzumab Monotherapy After Trastuzumab-Based Treatment and Subsequent Reintroduction of Trastuzumab: Activity and Tolerability in Patients With Advanced Human Epidermal Growth Factor Receptor 2-Positive Breast Cancer" J Clin Oncol 30(14):1594-1600 (May 10, 2012).
Danilkovitch-Miagkova, A. et al., "Hyaluronidase 2 Negatively Regulates RON Receptor Tyrosine Kinase and Mediates Transformation of Epithelial Cells by Jaagsiekte Sheep Retrovirus" PNAS USA 100(8):4580-4585 (Apr. 15, 2003).
Davies, A., et al., "Pharmacokinetics and safety of subcutaneous rituximab in follicular lymphoma (Sabrina): stage 1 analysis of a randomised phase 3 study" Lancet Oncol 15(3):343-352 (Mar. 1, 2014).
De Cock, E., et al., "A time and motion study of subcutaneous versus intravenous trastuzumab in patients with HER2-positive early breast cancer" Cancer Med 5(3):389-397 (Mar. 1, 2016).
Denys, H., et al., "Safety and tolerability of subcutaneous trastuzumab at home administration, results of the phase IIIb open-label BELIS study in HER2-positive early breast cancer" Breast Cancer Res Treat 181(1):97-105 (May 1, 2020).
Duran-Reynals, F.,, "A spreading factor in certain snake venoms and its relation to their mode of action" J Exp Med 69(1):69-81 (Jan. 1, 1938).
European Medicines Agency, "Assessment Report—Perjeta (Pertuzumab) Procedure No. EMEA/H/C/002547/000" Committee for Medicinal Products for Human Use EMA/17250/2013(Rev. 04.12):1-123 (Dec. 13, 2012).
European Medicines Agency, "CHMP Assessment Report, Herceptin (trastuzumab) Procedure No. EMEA/H/C/000278" Committee for Medicinal Products for Human Use EMA/CHMP/751770/2012/CORR1:1-70 (Jun. 27, 2013).
European Medicines Agency, "Herceptin—Procedural Steps Taken and Scientific Information After the Authorisation" EMA/216822/2021:excerpt, pp. 1-3 ( 2021).
Friess, T., et al., "Combination treatment with erlotinib and pertuzumab against human tumor xenografts is superior to monotherapy" Clin Cancer Res 11(14):5300-5309 (Jul. 15, 2005).
Frost, G. I. et al., "A microtiter-based assay for hyaluronidase activity not requiring specialized reagents" Anal Biochem 251(2):263-269 (Sep. 5, 1997).
Frost, G. I. et al., "Purification, Cloning, and Expression of Human Plasma Hyaluronidase" Biochem Bioph Res Co 236(1):10-15 (Jul. 9, 1997).
Frost, G. I.,, "Recombinant Human Hyaluronidase (rHuPH20): an Enabling Platform for Subcutaneous Drug and Fluid Administration" Expert Opin Drug Del 4(4):427-440 (Jul. 1, 2007).
Fuentes, G., et al., "Synergy between trastuzumab and pertuzumab for human epidermal growth factor 2 (Her2) from colocalization: an in silico based mechanism" Breast Cancer Res 13(3 Suppl R54):1-9 (May 22, 2011).
Gardulf, A., "Immunoglobulin treatment for primary antibody deficiencies: advantages of the subcutaneous route" Biodrugs 21(2):105-116 (Jan. 1, 2007).
Garg, A., et al., "Population pharmacokinetic and covariate analysis of Pertuzumab, a HER2-targeted monoclonal antibody, and evaluation of a fixed, non-weight-based dose in patients with a variety of solid tumors" Cancer Chemother Pharmacol 74(4):819-829 (Oct. 1, 2014).
Genentech, Inc. et al., "Pertuzumab (PERJETA®) Prescribing Information—2020" (U.S. License No. 1048),:1-36 (Feb. 1, 2021).
Genentech, Inc. et al., "Trastuzumab (HERCEPTIN®) Prescribing Information—2020" (US License No. 1048),:1-38 (Feb. 1, 2021).
Genentech, Inc. et al., "Trastuzumab and hyaluronidase-oysk (HERCEPTIN HYLECTA™) Prescribing Information—2020" (U.S. License No. 1048),:1-31 (Feb. 1, 2019).
Genentech, Inc., "U.S. Appl. No. 12/804,703, titled: 'Subcutaneous anti-HER2 antibody formulations and uses thereof'" Excerpt Chart-Overview of Constituents of the Specific Formulations and Preferred embodiments in the US (US Patent Publication No. 2011/044977 A1),:1 (Jul. 27, 2010).
Gianni, L., et al., "5-year analysis of neoadjuvant pertuzumab and trastuzumab in patients with locally advanced, inflammatory, or early-stage HER2-positive breast cancer (NeoSphere): a multicentre, open-label, phase 2 randomised trial" Lancet Oncol 17(6):791-800 (Jun. 1, 2016).
Gianni, L., et al., "Efficacy and safety of neoadjuvant pertuzumab and trastuzumab in women with locally advanced, inflammatory, or early HER2-positive breast cancer (NeoSphere): a randomised multicentre, open-label, phase 2 trial" Lancet Oncol 13(01):25-32 (Jan. 1, 2012).
Gligorov, J., et al., "Safety and tolerability of subcutaneous trastuzumab for the adjuvant treatment of human epidermal growth factor receptor 2-positive early breast cancer: SafeHer phase III study's primary analysis of 2573 patients" Eur J Cancer 82:237-246 (Sep. 1, 2017).
Glover, Z.W., et al., "Compatibility and stability of pertuzumab and trastuzumab admixtures in I.V. infusion bags for coadministration" J Pharma Sci 102(3):794-812 (Mar. 1, 2013).
Haller, M.F.,, "Converting Intravenous Dosing to Subcutaneous Dosing With Recombinant Human Hyaluronidase" Pharma Tech 31(10):118-132 (Oct. 2, 2007).
Halozyme Therapeutics, Inc., "Recombinant hyaluronidase human injection (HYLENEX®) Prescribing Information—2016" (LBL301-05),:1-9 (Feb. 1, 2016).
Hamizi, S., et al., "Subcutaneous trastuzumab: development of a new formulation for treatment of HER2-positive early breast cancer" Onco Targets Ther 6(13):89-94 (Feb. 13, 2013).
Harari, D., et al., "Molecular mechanisms underlying ErbB2/HER2 action in breast cancer" Oncogene 19(53):6102-6114 (Dec. 1, 2000).
Harris, E.N., et al., "Endocytic Function, Glycosaminoglycan Specificity, and Antibody Sensitivity of the Recombinant Human 190-kDa Hyaluronan Receptor for Endocytosis (HARE)" J Biol Chem 279(35):36201-36209 (Aug. 27, 2004).
Heeson, S., "Sarah Heeson—Declaration under 37 CFR 1.130(a)" (Declaration filed in U.S. Appl. No. 15/872,648, filed Jan. 16, 2018, Applicants: Genentech, Inc. and F. Hoffmann-LaRoche, AG),:1-5 (Jul. 23, 2020).
HERCEPTIN (Trastuzumab) United States Prescribing Information (USPI),:1-37 (Mar. 2016)—Trastuzumab (HERCEPTIN) United States Prescribing Information (USPI).
Hoffmann-La Roche Limited et al., "Product Monograph—Perjeta, pertuzumab 420 mg/14 mL vial, Concentrate for Solution for Infusion Antineoplastic Professional Standard":1-35 (Apr. 12, 2013).
Hoffmann-La Roche, "A Study of Pertuzumab and Trastuzumab Subcutaneous (SC) Treatment in Combination With a Taxane in Participants With Human Epidermal Growth Factor Receptor 2 (HER2)-Positive Metastatic Breast Cancer (Sapphire)", (ClinicalTrials.gov Identifier NCT02019277; Study ID ML28784; First Posted Dec. 24, 2013; Last Update Received Sep. 13, 2018; Retrieved Feb. 7, 2020); 1-11 (Feb. 7, 2020) https://clinicaltrials.gov/ct2/show/NCT02019277.
Hoffmann-La Roche, "A Two-Arm Study to Evaluate the Pharmacokinetics, Efficacy, and Safety of Subcutaneous Administration of the Fixed-Dose Combination of Pertuzumab and Trastuzumab in Combination With Chemotherapy in Chinese Participants With HER2-Positive Early Breast Cancer", (ClinicalTrials.gov Identifier NCT04024462; Study ID YO41137; First Posted Jul. 18. 2019; Last

(56) References Cited

OTHER PUBLICATIONS

Update Posted Feb. 5, 2020; Retrieved Feb. 7, 2020) ; 1-13 (Feb. 7, 2020) https://clinicaltrials.gov/ct2/show/NCT04.
Hoffmann-La Roche:"A Dose-Finding Study of Pertuzumab (Perjeta) in Combination With Trastuzumab (Herceptin) in Healthy Male Participants and Women With Early Breast Cancer (EBC)", History of Changes for Study dated Apr. 11, 2016 ClinicalTrials.gov Identifier: NCT02738970, Apr. 14, 2016, Retrieved from the Internet:https://clinicaltrials.gov/ct2/show/nct02738970.
Hoffmann-La Roche:"A Dose-Finding Study of Pertuzumab (Perjeta) in Combination With Trastuzumab (Herceptin) in Healthy Male Participants and Women With Early Breast Cancer (EBC)", ClinicalTrials.gov Identifier: NCT02738970, Apr. 14, 2016; https://clinicaltrials.gov/ct2/show/nct02738970.
Hoffmann-La Roche:"A Dose-Finding Study of Pertuzumab (Perjeta) in Combination With Trastuzumab (Herceptin) in Healthy Male Participants and Women With Early Breast Cancer (EBC)", History of Changes for Study Record Versions ClinicalTrials.gov Identifier: NCT02738970, Apr. 14, 2016; https://clinicaltrials.gov/ct2/show/nct02738970.
Hoffmann-La Roche:"A Dose-Finding Study of Pertuzumab (Perjeta) in Combination With Trastuzumab (Herceptin) in Healthy Male Participants and Women With Early Breast Cancer (EBC)", History of Changes for Study submitted Jul. 1, 2016 ClinicalTrials.gov Identifier: NCT02738970, Apr. 14, 2016, Retrieved from the Internet:https://clinicaltrials.gov/ct2/show/nct02738970.
Hurvitz, S., et al., "Neoadjuvant trastuzumab, pertuzumab, and chemotherapy versus trastuzumab emtansine plus pertuzumab in patients with HER2-positive breast cancer (Kristine): a randomised, open-label, multicentre, phase 3 trial" Lancet Oncol 19(1):115-126 (Jan. 1, 2018).
HYLENEX recombinant (hyaluronidase human injection) prescribing leaflet, United States Prescribing Information (USPI),:1-9 (Revised version of Feb. 2016)—HYLENEX recombinant United States Prescribing Information (USPI).
"International Search Report—PCT/US2018/013854" (w/Written Opinion),:pp. 1-21 (Oct. 8, 2018).
"International Search Report—PCT/US2020/050363" (w/Written Opinion),:pp. 1-16 (Mar. 4, 2021).
Ismael, G., et al., "Subcutaneous versus intravenous administration of (neo)adjuvant trastuzumab in patients with HER2-positive, clinical stage I-III breast cancer (HannaH study): a phase 3, open-label, multicentre, randomised trial" Lancet Oncol 13(9):869-878 (Sep. 1, 2012).
Jackisch, C., et al., "HannaH phase III randomised study: Association of total pathological complete response with event-free survival in HER2-positive early breast cancer treated with neoadjuvant-adjuvant trastuzumab after 2 years of treatment-free follow-up" Eur J Cancer 62:62-75 (Jul. 1, 2016).
Jackisch, C., et al., "Subcutaneous Administration of Monoclonal Antibodies in Oncology" Geburtshilfe Frauenheilkd-Thieme 74(4):343-349 (Apr. 1, 2014).
Jackisch, C., et al., "Subcutaneous vs Intravenous Trastuzumab for Patients With ERBB2-Positive Early Breast Cancer: Final Analysis of the HannaH Phase 3 Randomized Clinical Trial" Jama Oncol 5(5):e190339 (1-5) (May 1, 2019).
Khan, T., "CMC Challenges in Developing Co-Formulations and Co-Administration Procedures with Multiple mAbs" AAPS National Biotechnology Conference, pp. 1-21 ( May 2, 2017).
Kirschbrown, W., et al., "A phase Ib dose-finding study of subcutaneous pertuzumab in combination with subcutaneous trastuzumab in healthy male volunteers and female with early breast cancer" Poster San Antonio Breast Cancer Symposium, San Antonio, Texas US, pp. 1 page ( Dec. 5-9, 2017).
Kirschbrown, W., et al., "A phase Ib dose-finding study of subcutaneous pertuzumab in combination with subcutaneous trastuzumab in healthy male volunteers and female with early breast cancer" (Abstract Accompanying Poster, Publication No. P5-20-07) 2017 San Antonio Breast Cancer Symposium, pp. 1 (2017).
Kirschbrown, W., et al., "Abstract P5-20-07: A phase 1b dose-Finding study of subcutaneous pertuzumab in combination with subcutaneous trastuzumab in healthy male volunteers and female patients with early breast cancer" Proceedings of the 2017 San Antonio Breast Cancer Symposium, ( Dec. 5-9, 2017).
Kirschbrown, W., et al., "Development of a Subcutaneous Fixed-Dose Combination of Pertuzumab and Trastuzumab: Results From the Phase Ib Dose-Finding Study" J Clin Pharmacol 59(5):702-716 (May 1, 2019).
Kummel, S., et al., "Abstract OT3-01-13: MetaPHER: A phase IIIb multicenter open-label single-arm safety study of subcutaneous trastuzumab in combination with pertuzumab and docetaxel in patients with HER2-positive advanced breast cancer" 38th Annual CTRC-AACR San Antonio Breast Cancer Symposium (Dec. 8-12, 2015).
Kummel, S., et al., "Subcutaneous trastuzumab and hyaluronidase-oysk with intravenous pertuzumab and docetaxel in HER2-positive advanced breast cancer: Final analysis of the phase IIIb, multicenter, open-label, single-arm MetaPHER study" Abstract (P1-18-05; Cancer Res 80:04 Suppl.) San Antonio Breast Cancer Symposium (SABCS)—2019, San Antonio, Texas -USA, pp. 1-3 ( Dec. 10-14, 2019).
Lalancette, C., et al., "Characterization of an 80-Kilodalton Bull Sperm Protein Identified as PH-20" Biol Reprod 65(2):628-636 (Aug. 1, 2001).
Lambertini, M., et al., "Dose-dense adjuvant chemotherapy in HER2-positive early breast cancer patients before and after the introduction of trastuzumab: Exploratory analysis of the GIM2 trial" Int J Cancer 147(1):160-169 (Jul. 1, 2020).
Langner, A., et al. Biopharmazie Pharmakokinetik—Bioverfugbarkeit Biwotransformation "excerpt pp. 116-149" 4th edition, Germany: Wissenschaftliche Verlagsgesellschaft mbH,:19 ( 2011).
Laurent, T.C., et al. Degradation of Bioactive Substances: Physiology and Pathophysiology "Chapter 16: Catabolism of Hyaluronan" J.H. Henriksen, Boca Raton, FL:CRC Press,:249-265 ( 1991).
Laurent, U. B., et al., "Catabolism of Hyaluronan in Rabbit Skin Takes Place Locally, In Lymph Nodes and Liver" Exp Physiol 76(5):695-703 (Sep. 1, 1991).
Loibl, S., et al., "Dual HER2-blockade with pertuzumab and trastuzumab in HER2-positive early breast cancer: a subanalysis of data from the randomized phase III GeparSepto trial" Ann Oncol 28(3):497-504 (Mar. 1, 2017).
Malik et al., "Dose-Response Studies of Recombinant Humanized Monoclonal Antibody 2C4 in Tumor Xenograft Models" Pro Am Soc Cancer Res 44: Abstract No. 773 ( 2003).
Marty, M., et al., "Randomized Phase II Trial of the Efficacy and Saftey of Trastuzumab Combined with Docetaxel in Patients with Human Epidermal Growth Factor Receptor 2-Positive Metastatic Breast Cancer Administered As First-Line Treatment" J Clin Oncol 23(19):4265-4274 (Jul. 1, 2005).
McCormack, P., "Pertuzumab: A Review of Its Use for First-Line Combination Treatment of HER2-Positive Metastatic Breast Cancer" Drugs 73(13):1491-1502 (Sep. 1, 2013).
Medi, M.B., et al., "Excipient selection in biologics and vaccines formulation development" Eur Pharma Review—Internet:1-13 (Feb. 19, 2014).
Metzger-Filho, O., et al., "Pertuzumab: Optimizing HER2 Blockade" Clin Cancer Res 19(20):5552-5556 (Oct. 15, 2013).
Moya-Horno, I., et al., "The Expanding Role of Pertuzumab in the treatment of HER2-positive breast cancer" Breast Cancer (Dove Med Press) 7:125-132 (May 21, 2015).
O'Shaughnessy, J., et al., "Patient (pt) preference and satisfaction with the subcutaneous fixed-dose combination of pertuzumab (P) and trastuzumab (H) in pts with HER2-positive early breast cancer (HER2+ eBC): Interim analysis of the open-label, randomised cross-over PHranceSCa study" Abstract (80O; Annals of Oncology, vol. 31, Suppl. S42) ESMO Breast Cancer Virtual Meeting—2020, Lugano, Switzerland, pp. 1 ( May 23-24, 2020).
Papakonstantinou, A., et al., "Efficacy and safety of tailored and dose-dense adjuvant chemotherapy and trastuzumab for resected HER2-positive breast cancer: Results from the phase 3 PANTHER trial" Cancer 126(6):1175-1182 (Mar. 15, 2020).

(56) References Cited

OTHER PUBLICATIONS

Pegram, M. et al., "Inhibitory effects of combinations of HER-2/neu antibody and chemotherapeutic agents used for treatment of human breast cancers" Oncogene 18(13):2241-2251 (Apr. 1, 1999).
Pelikan, E., et al., "Glossary of Terms and Symbols Used in Pharmacology" Trustees of Boston University (Retrieval Date: Jun. 17, 2021), ( 1995) http://viAnw.bumc.bu.edu/busm-pm/academics/resources/glossary/#I.
PERJETA (pertuzumab) United States Prescribing Information (USPI), 1-25 (Mar. 2016)—Pertuzumab (PERJETA) United States Prescribing Information (USPI).
"Pertuzumab (PERJETA) United States Prescribing Information (USPI),":1-35 (Dec. 2017)—Pertuzumab (PERJETA) United States Prescribing Information (USPI).
"Pertuzumab, Trastuzumab, and Hyaluronidase-zzxf (PHESGO) United States Prescribing Information (USPI),":1-23 (Jun. 2020)—Pertuzumab, Trastuzumab, and Hyaluronidase-zzx (PHESGO) United States Prescribing Information (USPI).
Pfeifer, S., et al. Biopharmazie (Excerpt pp. 144-191), Third edition, Berlin, Germany:Ullstein Mosby GmbH, ( 1995).
Pharmacology Review et al., "BLA File No. 125409—PERJETA (Pertuzumab)" Center for Drug Evaluation & RES (Report of Dr. John K. Leighton, Acting Dir. DABT-Division of Hematology Oncology Toxicology, Office of Hematology & Oncology Products, Application No. 125409ORIG1s000; Ref. ID. 3131984),:1-51 (May 16, 2012).
Pharmatimes Media Ltd., "Genentech's OMNITARG Fails in Phase II" PharmaTimes Media Ltd. (Printed: Jun. 15, 2021),:1-2 (May 16, 2005).
Pharmatimes Media Ltd., "Teva's subcutaneous asthma drug fails in PhIII" Pharma Times Media, Ltd (Author: McKee, S.),:1 (Jan. 28, 2018) http://www.pharmatimes.com/news/tevas_subcutaneous_asthma_drug_fails_in_phiii_1218310.
Phelps, B. M. et al., "Restricted Lateral Diffusion of PH-20, a PI-Anchored Sperm Membrane Protein" Science 240(4860):1780-1782 (Jun. 24, 1988).
Pimentel, F.F., et al., "Development of New Formulations of Biologics: Expectations, Immunogenicity, and Safety for Subcutaneous Trastuzumab" Pharmaceut Med 32(5):319-523 (Sep. 24, 2018).
Pivot, X., et al., "Patients' preference of trastuzumab administration (subcutaneous versus intravenous) in HER2-positive metastatic breast cancer: Results of the randomised MetaspHer study" Eur J Cancer 82:230-236 (Sep. 1, 2017).
Pivot, X., et al., "Patients' preferences for subcutaneous trastuzumab versus conventional intravenous infusion for the adjuvant treatment of HER2-positive early breast cancer: final analysis of 488 patients in the international, randomized, two-cohort PrefHer study" Ann Oncol 25(10):1979-1987 (Oct. 1, 2014).
Pivot, X., et al., "Preference for subcutaneous or intravenous administration of trastuzumab in patients with HER2-positive early breast cancer (PrefHer): an open-label randomised study" Lancet Oncol 14:962-970 (Sep. 1, 2013).
Poorter, R.L., et al., "Complications of an implantable venous access device (Port-a-Cath) during intermittent continuous infusion of chemotherapy" Eur J Cancer 32A(13):2262-2266 (Dec. 1, 1996).
Portera, C.C., et al., "A report of cardiac events in a phase II clinical study using trastuzumab combined with pertuzumab in HER2-positive metastatic breast cancer (MBC)" J Clin Oncol (Abstract No. 1028 (2007 ASCO Annual Meeting)), 25(18S):1028 (Jun. 20, 2007).
Qiu, X., et al., "Two-mAb Cocktail Protects Macaques Against The Makona Variant of Ebola Virus" Sci Transl Med 8(329 SUPPL 329ra33):1-11 (Mar. 9, 2016).
Quartino, A., et al., "Population pharmacokinetic and exposure—response analysis for trastuzumab administered using a subcutaneous 'manual syringe' injection or intravenously in women with HER2-positive early breast cancer" Cancer Chemother Pharmacol 77:77-88 (Jan. 1, 2016).

Roche Media Release titled "Roche's Herceptin given by subcutaneous injection offers greater convenience to patients and reduces overall healthcare costs compared to standard IV infusion", pp. 1-5 ( Mar. 23, 2012).
Roche Pharma AG et al., "Summary of Product Characteristics (SmPC) of Pertuzumab (Perjeta)" (EU Perjeta Packing Insert; EU Marketing Authorisation No. EU/1/13/813/001; Last Update: Dec. 12, 2021),:1-33 (Apr. 2, 2013) https://www.ema.europa.eu/en/documents/product-information/perjeta-epar-product-information_en.pdf.
Roche Pharma AG et al., "Summary of Product Characteristics (SmPC) Trastuzumab (Herceptin)" (EU Herception Package Insert; EU Marketing Authorisation No. EU/1/00/145/002; Last Update: Sep. 10, 2021),:1-133 (Mar. 1, 2010) https://www.ema.europa.eu/en/documents/product-information/herceptin-epar-product-information_en.pdf.
Roche's fixed-dose subcutaneous combination of Perjeta and Herceptin showed non-inferiority when compared to intravenous formulations for people with HER2-positive breast cancer, Press Release, pp. 1-3 https://www.roche.com/media/releases/med-cor-2019-09-13.htm ( Sep. 13, 2019).
Rowe et al., Handbook of Pharmaceutical Excipients(6):pp. 1-197 ( 2009).
Rummel, M., et al., "Preference for subcutaneous or intravenous administration of rituximab among patients with untreated CD20+ diffuse large B-cell lymphoma or follicular lymphoma: results from a prospective, randomized, open-label, crossover study (PrefMab)" Ann Oncol 28(4):836-842 (Apr. 1, 2017).
San Antonio Breast Cancer Symposium [SABCS] et al., "Prospectus (Dec. 5-9, 2017)" San Antonio Breast Cancer Symposium [SABCS] (Announcement of 40th Annual BC Symposium),:1-2 (2017) http://www.sabcs.org.
Scheuer, W., et al., "Strongly enhanced antitumor activity of trastuzumab and pertuzumab combination treatment on HER2-positive human xenograft tumor models" Cancer Res 69(24):9330-9336 (Dec. 15, 2009).
Schneeweiss, A., et al., "Pertuzumab plus trastuzumab in combination with standard neoadjuvant anthracycline-containing and anthracycline-free chemotherapy regimens in patients with HER2-positive early breast cancer: a randomized phase II cardiac safety study (TRYPHAENA)" Ann Oncol 24(9):2278-2284 (Sep. 1, 2013).
Scottish Medicines Consortium Trastuzumab 600 mg/5ml solution for injection (Herceptin®), NHS Scotland, pp. 1-9 ( Jan. 13, 2014).
Shivakumar, S., et al., "Catheter-associated thrombosis in patients with malignancy" J Clin Oncol 27(29):4858-4864 (Oct. 10, 2009).
Shpilberg, O., et al., "Subcutaneous administration of rituximab (MabThera) and trastuzumab (Herceptin) using hyaluronidase" BR J Cancer 109(6):1556-1561 (Sep. 17, 2013).
Slamon, D., et al., "Human breast cancer: correlation of relapse and survival with amplification of the HER-2/neu oncogene" Science 235(4785):177-182 (Jan. 9, 1987).
Slamon, D., et al., "Use of chemotherapy plus a monoclonal antibody against HER2 for metastatic breast cancer that overexpresses HER2" N Engl J Med 344(11):783-792 (Mar. 15, 2001).
Sliwkowski, M.X.,, "Ready to Parter" Nat Struct Bio 10(3):158-159 (Mar. 1, 2003).
Stoner, K., et al., "Intravenous versus Subcutaneous Drug Administration. Which Do Patients Prefer? A Systematic Review" Patient 8:145-153 (Jul. 12, 2014).
Swain, S.M., et al., "Pertuzumab, trastuzumab, and docetaxel in HER2-positive metastatic breast cancer" N Engl J Med 372(8):724-734 (Feb. 19, 2015).
Swain, S.M., et al., "Pertuzumab, trastuzumab, and standard anthracycline- and taxane-based chemotherapy for the neoadjuvant treatment of patients with HER2-positive localized breast cancer (BERENICE): a phase II, open-label, multicenter, multinational cardiac safety study" Ann Oncol 29(3):646-653 (Mar. 1, 2018).
Tammi, R., et al., "Degradation of Newly Synthesized High Molecular Mass Hyaluronan in the Epidermal and Dermal Compartments of Human Skin in Organ Culture" J Invest Dermatol 97(1):126-130 (Jul. 1, 1991).
Tan, A.R., et al., "Fixed-dose combination of pertuzumab and trastuzumab for subcutaneous injection plus chemotherapy in HER2-

(56) References Cited

OTHER PUBLICATIONS positive early breast cancer (FeDeriCa): a randomised, open-label, multicentre, non-Inferiority, phase 3 study" Lancet Oncol 22(1):85-97 (Jan. 1, 2021).
Tan, A.R., et al., "Subcutaneous administration of the fixed-dose combination of trastuzumab and pertuzumab in combination with chemotherapy in HER2-positive early breast cancer: Primary analysis of the phase III, multicenter, randomized, open-label, two-arm FeDeriCa study" Abstract (PD4-07) San Antonio Breast Cancer Symposium (SABCS)—2019, San Antonio, Texas—US, pp. 1 ( Dec. 10-14, 2019).
"Trastuzumab (HERCEPTIN) United States Prescribing Information (USPI),":1-38 (Apr. 2017)—Trastuzumab (HERCEPTIN) United States Prescribing Information (USPI).
U.S. Food and Drug Administration, "Drug Approval Package—Perjeta (Pertuzumab) injection," (Application No. 125409; Oct. 28, 2014 ; Approval Date Jun. 8, 2012 Retrieved from: https://web.archive.org/web/20141028115225/;http://www.accessdata.fda.gov/drugsatfda_docs/nda/2012/1254090rig1s000TOC.cfm, pp. 1.
US ClinicalTrails.gov., A Dose-Finding Study of Pertuzumab (Perjeta) in Combination With Trastuzumab (Herceptin) in Healthy Male Participants and Women With Early Breast Cancer (EBC) (ClinicalTrials.gov Identifier NCT02738970; Study ID: BO30185; First Posted Apr. 14, 2016; Last Updated Posted Jun. 12, 2018; Retrieved Feb. 7, 2020), 1-10 (Feb. 7, 2020) https://clinicaltrials.gov/ct2/show/NCT02738970.
US ClinicalTrails.gov., "A Study of Pertuzumab in Combination With Herceptin in Patients With HER2 Positive Breast Cancer (NEOSPHERE)" (Pertuzumab and Herceptin; NCT00545688; First Posted; Oct. 17, 2007; Last Update Posted: Aug. 15, 2017; Printed: Jan. 21, 2020),:1-13 https://clinicaltrials.gov/ct2/show/NCT00545688.
US ClinicalTrails.gov., "A Study to Evaluate Patient Preference and Satisfaction of Subcutaneous Administration of the Fixed-Dose Combination of Pertuzumab and Trastuzumab in Participants With HER2-Positive Early Breast Cancer (PHranceSCa)" (ClinicalTrials.gov Identifier: NCT03674112; Study ID: RO7198574: First Posted: Sep. 17, 2018; Last Update Posted: Oct. 8, 2021: Retrieved: Oct. 12, 2021),:1-20 (Oct. 12, 2021) https://clinicaltrials.gov/ct2/show/NCT03674112.
US ClinicalTrial.gov., "A Study to Compare Subcutaneous (SC) Versus Intravenous (IV) Administration of Herceptin (Trastuzumab) in Women With Human Epidermal Growth Factor Receptor (HER) 2-Positive Early Breast Cancer" (ClinicalTrials.gov Identifier: NCT00950300; Study ID: BO22227; First Posted: Jul. 13, 2009; Results First Posted: Jan. 23, 2017; Last Update Posted: Jan. 23, 2018; Retrieved: Oct. 12, 2021),:1-13 (Oct. 12, 2021) https://clinicaltrials.gov/ct2/show/study/NCT00950300.
US ClinicalTrials.gov, "A Study of Pertuzumab in Combination With Herceptin and Chemotherapy in Participants With HER2-Positive Breast Cancer" (ClinicalTrials.gov Identifier: NCT00976989; History of Changes of Study; First Posted: Sep. 15, 2009; Results First Posted: Jun. 20, 2016; Last Updated Posted: Feb. 6, 2017; Retrieved: Aug. 27, 2020),:1-10 (Aug. 27, 2020) https://clinicaltrials.gov/ct2/show/study/NCT00976989.
US ClinicalTrials.gov, "A Study to Evaluate the Pharmacokinetics, Efficacy, and Safety of Subcutaneous Administration of the Fixed-Dose Combination of Pertuzumab and Trastuzumab in Combination With Chemotherapy in Participants With HER2-Positive Early Breast Cancer (FeDeriCa)" (ClinicalTrials Identifier:NCT03493854; Study ID: WO40324; First Posted: Apr. 11, 2018; Last Update Posted: Jun. 25, 2020; Last Update Posted: Jun. 2, 2021),:1-18 (Oct. 12, 2021).
US ClinicalTrials.gov., "A Study Evaluating Pertuzumab (Perjeta) Combined With Trastuzumab (Herceptin) and Standard Anthracycline-based Chemotherapy in Participants With Human Epidermal Growth Factor Receptor 2 (HER2)-Positive Locally Advanced, Inflammatory, or Early-stage Breast Cancer (BERENICE)" (ClinicalTrials.gov Identifier: NCT02132949; Study ID: WO29217: First Posted:

May 7, 2014; Results First Posted: Apr. 13, 2017; Last Update Posted: Sep. 17, 2021),:1-15 (Oct. 12, 2021).
Von Minckwitz, G., et al., "Adjuvant Pertuzumab and Trastuzumab in Early HER2-Positive Breast Cancer" N Engl J Med 377(2):122-131 (Jul. 13, 2017).
Wasserman, R. L. et al., "Progress in gammaglobulin therapy for immunodeficiency: from subcutaneous to intravenous infusions and back again" J Clin Immunol 32(6):1153-1164 (Dec. 1, 2012).
Weissmann, B., "The Transglycosylative Action of Testicular Hyaluronidase" J Biol Chem 216(2):783-794 (Oct. 1, 1955).
Wilkinson, G. et al. Goodman & Gilman's The Pharmacological Basis of Therapeutics "Chapter 1—Pharmacokinetics—The Dynamics of Drug Absorption, Distribution, and Elimination" Tenth edition, New York, NY—US:McGraw-Hill Medical Publishing Division,:1-39 ( 2001).
Wolff, A., et al., "Human Epidermal Growth Factor Receptor 2 Testing in Breast Cancer: American Society of Clinical Oncology/College of American Pathologists Clinical Practice Guideline Focused Update" Arch Pathol Lab Med 142(11):1364-1382 (Nov. 1, 2018).
Woodard, N., et al., "Interim results from the first open-label, multicenter, phase IIIb study investigating the combination of pertuzumab with subcutaneous trastuzumab and a taxane in patients with HER2-positive metastatic breast cancer (Sapphire)" Abstract (Abstract P4-14-12, Suppl. vol. 76(4); Published: Feb. 2016) Thirty-Eighth Annual CTRC-AACR San Antonio Breast Cancer Symposium, San Antonio, Texas—US, pp. 1-2 ( Dec. 8-12, 2015).
Wynne, C. et al., "Comparison of Subcutaneous and Intravenous Administration of Trastuzumab: A Phase I/Ib Trial in Healthy Male Volunteers and Patients with HER2-Positive Breast Cancer" J Clin Pharmacol 53(2):192-201 (Jan. 24, 2013).
Yarden, Y. et al., "Untangling the ErbB signalling network" Nat Rev Mol Cell Biol 2(2):127-137 (Feb. 1, 2001).
Zheng, Y., et al., "Minipig as potential translatable model for monoclonal antibody pharmacokinetics after intravenous and subcutaneous administration" MABS 4(2):243-255 (Mar. 1, 2012).
Zielinski, C., et al., "Arzneimittel: PROFIL Onkologie Pertuzumab" Medizin Medien Austria (Austrian Drug, Medicines Agency Report on Pertuzumab—German only),:1-16 (Mar. 2016) https://media.medonline.at/ArzneimittelPROFIL-Pertuzumab_M%C3%A4rz-2016.pdf.
CSCO—Chinese Society Clinical Oncology et al., "Guidelines of the Chinese Society of Clinical Oncology [CSCO]—Breast Cancer" People's Medical Publishing House-Beijing (Excerpt pp. 12, 14—Chinese w/Eng. Translation),:12, 14 (Jan. 1, 2022).
Fathallah et al., "Immunogenicity of Subcutaneously Administered Therapeutic Proteins—a Mechanistic Perspective" The AAPS Journal 15(4):1-4 (Oct. 2013).
Jarvi, N. et al., "Immunogenicity Challenges Associated with Subcutaneous Delivery of Therapeutic Proteins, accepted Dec. 20, 2020, published online Feb. 1, 2021" BioDrugs(35):125-146 (Feb. 1, 2021).
Kirschbrown, W., et al., "Development of a Subcutaneous Fixed-Dose Combination of Pertuzumab and Trastuzumab: Results From the Phase Ib Dose-Finding Study" J Clin Pharmacol (Epub: Dec. 19, 2018), 59(2):702-716 (May 1, 2019).
Mueller, Claudia et al., "Challenges for the Pharmaceutical Technical Development of Protein Coformulations" Royal Pharmaceutical Society, Journal of Pharmacy and Pharmacology (DOI: 10.1111/jphp.12731),:666-674 (Mar. 26, 2017).
"Roche's fixed-dose subcutaneous combination of Perjeta and Herceptin comparable to intravenous formulations in people with HER2-positive breast cancer, Press Release, https://www.roche.com/media/releases/med-cor-2019-12-12.htm":1-5 (Dec. 12, 2019).
Tan, A.R. et al., "Abstract PD4-07: Subcutaneous administration of the fixed-dose combination of trastuzumab and pertuzumab in combination with chemotherapy in HER2-positive early breast cancer: Primary analysis of the phase III, multicenter, randomized, open-label, two-arm FeDeriCa study" Cancer Res (Abstract PD4-07), 80( Suppl 4):1-3 (Feb. 1, 2020).
Tan, A.R., et al., "Fixed-dose combination of pertuzumab and trastuzumab for subcutaneous injection plus chemotherapy in HER2-positive early breast cancer (FeDeriCa): a randomised, open-label,

(56) References Cited

OTHER PUBLICATIONS multicentre, non-inferiority, phase 3 study" Lancet Oncol (Epub: Dec. 21, 2020), 22(1):85-97 (Jan. 1, 2021).
"NCT03493854 Phase III, Randomized, Multicenter, Open-Label, Two-Arm Study to Evaluate the Pharmacokinetics, Efficacy, and Safety of Subcutaneous Administration of Fixed-Dose Combo of Pertuzumab & Trastuzumab in Combo w/ Chemo in Patients with HER2-Positive EBC" (ClinicalTrials.gov archive, online; retrieved from internet Jul. 9, 2024, protocol V2, https://cdn.clinicaltrials.gov/largedocs/54/NCT03493854/Prot_000. pdf, cited in JP App #2022-581373),:1-100 (Oct. 12, 2018).

\* cited by examiner

Variable Light

```
                    10                 20               30              40
2C4       DTVMTQSHKIMSTSVGDRVSITC  [KASQDVSIGVA]  WYQQRP
          **       ****  *                                    *
574       DIQMTQSPSSLSASVGDRVTITC  [KASQDVSIGVA]  WYQQKP
                                       *      * hum κI    DIQMTQSPSSLSASVGDRVTITC  [RASQSISNYLA]  WYQQKP 50                 60               70              80
2C4       GQSPKLLIY  [SASYRYT]  GVPDRFTGSGSGTDFTFTISSVQA
          **                          *  *              *      * *
574       GKAPKLLIY  [SASYRYT]  GVPSRFSGSGSGTDFTLTISSLQP
                      *  ***** hum κI    GKAPKLLIY  [AASSLES]  GVPSRFSGSGSGTDFTLTISSLQP 90                100
2C4       EDLAVYYC  [QQYYIYPYT]  FGGGTKLEIK   (SEQ ID NO. 5)
           *  *                              *    *
574       EDFATYYC  [QQYIYPYT]   FGQGTKVEIK   (SEQ ID NO. 7)
                      ***  * hum κI    EDFATYYC  [QQYNSLPWT]  FGQGTKVEIK   (SEQ ID NO. 9)
```

*FIG. 2A*

Variable Heavy

```
                    10                 20               30              40
2C4       EVQLQQSGPELVKPGTSVKISCKAS  [GFTFTDYTMD]  WVKQS
          **      **  *   *  ***     *                              *  *
574       EVQLVESGGGLVQPGGSLRLSCAAS  [GFTFTDYTMD]  WVRQA
                                          **  *  * hum III   EVQLVESGGGLVQPGGSLRLSCAAS  [GFTFSSYAMS]  WVRQA 50       a         60               70              80
2C4       HGKSLEWIG  [DVPNSGGSIYNQRFKG]  KASLTVDRSSRIVYM
           *    *   **                                  *** *      **** *
574       PGKGLEWVA  [DVPNSGGSIYNQRFKG]  RFTLSVDRSKNTLYL
                      ****  *  ****                  * * hum III   PGKGLEWVA  [VISGDGGSTYYADSVKG]  RFTISRDNSKNTLYL abc        90          100ab           110
2C4       ELRSLTFEDTAVYYCAR  [NLGPSFYFDY]  WGQGTTLTVSS   (SEQ ID NO. 6)
          ***    **                                      **
574       QMNSLRAEDTAVYYCAR  [NLGPSFYFDY]  WGQGTLVTVSS   (SEQ ID NO. 8)
                                ******** hum III   QMNSLRAEDTAVYYCAR  [GRVGYSLYDY]  WGQGTLVTVSS   (SEQ ID NO. 10)
```

*FIG. 2B*

Amino Acid Sequence for Pertuzumab Light Chain

```
1         10        20        30        40        50        60
|         |         |         |         |         |         |
DIQMTQSPSSLSASVGDRVTITCKASQDVSIGVAWYQQKPGKAPKLLIYSASYRYTGVPS 70        80        90       100       110       120
          |         |         |         |         |         |
RFSGSGSGTDFTLTISSLQPEDFATYYCQQYYIYPYTFGQGTKVEIKRTVAAPSVFIFPP 130       140       150       160       170       180
          |         |         |         |         |         |
SDEQLKSGTASVVCLLNNFYPREAKVQWKVDNALQSGNSQESVTEQDSKDSTYSLSSTLT 190       200       210
          |         |         |
LSKADYEKHKVYACEVTHQGLSSPVTKSFNRGEC (SEQ ID NO. 11)
```

*FIG. 3A*

Amino Acid Sequence for Pertuzumab Heavy Chain

```
1         10        20        30        40        50        60
|         |         |         |         |         |         |
EVQLVESGGGLVQPGGSLRLSCAASGFTFTDYTMDWVRQAPGKGLEWVADVNPNSGGSIY 70        80        90       100       110       120
          |         |         |         |         |         |
NQRFKGRFTLSVDRSKNTLYLQMNSLRAEDTAVYYCARNLGPSFYFDYWGQGTLVTVSSA 130       140       150       160       170       180
          |         |         |         |         |         |
STKGPSVFPLAPSSKSTSGGTAALGCLVKDYFPEPVTVSWNSGALTSGVHTFPAVLQSSG 190       200       210       220       230       240
          |         |         |         |         |         |
LYSLSSVVTVPSSSLGTQTYICNVNHKPSNTKVDKKVEPKSCDKTHTCPPCPAPELLGGP 250       260       270       280       290       300
          |         |         |         |         |         *|
SVFLFPPKPKDTLMISRTPEVTCVVVDVSHEDPEVKFNWYVDGVEVHNAKTKPREEQYNS 310       320       330       340       350       360
          |         |         |         |         |         |
TYRVVSVLTVLHQDWLNGKEYKCKVSNKALPAPIEKTISKAKGQPREPQVYTLPPSREEM 370       380       390       400       410       420
          |         |         |         |         |         |
TKNQVSLTCLVKGFYPSDIAVEWESNGQPENNYKTTPPVLDSDGSFFLYSKLTVDKSRWQ 430       440       448
          |         |         |
QGNVFSCSVMHEALHNHYTQKSLSLSPG (SEQ ID NO. 12)
```

*FIG. 3B*

Trastuzumab Light Chain

```
  1                                              15                             30                             45
  DIQMTQSPSSLSASVGDRVTITCRASQDVNTAVAWYQQKPGKAPK
 46                                              60                             75                             90
  LLIYSASFLYSGVPSRFSGSRSGTDFTLTISSLQPEDFATYYCQQ
 91                                             105                            120                            135
  HYTTPPTFGQGTKVEIKRTVAAPSVFIFPPSDEQLKSGTASVVCL
136                                             150                            165                            180
  LNNFYPREAKVQWKVDNALQSGNSQESVTEQDSKDSTYSLSSTLT
181                                             195                            210    214
  LSKADYEKHKVYACEVTHQGLSSPVTKSFNRGEC (SEQ ID NO. 13)
```

*FIG. 4A*

Trastuzumab Heavy Chain

```
1    E V Q L V E S G G G L V Q P G G S L R L S C A A S G F N I K D T Y I H W V R Q A P G K G L
46   E W V A R I Y P T N G Y T R Y A D S V K G R F T I S A D T S K N T A Y L Q M N S L R A E D
91   T A V Y Y C S R W G G D G F Y A M D Y W G Q G T L V T V S S A S T K G P S V F P L A P S S
136  K S T S G G T A A L G C L V K D Y F P E P V T V S W N S G A L T S G V H T F P A V L Q S S
181  G L Y S L S S V V T V P S S S L G T Q T Y I C N V N H K P S N T K V D K K V E P K S C D K
226  T H T C P P C P A P E L L G G P S V F L F P P K P K D T L M I S R T P E V T C V V V D V S
271  H E D P E V K F N W Y V D G V E V H N A K T K P R E E Q Y N S T Y R V V S V L T V L H Q D
316  W L N G K E Y K C K V S N K A L P A P I E K T I S K A K G Q P R E P Q V Y T L P P S R E E
361  M T K N Q V S L T C L V K G F Y P S D I A V E W E S N G Q P E N N Y K T T P P V L D S D G
406  S F F L Y S K L T V D K S R W Q Q G N V F S C S V M H E A L H N H Y T Q K S L S L S P G
```

(SEQ ID NO. 14)

FIG. 4B

Pertuzumab Variant Light Chain

```
  1                                             15                              30                                   45
  V H S D I Q M T Q S P S S L S A S V G D R V T I T C K A S Q D V S I G V A W Y Q Q K P G K
 46                                             60                              75                                   90
  A P K L L I Y S A S Y R Y T G V P S R F S G S G S G T D F T L T I S S L Q P E D F A T Y Y
 91                                            105                             120                                  135
  C Q Q Y Y I Y P Y T F G Q G T K V E I K R T V A A P S V F I F P P S D E Q L K S G T A S V
136                                            150                             165                                  180
  V C L L N N F Y P R E A K V Q W K V D N A L Q S G N S Q E S V T E Q D S K D S T Y S L S S
181                                            195                             210      217
  T L T L S K A D Y E K H K V Y A C E V T H Q G L S S P V T K S F N R G E C   (SEQ ID NO: 15)
```

FIG. 5A

Pertuzumab Variant Heavy Chain

```
  1 E V Q L V E S G G G L V Q P G G S L R L S C A A S G F T F T D Y T M D W V R Q A P G K G L      45
 46 E W V A D V N P N S G G S I Y N Q R F K G R F T L S V D R S K N T L Y L Q M N S L R A E D      90
 91 T A V Y Y C A R N L G P S F Y F D Y W G Q G T L V T V S S A S T K G P S V F P L A P S S K     135
136 S T S G G T A A L G C L V K D Y F P E P V T V S W N S G A L T S G V H T F P A V L Q S S G     180
181 L Y S L S S V V T V P S S S L G T Q T Y I C N V N H K P S N T K V D K K V E P K S C D K T     225
226 H T C P P C P A P E L L G G P S V F L F P P K P K D T L M I S R T P E V T C V V V D V S H     270
271 E D P E V K F N W Y V D G V E V H N A K T K P R E E Q Y N S T Y R V V S V L T V L H Q D W     315
316 L N G K E Y K C K V S N K A L P A P I E K T I S K A K G Q P R E P Q V Y T L P P S R E E M     360
361 T K N Q V S L T C L V K G F Y P S D I A V E W E S N G Q P E N N Y K T T P P V L D S D G S     405
406 F F L Y S K L T V D K S R W Q Q G N V F S C S V M H E A L H N H Y T Q K S L S L S P G K        449
    (SEQ ID NO: 16)
```

|  | Arm A: P + H IV (n=252) | | | | Arm B: PH FDC SC (n=248) | | | |
|---|---|---|---|---|---|---|---|---|
| Grade | 1-2 | 3 | 4 | 5 | 1-2 | 3 | 4 | 5 |
| Skin and subcutaneous tissue disorders | | | | | | | | |
| Alopecia | 177 (70·2%) | 1 (0·4%) | 0 | 0 | 190 (76·6%) | 1 (0·4%) | 0 | 0 |
| Rash | 44 (17·5%) | 0 | 0 | 0 | 30 (12·1%) | 1 (0·4%) | 0 | 0 |
| Dry skin | 31 (12·3%) | 0 | 0 | 0 | 32 (12·9%) | 1 (0·4%) | 0 | 0 |
| Nail disorder | 13 (5·2%) | 1 (0·4%) | 0 | 0 | 15 (6·0%) | 0 | 0 | 0 |
| Palmar-plantar erythrodysaesthesia syndrome | 11 (4·4%) | 1 (0·4%) | 0 | 0 | 13 (5·2%) | 2 (0·8%) | 0 | 0 |
| Pruritus | 18 (7·1%) | 1 (0·4%) | 0 | 0 | 8 (3·2%) | 0 | 0 | 0 |
| Nail toxicity | 7 (2·8%) | 0 | 0 | 0 | 1 (0·4%) | 1 (0·4%) | 0 | 0 |
| Skin toxicity | 3 (1·2%) | 2 (0·8%) | 0 | 0 | 2 (0·8%) | 1 (0·4%) | 0 | 0 |
| Skin exfoliation | 2 (0·8%) | 1 (0·4%) | 0 | 0 | 2 (0·8%) | 0 | 0 | 0 |
| Skin fissures | 2 (0·8%) | 0 | 0 | 0 | 1 (0·4%) | 1 (0·4%) | 0 | 0 |
| Gastrointestinal disorders | | | | | | | | |
| Nausea | 150 (59·5%) | 4 (1·6%) | 0 | 0 | 142 (57·3%) | 5 (2·0%) | 0 | 0 |
| Diarrhoea | 134 (53·2%) | 11 (4·4%) | 1 (0·4%) | 0 | 133 (53·6%) | 17 (6·9%) | 0 | 0 |
| Stomatitis | 58 (23·0%) | 2 (0·8%) | 0 | 0 | 60 (24·2%) | 2 (0·8%) | 0 | 0 |
| Constipation | 52 (20·6%) | 0 | 0 | 0 | 54 (21·8%) | 0 | 0 | 0 |
| Vomiting | 43 (17·1%) | 3 (1·2%) | 0 | 0 | 47 (19·0%) | 2 (0·8%) | 0 | 0 |
| Dyspepsia | 26 (10·3%) | 0 | 0 | 0 | 31 (12·5%) | 0 | 0 | 0 |

| | | | | | | | | |
|---|---|---|---|---|---|---|---|---|
| Abdominal pain | 13 (5·2%) | 0 | 0 | 0 | 18 (7·3%) | 1 (0·4%) | 0 | 0 |
| Dry mouth | 7 (2·8%) | 0 | 0 | 0 | 3 (1·2%) | 1 (0·4%) | 0 | 0 |
| Colitis | 0 | 1 (0·4%) | 0 | 0 | 1 (0·4%) | 1 (0·4%) | 0 | 0 |
| Abdominal pain lower | 0 | 0 | 0 | 0 | 1 (0·4%) | 1 (0·4%) | 0 | 0 |
| Gastrointestinal toxicity | 0 | 0 | 0 | 0 | 0 | 0 | 1 (0·4%) | 0 |
| Pancreatitis | 0 | 0 | 0 | 0 | 0 | 1 (0·4%) | 0 | 0 |
| General disorders and administration site conditions | | | | | | | | |
| Asthenia | 74 (29·4%) | 5 (2·0%) | 0 | 0 | 69 (27·8%) | 1 (0·4%) | 0 | 0 |
| Fatigue | 55 (21·8%) | 5 (2·0%) | 0 | 0 | 66 (26·6%) | 5 (2·0%) | 0 | 0 |
| Mucosal inflammation | 47 (18·7%) | 2 (0·8%) | 1 (0·4%) | 0 | 35 (14·1%) | 2 (0·8%) | 0 | 0 |
| Pyrexia | 38 (15·1%) | 1 (0·4%) | 0 | 0 | 30 (12·1%) | 0 | 0 | 0 |
| Injection site reaction | 2 (0·8%) | 0 | 0 | 0 | 32 (12·9%) | 0 | 0 | 0 |
| Malaise | 13 (5·2%) | 1 (0·4%) | 0 | 0 | 15 (6·0%) | 0 | 0 | 0 |
| Oedema | 6 (2·4%) | 1 (0·4%) | 0 | 0 | 7 (2·8%) | 0 | 0 | 0 |
| Nervous system disorders | | | | | | | | |
| Headache | 48 (19·0%) | 2 (0·8%) | 0 | 0 | 36 (14·5%) | 0 | 0 | 0 |
| Dysgeusia | 35 (13·9%) | 0 | 0 | 0 | 41 (16·5%) | 0 | 0 | 0 |
| Peripheral sensory neuropathy | 34 (13·5%) | 0 | 0 | 0 | 36 (14·5%) | 2 (0·8%) | 0 | 0 |
| Neuropathy peripheral | 28 (11·1%) | 5 (2·0%) | 0 | 0 | 27 (10·9%) | 1 (0·4%) | 0 | 0 |
| Paraesthesia | 19 (7·5%) | 0 | 0 | 0 | 21 (8·5%) | 2 (0·8%) | 0 | 0 |
| Polyneuropathy | 8 (3·2%) | 0 | 0 | 0 | 8 (3·2%) | 1 (0·4%) | 0 | 0 |
| Taste disorder | 5 (2·0%) | 1 (0·4%) | 0 | 0 | 7 (2·8%) | 0 | 0 | 0 |
| Syncope | 1 (0·4%) | 1 (0·4%) | 0 | 0 | 1 (0·4%) | 3 (1·2%) | 0 | 0 |
| Presyncope | 1 (0·4%) | 1 (0·4%) | 0 | 0 | 0 | 0 | 0 | 0 |
| Seizure | 1 (0·4%) | 0 | 0 | 0 | 0 | 0 | 1 (0·4%) | 0 |
| Musculoskeletal and connective tissue disorders | | | | | | | | |
| Myalgia | 42 (16·7%) | 1 (0·4%) | 0 | 0 | 52 (21·0%) | 1 (0·4%) | 0 | 0 |
| Arthralgia | 44 (17·5%) | 1 (0·4%) | 0 | 0 | 38 (15·3%) | 0 | 0 | 0 |
| Musculoskeletal pain | 12 (4·8%) | 0 | 0 | 0 | 9 (3·6%) | 1 (0·4%) | 0 | 0 |
| Blood and lymphatic system disorders | | | | | | | | |
| Anaemia | 96 (38·1%) | 9 (3·6%) | 2 (0·8%) | 0 | 81 (32·7%) | 3 (1·2%) | 0 | 0 |
| Neutropenia | 44 (17·5%) | 12 (4·8%) | 22 (8·7%) | 0 | 26 (10·5%) | 19 (7·7%) | 16 (6·5%) | 0 |
| Leukopenia | 31 (12·3%) | 3 (1·2%) | 2 (0·8%) | 0 | 13 (5·2%) | 6 (2·4%) | 0 | 0 |
| Febrile neutropenia | 0 | 11 (4·4%) | 3 (1·2%) | 0 | 0 | 14 (5·6%) | 2 (0·8%) | 0 |
| Leukocytosis | 4 (1·6%) | 1 (0·4%) | 0 | 0 | 7 (2·8%) | 0 | 0 | 0 |
| Lymphopenia | 5 (2·0%) | 3 (1·2%) | 0 | 0 | 3 (1·2%) | 1 (0·4%) | 0 | 0 |
| Neutrophilia | 2 (0·8%) | 1 (0·4%) | 0 | 0 | 2 (0·8%) | 0 | 0 | 0 |
| Investigations | | | | | | | | |

*FIG. 12B*

| | | | | | | | | |
|---|---|---|---|---|---|---|---|---|
| Alanine aminotransferase increased | 46 (18·3%) | 3 (1·2%) | 0 | 0 | 31 (12·5%) | 4 (1·6%) | 0 | 0 |
| Aspartate aminotransferase increased | 36 (14·3%) | 2 (0·8%) | 0 | 0 | 25 (10·1%) | 2 (0·8%) | 0 | 0 |
| Neutrophil count decreased | 34 (13·5%) | 15 (6·0%) | 16 (6·3%) | 0 | 27 (10·9%) | 10 (4·0%) | 17 (6·9%) | 0 |
| White blood cell count decreased | 23 (9·1%) | 13 (5·2%) | 5 (2·0%) | 0 | 16 (6·5%) | 4 (1·6%) | 5 (2·0%) | 0 |
| Weight decreased | 11 (4·4%) | 2 (0·8%) | 0 | 0 | 22 (8·9%) | 1 (0·4%) | 0 | 0 |
| Ejection fraction decreased | 12 (4·8%) | 2 (0·8%) | 0 | 0 | 9 (3·6%) | 0 | 0 | 0 |
| Lymphocyte count decreased | 3 (1·2%) | 3 (1·2%) | 0 | 0 | 5 (2·0%) | 3 (1·2%) | 0 | 0 |
| Transaminases increased | 4 (1·6%) | 0 | 0 | 0 | 1 (0·4%) | 1 (0·4%) | 0 | 0 |
| Clostridium test positive | 0 | 1 (0·4%) | 0 | 0 | 0 | 0 | 0 | 0 |
| Hepatic enzyme increased | 0 | 1 (0·4%) | 0 | 0 | 0 | 0 | 0 | 0 |
| Respiratory, thoracic, and mediastinal disorders | | | | | | | | |
| Cough | 30 (11·9%) | 0 | 0 | 0 | 32 (12·9%) | 1 (0·4%) | 0 | 0 |
| Epistaxis | 34 (13·5%) | 1 (0·4%) | 0 | 0 | 27 (10·9%) | 0 | 0 | 0 |
| Dyspnoea | 11 (4·4%) | 0 | 0 | 0 | 23 (9·3%) | 2 (0·8%) | 0 | 0 |
| Dyspnoea exertional | 6 (2·4%) | 0 | 0 | 0 | 3 (1·2%) | 1 (0·4%) | 0 | 0 |
| Pulmonary embolism | 1 (0·4%) | 0 | 0 | 0 | 0 | 2 (0·8%) | 1 (0·4%) | 0 |
| Pneumothorax | 0 | 1 (0·4%) | 0 | 0 | 0 | 0 | 0 | 0 |
| Injury, poisoning, and procedural complications | | | | | | | | |
| Procedural pain | 23 (9·1%) | 0 | 0 | 0 | 30 (12·1%) | 0 | 0 | 0 |
| Infusion-related reaction | 33 (13·1%) | 2 (0·8%) | 0 | 0 | 9 (3·6%) | 0 | 0 | 0 |
| Radiation skin injury | 17 (6·7%) | 1 (0·4%) | 0 | 0 | 19 (7·7%) | 1 (0·4%) | 0 | 0 |
| Post-procedural haematoma | 0 | 0 | 0 | 0 | 3 (1·2%) | 1 (0·4%) | 0 | 0 |
| Postoperative wound complication | 1 (0·4%) | 0 | 0 | 0 | 1 (0·4%) | 1 (0·4%) | 0 | 0 |
| Femur fracture | 0 | 0 | 0 | 0 | 0 | 1 (0·4%) | 0 | 0 |
| Flap necrosis | 0 | 0 | 0 | 0 | 0 | 1 (0·4%) | 0 | 0 |
| Post-procedural haemorrhage | 0 | 0 | 0 | 0 | 0 | 1 (0·4%) | 0 | 0 |
| Metabolism and nutrition disorders | | | | | | | | |
| Decreased appetite | 46 (18·3%) | 1 (0·4%) | 0 | 0 | 38 (15·3%) | 2 (0·8%) | 0 | 0 |
| Hypokalaemia | 18 (7·1%) | 0 | 0 | 0 | 11 (4·4%) | 4 (1·6%) | 0 | 0 |
| Hypomagnesaemia | 2 (0·8%) | 1 (0·4%) | 0 | 0 | 4 (1·6%) | 0 | 0 | 0 |

FIG. 12C

| | P+H IV | | | | PH FDC SC | | | |
|---|---|---|---|---|---|---|---|---|
| Vascular disorders | | | | | | | | |
| Hot flush | 26 (10·3%) | 0 | 0 | 0 | 19 (7·7%) | 0 | 0 | 0 |
| Hypertension | 3 (1·2%) | 1 (0·4%) | 0 | 0 | 4 (1·6%) | 5 (2·0%) | 0 | 0 |
| Haematoma | 2 (0·8%) | 1 (0·4%) | 0 | 0 | 6 (2·4%) | 0 | 0 | 0 |
| Psychiatric disorders | | | | | | | | |
| Insomnia | 27 (10·7%) | 1 (0·4%) | 0 | 0 | 37 (14·9%) | 0 | 0 | 0 |
| Depression | 5 (2·0%) | 0 | 1 (0·4%) | 0 | 10 (4·0%) | 0 | 0 | 0 |
| Eye disorders | | | | | | | | |
| Lacrimation increased | 13 (5·2%) | 0 | 0 | 0 | 12 (4·8%) | 1 (0·4%) | 0 | 0 |
| Dry eye | 8 (3·2%) | 0 | 0 | 0 | 12 (4·8%) | 1 (0·4%) | 0 | 0 |
| Cataract | 0 | 1 (0·4%) | 0 | 0 | 1 (0·4%) | 0 | 0 | 0 |
| Reproductive system and breast disorders | | | | | | | | |
| Menstruation irregular | 5 (2·0%) | 2 (0·8%) | 0 | 0 | 3 (1·2%) | 1 (0·4%) | 0 | 0 |
| Metrorrhagia | 1 (0·4%) | 0 | 1 (0·4%) | 0 | 1 (0·4%) | 0 | 0 | 0 |
| Breast haematoma | 0 | 1 (0·4%) | 0 | 0 | 1 (0·4%) | 0 | 0 | 0 |
| Cardiac disorders | | | | | | | | |
| Arrhythmia | 3 (1·2%) | 0 | 0 | 0 | 0 | 1 (0·4%) | 0 | 0 |
| Cardiac failure | 1 (0·4%) | 1 (0·4%) | 0 | 0 | 1 (0·4%) | 1 (0·4%) | 0 | 0 |
| Acute myocardial infarction | 0 | 0 | 0 | 0 | 0 | 0 | 0 | 1 (0·4%) |
| Ventricular arrhythmia | 0 | 1 (0·4%) | 0 | 0 | 0 | 0 | 0 | 0 |
| Renal and urinary disorders | | | | | | | | |
| Renal failure | 0 | 0 | 0 | 0 | 0 | 1 (0·4%) | 1 (0·4%) | 0 |
| Hepatobiliary disorders | | | | | | | | |
| Hepatotoxicity | 1 (0·4%) | 1 (0·4%) | 0 | 0 | 1 (0·4%) | 0 | 0 | 0 |
| Immune system disorders | | | | | | | | |
| Hypersensitivity | 1 (0·4%) | 1 (0·4%) | 0 | 0 | 1 (0·4%) | 0 | 0 | 0 |
| Neoplasms benign, malignant and unspecified (including cysts and polyps) | | | | | | | | |
| Renal cell carcinoma | 0 | 1 (0·4%) | 0 | 0 | 0 | 0 | 0 | 0 |
| Endocrine disorders | | | | | | | | |
| Goitre | 0 | 0 | 1 (0·4%) | 0 | 0 | 0 | 0 | 0 |
| Surgical and medical procedures | | | | | | | | |
| Debridement | 0 | 0 | 0 | 0 | 0 | 1 (0·4%) | 0 | 0 |
| Medical device change | 0 | 0 | 0 | 0 | 0 | 1 (0·4%) | 0 | 0 |

Data are number of patients (%). NCI-CTCAE=National Cancer Institute – Common Terminology Criteria for Adverse Events. P + H IV=intravenous pertuzumab and trastuzumab. PH FDC SC=subcutaneous pertuzumab and trastuzumab fixed-dose combination.

*FIG. 12D*

| Patients with ≥1 of the following, n (%) | P + H IV pooled crossover (N = 160) | PHESGO pooled crossover (N= 160) | P + H IV pooled continuation (N = 21) | PHESGO pooled continuation (N = 137) | All patients (N = 160) |
|---|---|---|---|---|---|
| Any AE | 113 (70.6) | 120 (75.0) | 13 (61.9) | 70 (51.1) | 144 (90.0) |
| SAE* | 6 (3.8) | 2 (1.3) | 0 | 3 (2.2) | 10 (6.3) |
| Grade ≥3 AE* | 6 (3.8) | 4 (2.5) | 2 (9.5) | 4 (2.9) | 13 (8.1) |
| Most common AEs (in >5% of patients) | | | | | |
| Radiation skin injury | 27 (16.9) | 17 (10.6) | 0 | 1 (0.7) | 44 (27.5) |
| Injection site reaction† | 0 | 36 (22.5) | 0 | 10 (7.3) | 42 (26.3) |
| Diarrhoea | 16 (10.0) | 13 (8.1) | 4 (19.0) | 14 (10.2) | 35 (21.9) |
| Fatigue | 9 (5.6) | 9 (5.6) | 1 (4.8) | 4 (2.9) | 17 (10.6) |
| Arthralgia | 6 (3.8) | 8 (5.0) | 2 (9.5) | 1 (0.7) | 17 (10.6) |
| Hot flush | 6 (3.8) | 9 (5.6) | 0 | 3 (2.2) | 16 (10.0) |
| Headache | 3 (1.9) | 5 (3.1) | 2 (9.5) | 1 (0.7) | 10 (6.3) |
| Myalgia | 5 (3.1) | 3 (1.9) | 2 (9.5) | 0 | 10 (6.3) |
| Rash | 2 (1.3) | 2 (1.3) | 2 (9.5) | 2 (1.5) | 8 (5.0) |
| Bone pain | 0 | 0 | 2 (9.5) | 0 | 2 (1.3) |
| AE with fatal outcome | 0 | 0 | 0 | 0 | 0 |
| AE leading to any study treatment discontinuation | 0 | 1 (0.6) | 1 (4.8) | 0 | 2 (1.3) |

*FIG. 17*

| Most common AEs (in ≥5% of patients), n (%) | P + H IV → PH FDC SC | | PH FDC SC → P + H IV | | All patients (N = 160) |
|---|---|---|---|---|---|
| | P + H IV Cycles 1-3 (n = 80) | PH FDC SC Cycles 4-6 (n = 80) | PH FDC SC Cycles 1-3 (n = 80) | P + H IV Cycles 4-6 (n = 80) | |
| Radiation skin injury | 17 (21.3) | 7 (8.8) | 10 (12.5) | 10 (12.5) | 43 (26.9) |
| Injection site reaction | 0 | 12 (15.0) | 24 (30.0) | 0 | 36 (22.5) |
| Diarrhoea | 12 (15.0) | 7 (8.8) | 6 (7.5) | 4 (5.0) | 25 (15.6) |
| Fatigue | 5 (6.3) | 4 (5.0) | 5 (6.3) | 4 (5.0) | 15 (9.4) |
| Hot flush | 6 (7.5) | 4 (5.0) | 5 (6.3) | 0 | 15 (9.4) |
| Arthralgia | 4 (5.0) | 3 (3.8) | 5 (6.3) | 2 (2.5) | 14 (8.8) |
| Upper respiratory tract infection | 1 (1.3) | 2 (2.5) | 5 (6.3) | 4 (5.0) | 12 (7.5) |
| Pruritus | 6 (7.5) | 3 (3.8) | 0 | 1 (1.3) | 9 (5.6) |
| Erythaema | 6 (7.5) | 1 (1.3) | 1 (1.3) | 1 (1.3) | 9 (5.6) |
| Anaemia | 4 (5.0) | 2 (2.5) | 1 (1.3) | 1 (1.3) | 8 (5.0) |
| Myalgia | 4 (5.0) | 1 (1.3) | 2 (2.5) | 1 (1.3) | 8 (5.0) |
| Cough | 4 (5.0) | 1 (1.3) | 0 | 1 (1.3) | 6 (3.8) |
| Infusion-related reaction | 5 (6.3) | 0 | 0 | 1 (1.3) | 6 (3.8) |
| Lymphopenia | 4 (5.0) | 0 | 0 | 0 | 4 (2.5) |
| Radiation-associated pain | 4 (5.0) | 0 | 0 | 0 | 4 (2.5) |
| Radiation-associated pain | 4 (5.0) | 0 | 0 | 0 | 4 (2.5) |

FIG. 18

PERTUZUMAB PLUS TRASTUZUMAB FIXED DOSE COMBINATION

CROSS REFERENCE TO RELATED APPLICATIONS

This application claims the benefit of priority under 35 USC 119(e) of U.S. Provisional Patent Application Nos. 63/045,712, filed on Jun. 29, 2020 and 63/065,795, filed on Aug. 14, 2020, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jun. 23, 2021, is named P36105US2SEQLIST.txt and is 31,987 bytes in size.

FIELD OF THE INVENTION

The invention concerns a fixed dose combination (FDC) comprising pertuzumab, trastuzumab, and, optionally, recombinant human hyaluronidase (rHuPH20), which is administered subcutaneously to patients. The invention concerns, inter alia, the final efficacy and safety data for the FeDeriCa clinical trial, United States Prescribing Information (USPI) (including home-use) methods, and primary analysis of the PHranceSCa clinical trial.

BACKGROUND OF THE INVENTION

Pertuzumab (PERJETA®)
Pertuzumab is a HER2/neu receptor antagonist administered by intravenous infusion for:
Use in combination with trastuzumab and docetaxel for treatment of patients with HER2-positive metastatic breast cancer (MBC) who have not received prior anti-HER2 therapy or chemotherapy for metastatic disease.
Use in combination with trastuzumab and chemotherapy as:
neoadjuvant treatment of patients with HER2-positive, locally advanced, inflammatory, or early stage breast cancer (either greater than 2 cm in diameter or node positive) as part of a complete treatment regimen for early breast cancer.
adjuvant treatment of patients with HER2-positive early breast cancer at high risk of recurrence.
See Pertuzumab United States Prescribing Information (2020).
Trastuzumab (HERCEPTIN®)
Trastuzumab is a HER2/neu receptor antagonist administered by intravenous infusion for:
The treatment of HER2-overexpressing breast cancer.
The treatment of HER2-overexpressing metastatic gastric or gastroesophageal junction adenocarcinoma.
See Trastuzumab United States Prescribing Information (2020).
Recombinant Hyaluronidase Human Injection (HYLENEX®)
Recombinant hyaluronidase human injection is a tissue permeability modifier administered by subcutaneous fluid administration used:
in subcutaneous fluid administration for achieving hydration
to increase the dispersion and absorption of other injected drugs
in subcutaneous urography for improving resorption of radiopaque agents
See recombinant (hyaluronidase human injection) United States Prescribing Information (2020).
Trastuzumab and Hyaluronidase-Oysk (HERCEPTIN HYLECTA™)
Trastuzumab and hyaluronidase-oysk is a combination of trastuzumab, a HER2/neu receptor antagonist, and recombinant human hyaluronidase, an endoglycosidase, indicated in adults for:
The treatment of HER2-overexpressing breast cancer.
See Trastuzumab and hyaluronidase-oysk United States Prescribing Information (2020). In the HannaH study, at a median follow-up exceeding 60 months, the incidence of treatment-emergent anti-trastuzumab antibodies was 16% in patients receiving subcutaneous Trastuzumab and hyaluronidase-oysk. Neutralizing anti-trastuzumab antibodies were detected in post-baseline samples in 3/47 patients in the Trastuzumab and hyaluronidase-oysk arm. The incidence of treatment-emergent anti-recombinant human hyaluronidase antibodies was 21% ($62/295$) in the Trastuzumab and hyaluronidase-oysk arm. None of the patients who tested positive for anti-recombinant human hyaluronidase antibodies tested positive for neutralizing antibodies.
Trastuzumab and Pertuzumab Fixed Dose Combination (FDC) (PHESGO™)
HER2 overexpression occurs in ~15-20% of breast cancers (BC) and is associated with high recurrence and shorter survival. Wolff et al. Arch Pathol Lab Med 2018; 142(11): 1364-82 and Slamon et al. Science 1987; 235(4785): 177-82.
Combining intravenous pertuzumab with trastuzumab (P+H IV) and chemotherapy for HER2-positive BC led to an unprecedented overall survival (OS) improvement in the first-line metastatic setting in CLEOPATRA (Swain et al. N Engl J Med 2015; 372(8): 724-34) a significant increase in pathological complete response (pCR) rates in NeoSphere (Gianni et al. Lancet Oncol 2012; 13(1): 25-32) and a clinically meaningful improvement in invasive disease-free survival (IDFS) in patients at high risk of recurrence in the adjuvant curative setting in APHINTY (von Minckwitz et al. N Engl J Med 2017; 377(2): 122-31). Hence, P+H+ chemotherapy is standard treatment for HER2-positive early and metastatic BC (EBC/MBC).
P IV and H IV are infused over 30-60 and 30-90 min, respectively, usually for multiple cycles over a treatment course (up to 1 year in EBC; until disease progression in MBC). Establishing IV access involves an invasive procedure, which is frequently inconvenient and painful for patients, particularly if treated repeatedly. Poorter et al. Eur J Cancer 1996; 32A(13): 2262-6 and Shivakumar et al. J Clin Oncol 2009; 27(29): 4858-64.
Increased usage of IV monoclonal antibodies (mAbs) in oncology has also placed a strain on medical centres with respect to time and resources required to prepare and administer infusions, and dispose of associated materials. De Cock et al. Cancer Med 2016; 5(3): 389-97.
Available data from mAbs administered by subcutaneous (SC) injection (SC trastuzumab and rituximab/hyaluronidase human) have demonstrated that a change in route (from IV to SC) results in non-inferior serum trough concentration ($C_{trough}$), consistent anti-tumour activity, and comparable safety to that achieved with IV administration. Ismael et al. Lancet Oncol 2012; 13(9): 869-78; Jackisch et al. Eur J Cancer 2016; 62: 62-75; Jackisch et al. JAMA Oncol 2019;

5(5): e190339; Pivot et al. Lancet Oncol 2013; 14(10): 962-70; Pivot et al. Ann Oncol 2014; 25(10): 1979-87; Pivot et al. Eur J Cancer 2017; 86: 82-90; Davies et al. Lancet Oncol 2014; 15(3): 343-52; Assouline et al. Br J Clin Pharmacol 2015; 80(5): 1001-9; Rummel et al. Ann Oncol 2017; 28(4): 836-42; Gligorov et al. Eur J Cancer 2017; 82: 237-46.

P IV with H SC injection into the thigh offers a more convenient option, given the shorter 2-5-minute administration time, while maintaining similar efficacy and safety to P+H IV. Kümmel et al. Cancer Res 2019; 20(4 Suppl): Abstract P1-18-05.

SC injection has demonstrated reductions in drug administration burden and chair time, has the potential to optimise medical resource use (De Cock et al. Cancer Med 2016; 5(3): 389-97; Haller, M. Pharm Technol 2007; 31(10): 118-32) is preferred by patients (an overwhelming 88.9% preferred H SC to H IV in PrefHer), and is more satisfactory for healthcare professionals. Pivot et al. (2013); Pivot et al. (2014); Rummel et al. (2017); Pivot et al. Eur J Cancer 2017; 82: 230-6.

SC administration may also potentially allow home administration of mAbs in oncology. Several studies have demonstrated benefits in terms of costs, resources, and quality of life associated with home administration of SC biotherapeutics. Beaute et al. Clin Exp Immunol 2010; 160(2): 240-5; Gardulf, A. BioDrugs 2007; 21(2): 105-16. Given these benefits, efforts are ongoing to assess the feasibility of administering mAbs in the home.

A subcutaneous pertuzumab and trastuzumab fixed-dose combination (PH FDC SC) has been developed to offer patients less invasive and faster administration of P and H versus individual IV infusions. Because the approved P IV regimen is assumed to saturate HER2 receptor binding, predicting maximum clinical efficacy of a P SC dose with a non-inferior steady-state $C_{trough}$ should be appropriate; a non-inferior $C_{trough}$ would ensure at least the same degree of target saturation as with IV administration; therefore, ensuring similar efficacy. Kirschbrown et al. J Clin Pharmacol 2019; 59(5): 702-16.

The P dose within PH FDC SC was established in the phase 1b BO30185 dose-finding study, which showed that a single 600 mg SC P dose provides similar serum $C_{trough}$ and area under the concentration-time curve (AUC) values to those of a single 420 mg IV dose. Kirschbrown et al. (2019). The H 600 mg dose within PH FDC SC was established in the phase 1 BO22023 study and confirmed in the phase 3 HannaH trial. Ismael et al. (2012).

PH FDC SC is disclosed in US 2018/0296470 A1.

SUMMARY OF THE INVENTION

Intravenous pertuzumab (P IV) and trastuzumab (H IV) infusions are administered sequentially over 60 and 90 minutes, respectively, for loading doses, and over 30-90 minutes for maintenance doses in both cases. Following the infusion, an observation time of approximately 2-6 hours for H and 30-60 minutes for P is recommended according to local regulatory requirements outside the US. A subcutaneous formulation of H (H SC), co-formulated with recombinant human hyaluronidase (rHuPH20; a permeation enhancer that allows subcutaneous administration of higher drug volumes) was developed and approved to overcome some of the inconvenience associated with the IV infusion of H, and to ease repeated administrations over time in patients with HER2-positive breast cancer.

PH FDC SC is administered as a fixed, non-weight-based dose, similar to the approved P IV and H SC formulations, but with shorter administration time (total 5-8 minutes versus 30-90 minutes for each IV infusion).

In a first aspect, the invention concerns method of treating HER2-positive cancer in a patient comprising administering a loading dose of a fixed dose combination (FDC) of pertuzumab, trastuzumab, and recombinant human hyaluronidase (rHuPH20) by subcutaneous injection in a thigh of the patient with a subcutaneous administration device at a rate of about 2 mL/min over about 8 minutes. Optionally, the administration is followed by an about 30 minute observation period.

In one embodiment, the loading dose FDC comprises 1200 mg pertuzumab, 600 mg trastuzumab, and 30,000 units of rHuPH20, e.g. made up to 15 mL. For example, the loading dose FDC may comprise: 1200 mg pertuzumab at a concentration of 80 mg/mL, 600 mg trastuzumab at a concentration of 40 mg/mL, 2000 U/mL rHuPH20, 20 mM His-HCl pH 5.5, 70 mM trehalose, 133 mM sucrose, 0.04% polysorbate 20, and 10 mM methionine.

In one embodiment the loading dose FDC is followed by administration of maintenance doses of FDC in a thigh of the patient, each at a rate of about 2 mL/min over about 5 minutes. In one embodiment, each maintenance dose is followed by an about 15 minute observation period, provided the loading dose was well tolerated.

An exemplary maintenance dose FDC comprises: 600 mg pertuzumab, 600 mg trastuzumab, and 20,000 units of rHuPH20, e.g. to a final volume of 10 mL. An exemplary maintenance dose FDC comprises 600 mg pertuzumab at a concentration of 60 mg/mL, 600 mg trastuzumab at a concentration of 60 mg/mL, 2000 U/mL rHuPH20, 20 mM His-HCl pH 5.5, 105 mM trehalose, 100 mM sucrose, 0.04% polysorbate 20, and 10 mM methionine.

In another embodiment the invention concerns a method of neoadjuvant therapy of HER2-positive early breast cancer patients comprising:
 a. administering a fixed dose combination (FDC) of pertuzumab, trastuzumab, and recombinant human hyaluronidase (rHuPH20) by subcutaneous injection to the patients, and
 b. measuring treatment-emergent anti-pertuzumab, anti-trastuzumab, and anti-rHuPH20 antibodies in the patients, wherein treatment-emergent antibodies occur in ≤about 10% of the patients.

In one embodiment, treatment-emergent antibodies occur in less than about 8% of the patients.

In one embodiment, treatment-emergent antibodies occur in less than about 5% of the patients.

In one embodiment, treatment-emergent anti-pertuzumab, anti-trastuzumab, and anti-rHuPH20 antibodies occur in about 4.8%, 0.9%, and 0.9% of the patients, respectively.

In one embodiment, treatment-emergent antibodies are evaluated after the patients have been subcutaneously treated with:
 a. loading dose FDC (e.g. comprising 1200 mg pertuzumab, 600 mg trastuzumab, and 30,000 units of rHuPH20); and/or
 b. maintenance dose FDC administered three times (e.g. comprising 600 mg pertuzumab, 600 mg trastuzumab, and 20,000 units of rHuPH20).

In one embodiment, treatment-emergent antibodies are evaluated after administration of a loading dose FDC and/or prior to administration of a first maintenance dose FDC following surgery.

In one embodiment, the method optionally further comprises measuring whether any treatment-emergent anti-pertuzumab antibodies neutralize pertuzumab's, trastuzumab's and/or rHuPH20's activity. Among patients who tested positive for ADAs to pertuzumab, neutralizing anti-pertuzumab antibodies were detected in one patient receiving neoadjuvant therapy with the FDC. Among patients who tested positive for ADAs to trastuzumab, neutralizing anti-trastuzumab antibodies were detected in one patient receiving neoadjuvant therapy with the FDC.

In yet a further embodiment, the invention concerns a method of neoadjuvant therapy of HER2-positive early breast cancer comprising administering a pertuzumab plus trastuzumab fixed dose combination (FDC) and chemotherapy to the patient.

In one embodiment, the FDC achieves a total pathological complete response (pCR) of about 60% (e.g. 59.7; see FIG. 9).

In one embodiment, the chemotherapy comprises anthracycline and taxane.

In one embodiment, the FDC is administered following completion of the anthracycline and the taxane is administered after the FDC is administered (e.g. where the FDC and taxane are administered on the same day, but sequentially, with taxane given after the FDC).

In one embodiment, the chemotherapy comprises dose dense anthracycline (ddAC) and paclitaxel. In one embodiment, the method comprises administering ddAC every 2 weeks for 4 cycles (q2w×4) followed by FDC every 3 weeks for 4 cycles (q3w×4) in combination with paclitaxel every week for 12 weeks (qw×12).

In one embodiment, wherein the chemotherapy comprises anthracycline and cyclophosphamide (AC) and docetaxel. In one embodiment, the method comprises administering AC every 3 weeks for 4 cycles (q3w×4) followed by FDC every 3 weeks for 4 cycles (q3w×4) in combination with docetaxel (75 mg/m$^2$ escalated to 100 mg/m$^2$ if the initial dose is well tolerated) every 3 weeks for 4 cycles (q3w×4).

The data in Example 1 showed that patients treated with ddAC and paclitaxel chemotherapy together with FDC achieved a greater total pCR rate than those patients treated with AC and docetaxel together with FDC (66.7% vs. 53.1% pCR; FIG. 13) and a greater total pCR than those patients treated with ddAC and paclitaxel chemotherapy together with pertuzumab IV and trastuzumab IV (66.7% vs. 63.3% pCR: FIG. 13).

In one embodiment, the method comprises administering FDC to the patient following surgery q3w for about 1 year (up to 18 cycles).

In one embodiment, wherein the patient has hormone receptor-negative cancer. This is supported by the data demonstrating that such patients achieved the highest percentage of pCRs compared to both estrogen receptor and/or progesterone receptor-positive patients and compared with hormone-receptor negative patients treated with pertuzumab IV and trastuzumab IV (70.8% vs. 52.3% and 66% pCR, respectively; see FIG. 14).

In one embodiment, the patient has stage II-IIIA cancer. The FDC achieved a total pCR rate of 61.1% in such patients compared with 54% in stage IIIB-IIIC patients (Table 4).

In one embodiment, the patient has node-positive cancer.

In one embodiment, wherein the cancer is HER2-positive, locally advanced, inflammatory, or early stage breast cancer (either greater than 2 cm in diameter or node positive).

In yet another embodiment, the invention concerns a method of treating a HER2-positive cancer patient to whom trastuzumab and pertuzumab has been previously administered intravenously comprising:

a. administering a fixed dose combination (FDC) comprising 600 mg of pertuzumab and 600 mg of trastuzumab, wherein the patient received previous intravenous pertuzumab and trastuzumab <6 weeks earlier; or b. administering a fixed dose combination (FDC) comprising 1200 mg of pertuzumab and 600 mg of trastuzumab, wherein the patient received previous intravenous pertuzumab and trastuzumab ≥6 weeks earlier.

According to the various inventions disclosed, exemplary embodiments include: HER2-positive cancer is breast cancer; breast cancer is early breast cancer (EBC); breast cancer is metastatic breast cancer (MBC).

According to the various inventions disclosed, the FDC is used for: neoadjuvant or adjuvant therapy of the EBC; neoadjuvant treatment of adult patients with HER2-positive, locally advanced, inflammatory, or early stage breast cancer (either greater than 2 cm in diameter or node positive) as part of a complete treatment regimen for early breast cancer; adjuvant treatment of adult patients with HER2-positive early breast cancer at high risk of recurrence; in combination with docetaxel for the treatment of adult patients with HER2-positive metastatic breast cancer who have not received prior anti-HER2 therapy or chemotherapy for metastatic disease.

According to another embodiment, the invention concurs a method comprising:

a. administering the FDC to the patient, b. monitoring the patient for hypersensitivity symptoms or injection-related reaction, and c. slowing down or pausing the injection, wherein the patient has a significant injection-related reaction or permanently discontinuing the FDC if the patient experiences anaphylaxis or has a severe injection-related reaction.

According to one embodiment, the patient is pre-medicated prior to administering the FDC with an analgesic, antipyretic, and/or antihistamine, e.g. when a Grade 1 or Grade 2 hypersensitivity reaction has occurred with a prior administration of the FDC.

In one embodiment, the method concerns alternating the subcutaneous injection site for each administration of the FDC between a left and right thigh of the patient.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively); $V_L$ and $V_H$ domains of variant 574/pertuzumab (SEQ ID NOs. 7 and 8, respectively), and human $V_L$ and $V_H$ consensus frameworks (hum κ1, light kappa subgroup I; humIII, heavy subgroup III) (SEQ ID Nos. 9 and 10, respectively). Asterisks identify differences between variable domains of pertuzumab and murine monoclonal antibody 2C4 or between variable domains of pertuzumab and the human framework. Complementarity Determining Regions (CDRs) are in brackets.

FIGS. 3A and 3B show the amino acid sequences of pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of trastuzumab light chain (FIG. 4A; SEQ ID NO. 13) and heavy chain (FIG. 4B; SEQ ID NO. 14), respectively. Boundaries of the variable light and variable heavy domains are indicated by arrows.

FIGS. 5A and 5B depict a variant pertuzumab light chain sequence (FIG. 5A; SEQ ID NO. 15) and a variant pertuzumab heavy chain sequence (FIG. 5B; SEQ ID NO. 16), respectively.

FIGS. 12A-D depict all adverse events occurring in ≥10% of patients at NCI-CTCAE grade 1-2 and all grade 3-5 adverse events (safety population) for FeDeriCa.

FIG. 17 depicts adverse events at the primary analysis of PHranceSCa. AE, adverse event; H, trastuzumab; IV, intravenous; P, pertuzumab; PH FDC SC, fixed-dose combination of pertuzumab and trastuzumab for subcutaneous injection; SAE, serious adverse event; SC, subcutaneous FIG. 18 depicts adverse events before and after switching for PHranceSCa. AE, adverse event; H, trastuzumab; IV, intravenous; P, pertuzumab; PH FDC SC, fixed-dose combination of pertuzumab and trastuzumab for subcutaneous injection.

DETAILED DESCRIPTION OF THE PREFERRED EMBODIMENTS

I. Definitions

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The expressions "ErbB2" and "HER2" are used interchangeably herein and refer to human HER2 protein described, for example, in Semba et al., *PNAS* (*USA*) 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

Figure 1:
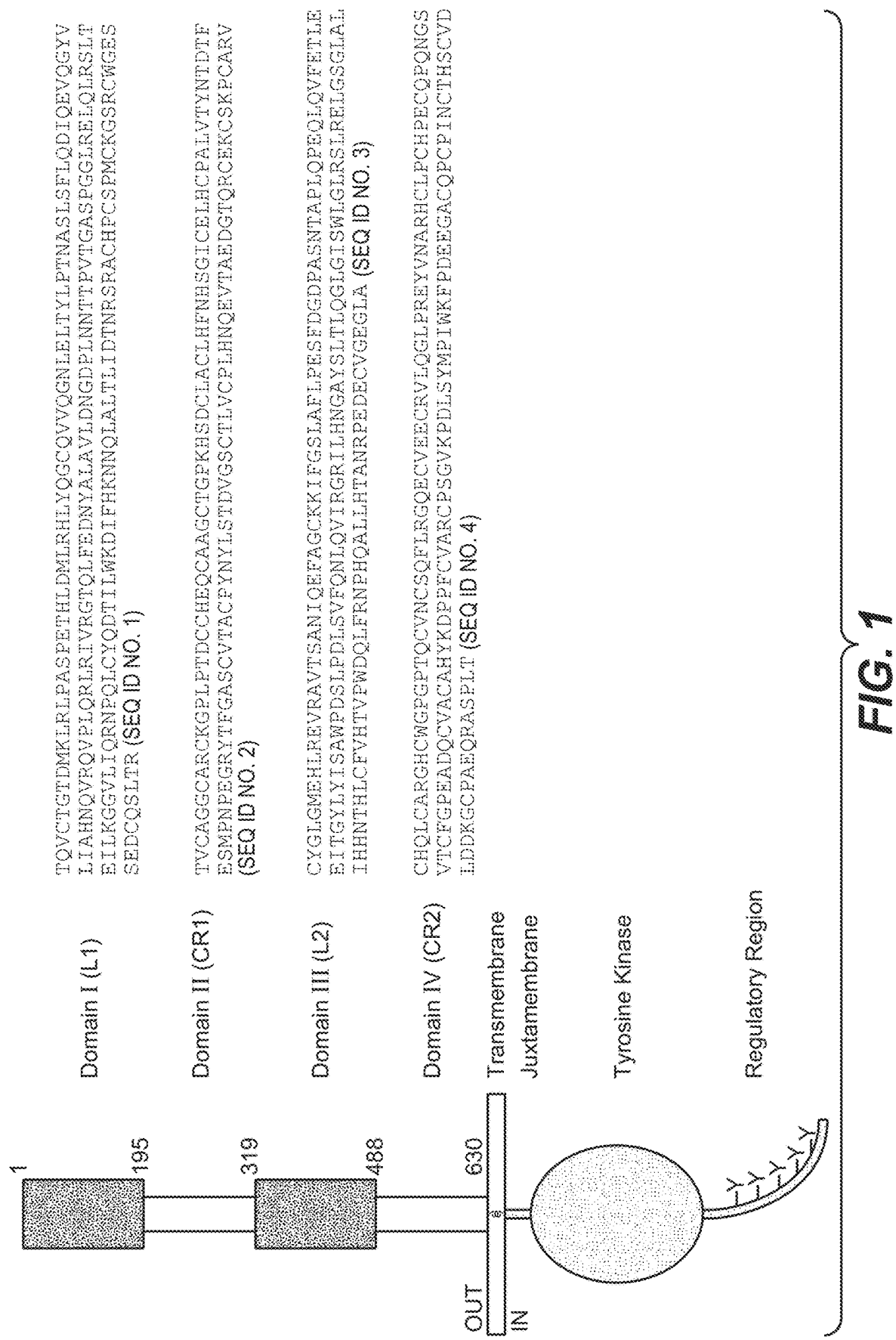
FIG. 1 provides a schematic of the HER2 protein structure, and amino acid sequences for Domains I-IV (SEQ ID Nos. 1-4, respectively) of the extracellular domain thereof.

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1. In one embodiment, the extracellular domain of HER2 may comprise four domains: "Domain I" (amino acid residues from about 1-195; SEQ ID NO:1), "Domain II" (amino acid residues from about 196-319; SEQ ID NO:2), "Domain III" (amino acid residues from about 320-488: SEQ ID NO:3), and "Domain IV" (amino acid residues from about 489-630; SEQ ID NO:4) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

"HER3" or "ErbB3" herein refer to the receptor as disclosed, for example, in U.S. Pat. Nos. 5,183,884 and 5,480,968 as well as Kraus et al. *PNAS* (*USA*) 86:9193-9197 (1989).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.*, 269(20): 14661-14665 (1994). Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER antibody" is an antibody that binds to a HER receptor. Optionally, the HER antibody further interferes with HER activation or function. Preferably, the HER antibody binds to the HER2 receptor. HER2 antibodies of interest herein are pertuzumab and trastuzumab.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

A "HER2 dimerization inhibitor" is an agent that inhibits formation of a dimer or heterodimer comprising HER2.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2 (SEQ ID NO: 2). Franklin et al. *Cancer Cell* 5:317-328 (2004).

A HER2 antibody that "binds to a heterodimeric binding site" of HER2, binds to residues in Domain II (SEQ ID NO: 2) and optionally also binds to residues in other of the domains of the HER2 extracellular domain, such as domains I and III, SEQ ID NOs: 1 and 3), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II (SEQ ID NO: 2) and optionally residues in other domain(s) of HER2, such as domains I and III (SEQ ID NOs: 1 and 3, respectively). Preferably the antibody that binds to domain II binds to the junction between domains I, II and III of HER2.

For the purposes herein, "pertuzumab" and "rhuMAb 2C4", which are used interchangeably, refer to an antibody comprising the variable light and variable heavy amino acid sequences in SEQ ID NOs: 7 and 8, respectively. Where pertuzumab is an intact antibody, it preferably comprises an IgG1 antibody; in one embodiment comprising the light chain amino acid sequence in SEQ ID NO: 11 or 15, and heavy chain amino acid sequence in SEQ ID NO: 12 or 16. The antibody is optionally produced by recombinant Chinese Hamster Ovary (CHO) cells. The terms "pertuzumab" and "rhuMAb 2C4" herein cover biosimilar versions of the drug with the United States Adopted Name (USAN) or International Nonproprietary Name (INN): pertuzumab.

For the purposes herein, "trastuzumab" and rhuMAb4D5", which are used interchangeably, refer to an antibody comprising the variable light and variable heavy amino acid sequences from within SEQ ID Nos: 13 and 14, respectively. Where trastuzumab is an intact antibody, it preferably comprises an IgG1 antibody; in one embodiment comprising the light chain amino acid sequence of SEQ ID NO: 13 and the heavy chain amino acid sequence of SEQ ID NO: 14. The antibody is optionally produced by Chinese Hamster Ovary (CHO) cells. The terms "trastuzumab" and "rhuMAb4D5" herein cover biosimilar versions of the drug with the United States Adopted Name (USAN) or International Nonproprietary Name (INN): trastuzumab.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein. Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at about 40° C. for at least about 2-4 weeks, and/or stable at about 5.0 and/or 15° C. for at least 3 months, and/or stable at about −20° C. for at least 3 months or at least 1 year. Furthermore, the formulation is preferably stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

An antibody which is "susceptible to deamidation" is one comprising one or more residue which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated at a different pH or in a different buffer.

Herein, "biological activity" of a monoclonal antibody refers to the ability of the antibody to bind to antigen and result in a measurable biological response which can be measured in vitro or in vivo. In the case of pertuzumab, in one embodiment, the biological activity refers to the ability of the formulated antibody to inhibit proliferation of the human breast cancer cell line MDA-MB-175-VII.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 5.0 to about 7.0, preferably from about 5.5 to about 6.5, for example from about 5.5 to about 6.2, such as, for example, 5.5 or 5.7. Examples of buffers that will control the pH in this range include acetate, succinate, succinate, gluconate, histidine, citrate, glycylglycine and other organic acid buffers. The preferred buffer herein is a histidine buffer.

A "histidine buffer" is a buffer comprising histidine ions. Examples of histidine buffers include histidine chloride, histidine acetate, histidine phosphate, histidine sulfate. The preferred histidine buffer identified in the examples herein was found to be histidine acetate. In the preferred embodiment, the histidine acetate buffer is prepared by titrating L-histidine (free base, solid) with acetic acid (liquid). Preferably, the histidine buffer or histidine-acetate buffer is at pH 5.5 to 6.5, or at pH 5.7 to 6.2, e.g. pH 5.7.

A "saccharide" herein comprises the general composition (CH2O)n and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. The preferred saccharide herein is a nonreducing disaccharide, such as trehalose or sucrose.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc), etc. The preferred surfactant herein is polysorbate 20.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest,* 5th Ed. Public Health Service, National Institutes of Health, Bethesda, MD (1991), expressly incorporated herein by reference. The "EU index as in Kabat" refers to the residue numbering of the human IgG1 EU antibody.

The terms "cancer" and "cancerous" refer to or describe the physiological condition in mammals that is typically characterized by unregulated cell growth.

An "advanced" cancer is one which has spread outside the site or organ of origin, either by local invasion ("locally advanced") or metastasis ("metastatic"). Accordingly, the term "advanced" cancer includes both locally advanced and metastatic disease.

"Metastatic" cancer refers to cancer which has spread from one part of the body (e.g. the breast) to another part of the body.

A "refractory" cancer is one which progresses even though an anti-tumor agent, such as a chemotherapy or biologic therapy, such as immunotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

A "non-resectable" or "unresectable" cancer is not able to be removed (resected) by surgery.

"Early-stage breast cancer" herein refers to breast cancer that has not spread beyond the breast or the axillary lymph nodes. Such cancer is generally treated with neoadjuvant or adjuvant therapy.

"Locally advanced breast cancer" has spread beyond the breast to the chest wall or the skin of the breast, or to many lymph nodes in the underarm area (axillary lymph nodes), but not to other organs.

"Inflammatory breast cancer" is a rare and very aggressive disease in which cancer cells block lymph vessels in the skin of the breast. This type of breast cancer is called "inflammatory" because the breast often looks swollen and red, or inflamed.

For the purposes herein, EBC at "high risk of recurrence" includes node positive breast cancer, comprises tumor greater than 2 cm in diameter, locally advanced breast cancer, inflammatory breast cancer, and/or hormone receptor-negative breast cancer. In one embodiment, EBC at high risk of recurrence is node positive or comprises tumor greater than 2 cm in diameter.

"Neoadjuvant therapy" or "neoadjuvant treatment" or "neoadjuvant administration" refers to systemic therapy given prior to surgery.

"Adjuvant therapy" or "adjuvant treatment" or "adjuvant administration" refers to systemic therapy given after surgery.

Herein, a "patient" or "subject" is a human patient. The patient may be a "cancer patient," i.e. one who is suffering or at risk for suffering from one or more symptoms of cancer, in particular breast cancer.

A "patient population" refers to a group of cancer patients. Such populations can be used to demonstrate statistically significant efficacy and/or safety of a drug, such as pertuzumab and/or trastuzumab.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described herein).

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via in situ hybridization (ISH), including fluorescent in situ hybridization (FISH; see WO98/45479 published October, 1998) and chromogenic in situ hybridization (CISH; see, e.g. Tanner et al., *Am. J. Pathol.* 157(5): 1467-1472 (2000); Bella et al., *J. Clin. Oncol.* 26: (May 20 suppl; abstr 22147) (2008)), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive in situ for radioactivity or by analyzing a biopsy taken from a patient previously exposed to the antibody.

A "HER2-positive" cancer comprises cancer cells which have higher than normal levels of HER2. Optionally, HER2-positive cancer has an immunohistochemistry (IHC) score of 2+ or 3+ and/or is in situ hybridization (ISH), fluorescent in situ hybridization (FISH) or chromogenic in situ hybridization (CISH) positive, e.g. has an ISH/FISH/CISH amplification ratio of ≥2.0.

A "hormone receptor negative" patient is estrogen and progesterone receptor negative, e.g. as measured by immunohistochemistry "Stage II-IIIA" breast cancer is determined by a skilled oncologist, e.g. as in Example 1.

"Node positive" breast cancer is cancer which has spread from an original breast tumor to one or more auxiliary lymph nodes.

A "HER2-mutated" cancer comprises cancer cells with a HER2-activating mutation, including kinase domain mutations, which can, for example, be identified by next generation sequencing (NGS) or real-time polymerase chain reaction (RT-PCR). "HER2-mutated" cancer specifically includes cancer characterized by insertions in exon 20 of HER2, deletions around amino acid residues 755-759 of HER2, any of the mutations G309A, G309E, S310F, D769H, D769Y, V777L, P780-Y781insGSP, V842I, R896C (Bose et al., Cancer Discov 2013; 3:1-14), as well as previously reported identical non-synonymous putative activating mutations (or indels) in COSMIC database found in two or more unique specimens. For further details see, e.g. Stephens et al., *Nature* 2004; 431:525-6; Shigematsu et al., *Cancer Res* 2005; 65:1642-6; Buttitta et al., *Int J Cancer* 2006; 119:2586-91; Li et al., *Oncogene* 2008; 27:4702-11; Sequist et al., *J Clin Oncol* 2010; 28:3076-83; Arcila et al., *Clin Cancer Res* 2012; 18:4910-8; Greulich et al., *Proc Natl Acad Sci USA* 2012; 109:14476-81; and Herter-Sprie et al., *Front Oncol* 2013; 3:1-10.

The "epitope 2C4" is the region in the extracellular domain of HER2 to which the antibody 2C4 binds. In order to screen for antibodies which bind essentially to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Domain II (SEQ ID NO: 2) in the extracellular domain of HER2. 2C4 and pertuzumab binds to the extracellular domain of HER2 at the junction of domains I, II and III (SEQ ID NOs: 1, 2, and 3, respectively). Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2 (SEQ ID NO: 4). To screen for antibodies which bind essentially to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds essentially to the 4D5 epitope of HER2 (e.g. any one or more residues in the region from about residue 529 to about residue 625, inclusive of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR, including pathological complete response, pCR), increase overall survival time, improve one or more symptoms of cancer (e.g. as assessed by FOSI).

As used herein, "pathological complete response" (pCR) or total pCR is defined as the absence of invasive neoplastic cells in the breast and in the axillary lymph nodes.

A "chemotherapy" is use of a chemical compound useful in the treatment of cancer. Examples of chemotherapeutic agents, used in chemotherapy, include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)) and anthracyclines such as annamycin, AD 32, alcarubicin, daunorubicin, doxorubicin, dexrazoxane, DX-52-1, epirubicin, GPX-100, idarubicin, valrubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; antiadrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK7 polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes; chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "taxane" is a chemotherapy which inhibits mitosis and interferes with microtubules. Examples of taxanes include paclitaxel (TAXOL®; Bristol-Myers Squibb Oncology, Princeton, N.J.); cremophor-free, albumin-engineered nanoparticle formulation of paclitaxel or nab-paclitaxel (ABRAXANE™; American Pharmaceutical Partners, Schaumberg, Illinois); and docetaxel (TAXOTERE®; Rhone-Poulenc Rorer, Antony, France). In one embodiment, the taxane is paclitaxel. In one embodiment, the taxane is docetaxel.

An "anthacycline" is a type of antibiotic that comes from the fungus *Streptococcus peucetius*, examples include: Daunorubicin, Doxorubicin, Epirubicin, and any other anthracycline chemotherapeutic agents, including those listed before.

"Anthracycline-based chemotherapy" refers to a chemotherapy regimen that consists of or includes one or more anthracycline. Examples include, without limitation, 5-FU, epirubicin, and cyclophosphamide (FEC); 5-FU, doxorubicin, and cyclophosphamide (FAC); doxorubicin and cyclophosphamide (AC); epirubicin and cyclophosphamide (EC); dose-dense doxorubicin and cyclophosphamide (ddAC), and the like.

For the purposes herein, "carboplatin-based chemotherapy" refers to a chemotherapy regimen that consists of or includes one or more Carboplatins. An example is TCH (Docetaxel/TAXOL®, Carboplatin, and trastuzumab/HERCEPTIN®).

An "aromatase inhibitor" inhibits the enzyme aromatase, which regulates estrogen production in the adrenal glands. Examples of aromatase inhibitors include: 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In one embodiment, the aromatase inhibitor herein is letrozole or anastrozole.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

The term "platin" is used herein to refer to platinum based chemotherapy, including, without limitation, cisplatin, carboplatin, and oxaliplatin.

The term "fluoropyrimidine" is used herein to refer to an antimetabolite chemotherapy, including, without limitation, capecitabine, floxuridine, and fluorouracil (5-FU).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

An "initial" or "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s). An exemplary loading dose for subcutaneous pertuzumab is 1200 mg. An exemplary loading dose for subcutaneous trastuzumab is 600 mg.

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks. An exemplary maintenance dose for subcutaneous pertuzumab is 600 mg. An exemplary maintenance dose for subcutaneous trastuzumab is 600 mg.

A "fixed dose combination" (FDC) as used herein refers to a ready-to-use co-formulation comprising a fixed dose of pertuzumab and a fixed dose of trastuzumab and, optionally, recombinant human hyaluronidase (rHuPH20). The FDC is preferably administered subcutaneously.

A "loading dose FDC" refers to a FDC providing an initial dose of pertuzumab and trastuzumab. In one embodiment, such loading dose FDC comprises 1200 mg pertuzumab, 600 mg trastuzumab, and, optionally, 30,000 units of rHuPH20, e.g. at a volume of 15 mL.

A "maintenance dose FDC" refers to a FDC providing a maintenance dose of pertuzumab and trastuzumab. In one embodiment, such maintenance dose FDC comprises 600 mg pertuzumab, 600 mg trastuzumab, and, optionally, 20,000 units of rHuPH20, e.g. at a volume of 10 mL.

A "vial" is a container suitable for holding a liquid or lyophilized preparation. In one embodiment, the vial is a single-use vial, e.g. a 10 ml or a 20 ml single-use vial with a stopper, such as a 10 ml single use glass vial with a 20 mm stopper.

A "package insert" is a leaflet that, by order of the Food and Drug Administration (FDA) or other Regulatory Authority, must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

The expression "safety data" concerns the data obtained in a controlled clinical trial showing the prevalence and severity of adverse events to guide the user regarding the safety of the drug, including guidance on how to monitor and prevent adverse reactions to the drug.

"Efficacy data" refers to the data obtained in controlled clinical trial showing that a drug effectively treats a disease, such as cancer.

By "stable mixture" when referring to a mixture of two or more drugs, such as pertuzumab and trastuzumab, means that each of the drugs in the mixture essentially retains its physical and chemical stability in the mixture as evaluated by one or more analytical assays.

Exemplary analytical assays for this purpose include: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay. In one embodiment, mixture has been shown to be stable for up to 24 hours at 5° C. or 30° C.

Administration "in combination" encompasses combined administration and separate administration, in which case, administration of one therapeutic agent can occur prior to, simultaneously, and/or following, administration of another therapeutic agents. Thus, administration of FDC and chemotherapy in combination encompasses combined administration and separate administration in either order.

A drug that is administered "concurrently" with one or more other drugs is administered during the same treatment cycle, on the same day of treatment as the one or more other drugs, and, optionally, at the same time as the one or more other drugs. For instance, for cancer therapies given every 3-weeks, the concurrently administered drugs are each administered on day-1 of a 3-week cycle.

A "subcutaneous administration device" refers to a device able to administer a FDC as disclosed herein by subcutaneous administration to a patient. Exemplary devices contemplated herein include: a syringe, an injection device, an infusion pump, an injector pen, a needleless device, an autoinjector, and a subcutaneous patch delivery system. In one embodiment, the device is a hand-held syringe, e.g. comprising a 25G-27G (⅜"-⅝") hypodermic injection needle attached or attachable to the syringe.

An "observation period" refers to a period of time after administration of a FDC that a healthcare professional monitors a patient to whom the FDC has been administered. The healthcare professional will evaluate the patient for adverse reactions, such as hypersensitivity symptoms or an injection-related reaction. An exemplary observation period after an initial administration is about 30 minutes and an exemplary observation period after a maintenance administration is about 15 minutes.

For the purposes herein, an "injection related reaction" or "administration related reaction" (ADR) refers to an adverse event, including, inter alia, hypersensitivity, analphylaxis, injection site reaction, and injection site pain, and including: Grade 1, Grade 2, Grade 3 and/or Grade 4 injection related reactions. In one embodiment, the injection related reaction is significant (and, e.g., administration of the FDC can be slowed down or paused and/or subsequent administrations of the FDC can be preceded by pre-medication with an analgesic, antipyretic, and/or antihistamine). In another embodiment, the injection related reaction is severe or Grade 3 or Grade 4 (and, e.g., administration of the FDC should be permanently discontinued). In the FeDeriCa study herein, about 21% of patients in the FDC arm had ADRs (Grades 1-4).

"Hypersensitivity" herein refers to immune-mediated reaction(s) to a drug or drugs administered to a patient. Examples include anaphylaxis, exanthema, urticaria, and/or fever. In one embodiment, the hypersensitivity symptoms are severe or Grade 3 and 4, and, e.g., administration of the FDC should be permanently discontinued. In another embodiment, the hypersensitivity reactions are mild or Grade 1 or Grade 2, and, e.g. the administration can be paused or slowed down and/or subsequent administrations of the FDC can be preceded by pre-medication with an analgesic, antipyretic, and/or antihistamine. In the FeDeriCa study herein, the incidence of hypersensitivity was 1.2% in the FDC arm.

An "injection site reaction" refers to a specific local reaction originating around the subcutaneous injection site, such as erythema, itching, discomfort and pain, including more severe manifestations such as ulceration or necrosis. In the FeDeriCa study herein, the incidence of injection site reaction to FDC was about 15% and the incidence of injection site pain from FDC administration was about 2% (with no Grade 3 or Grade 4 injection site reactions).

An "analgesic" is a drug which provides pain relief. Exemplary analgesics include acetaminophen or nonsteroidal anti-inflammatory drug (NSAID) such as salicylate.

An "antipyretic" is a fever-reducing drug. Examples include acetaminophen or nonsteroidal anti-inflammatory drug, e.g. aspirin, ibuprofen, or naproxen.

An "antihistamine" is a drug that reduces or blocks histamines, so as to treat allergy symptoms. Examples include: brompheniramine, cetirizine, chlorpheniramine, clemastine, diphenhydramine, fexofenadine, loratadine.

A "treatment-emergent antibody" is an antibody that a patient produces that binds to drug such as pertuzumab, trastuzumab, and/or rHuPH20 in the FDC. In one embodiment, treatment-emergent antibodies are measured in ≤about 10% of patients treated with the FDC. In one embodiment, treatment-emergent antibodies are measured in less than 8% of patients treated with the FDC. In one embodiment, treatment-emergent antibodies to pertuzumab, trastuzumab, and rHuPH20 are about 4.8%, 0.9%, and 0.9%, respectively, in patients treated with the FDC.

In one embodiment, the treatment-emergent antibody is "neutralizing" and inhibits the biological activity of pertuzumab, trastuzumab, and/or rHuPH20. In the FeDeriCa study, among patients who tested positive for anti-pertuzumab antibodies, neutralizing anti-pertuzumab antibodies were detected in one patient treated with FDC; among patients who tested positive for anti-trastuzumab antibodies, neutralizing anti-trastuzumab antibodies were detected in one patient treated with the FDC; and among patients who tested positive for anti-rHuPH20 antibodies, no neutralizing anti-rHuPH20 antibodies were detected.

II. Antibody and Chemotherapy Compositions (i) HER2 Antibodies

The HER2 antigen to be used for production of antibodies may be, e.g., a soluble form of the extracellular domain of a HER2 receptor or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. PNAS (USA) 88:8691-8695 (1991)) can be used to generate antibodies. Other forms of HER2 receptor useful for generating antibodies will be apparent to those skilled in the art.

Various methods for making monoclonal antibodies herein are available in the art. For example, the monoclonal antibodies may be made using the hybridoma method first described by Kohler et al., Nature, 256:495 (1975), by recombinant DNA methods (U.S. Pat. No. 4,816,567).

The anti-HER2 antibodies used in accordance with the present invention, pertuzumab and trastuzumab, are commercially available.

U.S. Pat. No. 6,949,245 describes production of exemplary humanized HER2 antibodies which bind HER2 and block ligand activation of a HER receptor.

Humanized HER2 antibodies specifically include trastuzumab as described in Table 3 of U.S. Pat. No. 5,821,337 expressly incorporated herein by reference and as defined herein; and humanized 2C4 antibodies such as pertuzumab as described and defined herein.

The humanized antibodies herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., Sequences of Proteins of Immunological Interest, 5th Ed. Public Health Service, National Institutes of Health, Bethesda, MD (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX (SEQ ID NO: 17), where X is preferably D or S; DVNPNSGGSIYNQRFKG (SEQ ID NO:18); and/or NLGPSFYFDY (SEQ ID NO:19), optionally comprising amino acid modifications of those CDR residues, e.g. where the modifications essentially maintain or improve affinity of the antibody. For example, an antibody variant for use in the methods of the present invention may have from about one to about seven or about five amino acid substitutions in the above variable heavy CDR sequences. Such antibody variants may be prepared by affinity maturation, e.g., as described below.

The humanized antibody may comprise variable light domain complementarity determining residues KASQDVSIGVA (SEQ ID NO:20); SASYX$^1$X$^2$X$^3$, where X$^1$ is preferably R or L, X$^2$ is preferably Y or E, and X$^3$ is preferably T or S (SEQ ID NO:21); and/or QQYYIYPYT (SEQ ID NO:22), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below.

The present application also contemplates affinity matured antibodies which bind HER2. The parent antibody may be a human antibody or a humanized antibody, e.g., one comprising the variable light and/or variable heavy sequences of SEQ ID Nos. 7 and 8, respectively (i.e. comprising the VL and/or VH of pertuzumab). An affinity matured variant of pertuzumab preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Humanization of murine 4D5 antibody to generate humanized variants thereof, including trastuzumab, is described in U.S. Pat. Nos. 5,821,337, 6,054,297, 6,407,213, 6,639,055, 6,719,971, and 6,800,738, as well as Carter et al. PNAS (USA), 89:4285-4289 (1992). HuMAb4D5-8 (trastuzumab) bound HER2 antigen 3-fold more tightly than the mouse 4D5 antibody, and had secondary immune function (ADCC) which allowed for directed cytotoxic activity of the humanized antibody in the presence of human effector cells. HuMAb4D5-8 comprised variable light ($V_L$) CDR residues incorporated in a $V_L$ κ subgroup I consensus framework, and variable heavy ($V_H$) CDR residues incorporated into a $V_H$ subgroup III consensus framework. The antibody further comprised framework region (FR) substitutions as positions: 71, 73, 78, and 93 of the $V_H$ (Kabat numbering of FR residues; and a FR substitution at position 66 of the $V_L$ (Kabat numbering of FR residues). trastuzumab comprises non-A allotype human γ 1 Fc region.

Various forms of the humanized antibody or affinity matured antibody are contemplated. For example, the humanized antibody or affinity matured antibody may be an antibody fragment. Alternatively, the humanized antibody or affinity matured antibody may be an intact antibody, such as an intact IgG1 antibody.

(ii) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 7 and 8, and most preferably comprising a light chain amino acid sequence of SEQ ID No. 11, and a heavy chain amino acid sequence of SEQ ID No. 12 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS–. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

For more information regarding exemplary pertuzumab compositions, see U.S. Pat. Nos. 7,560,111 and 7,879,325 as well as US 2009/0202546A1.

(iii) Trastuzumab Compositions

The trastuzumab composition generally comprises a mixture of a main species antibody (comprising light and heavy chain sequences of SEQ ID NOS: 13 and 14, respectively), and variant forms thereof, in particular acidic variants (including deamidated variants). Preferably, the amount of such acidic variants in the composition is less than about 25%, or less than about 20%, or less than about 15%. See, U.S. Pat. No. 6,339,142. See, also, Harris et al., *J. Chromatography, B* 752:233-245 (2001) concerning forms of trastuzumab resolvable by cation-exchange chromatography, including Peak A (Asn30 deamidated to Asp in both light chains); Peak B (Asn55 deamidated to isoAsp in one heavy chain); Peak 1 (Asn30 deamidated to Asp in one light chain); Peak 2 (Asn30 deamidated to Asp in one light chain, and Asp102 isomerized to isoAsp in one heavy chain); Peak 3 (main peak form, or main species antibody); Peak 4 (Asp102 isomerized to isoAsp in one heavy chain); and Peak C (Asp102 succinimide (Asu) in one heavy chain). Such variant forms and compositions are included in the invention herein.

(iv) Subcutaneous Formulations Comprising a Hyaluronidase Enzyme

Hyaluronidase enzyme acts primarily as a permeation enhancer to increase the dispersion and absorption of other co-administered drugs. Hyaluronidase transiently hydrolyses hyaluronan, component of the SC matrix, leading to reduced viscosity of the extracellular matrix of the hypodermis and, thus, to an improved delivery of subcutaneously administered drugs to the systemic circulation.

Soluble Hyaloronidase glycoproteins (sHASEGP), a process for preparing the same and their use in pharmaceutical compositions have been described in WO 2004/078140. The use of soluble Hyaluronidase glycoproteins in combination with a variety of exemplary antibodies, such as e.g. trastuzumab, has been mentioned in WO 2006/091871.

The hyaluronidase enzyme in the formulations of the present invention enhances the delivery of the anti-HER2 antibody or antibodies (e.g. pertuzumab and/or trastuzumab) to the systemic circulation, e.g. by increasing the absorption of the active substance (it acts as a permeation enhancer). The hyaluronidase enzyme also increases the delivery of the therapeutic HER2 antibody or antibodies (e.g. pertuzumab and/or trastuzumab) into the systemic circulation via the subcutaneous application route by the reversible hydrolyzation of hyaluronan, an extracellular component of the SC interstitial tissue. The hydrolysis of hyaluronan in the hypodermis temporarily opens channels in the interstitial space of the SC tissue and thereby improves the delivery of the therapeutic anti-HER2 antibody into the systemic circulation. In addition, the administration shows reduced pain in humans and less volume-derived swelling of the SC tissue.

Hyaluronidase, when administered locally has its entire effect locally. In other word hyaluronidase is inactivated and metabolized locally in minutes and has not been noted to have systemic or long term effects. The rapid inactivation of hyaluronidase within minutes when it enters the blood stream precludes a realistic ability to perform comparable biodistribution studies between different hyaluronidase products. This property also minimizes any potential systemic safety concerns because the hyaluronidase product cannot act at distant sites.

The unifying feature of all hyaluronidase enzymes is their ability to depolymerize hyaluronan, regardless of differences in chemical structure, in species source, in tissue sources, or in the batches of drug product sourced from the same species and tissue. They are unusual in that their activity is the same (except for potency) in spite of having different structures.

The hyaluronidase enzyme excipient in accordance with the formulation of the present invention is characterized by having no adverse effect on the molecular integrity of the HER2 antibody or antibodies in the stable pharmaceutical formulations described herein. Furthermore, the hyaluronidase enzyme merely modifies the delivery of the HER2 antibody or HER2 antibodies to the systemic circulation but does not possess any properties that could provide or contribute to the therapeutic effects of systemically absorbed HER2 antibody or antibodies. The hyaluronidase enzyme is not systemically bioavailable and does not adversely affect the molecular integrity of the HER2 antibody or antibodies at the recommended storage conditions of the stable pharmaceutical formulation in accordance with the invention.

A number of suitable hyaluronidase enzymes in accordance with the present invention are known from the prior art. The preferred enzyme is a human hyaluronidase enzyme, most preferably the recombinant human hyaluronidase enzyme known as rHuPH20. rHuPH20 is a member of the family of neutral and acid-active $\beta$-1,4 glycosyl hydrolases that depolymerize hyaluronan by the hydrolysis of the $\beta$-1,4 linkage between the $C_1$ position of N-acetyl glucosamine and the $C_4$ position of glucuronic acid. Hyaluronan is a polysaccharide found in the intracellular ground substance of connective tissue, such as the subcutaneous interstitial tissue, and of certain specialized tissues, such as the umbilical cord and vitreous humor. The hydrolysis of hyaluronan temporarily decreases the viscosity of the interstitial tissue and promotes the dispersion of injected fluids or of localized transudates or exudates, thus facilitating their absorption. The effects of hyaluronidase are local and reversible with complete reconstitution of the tissue hyaluronan occurring within 24 to 48 hours (Frost, G. I., "Recombinant human hyaluronidase (rHuPH20): an enabling platform for subcutaneous drug and fluid administration", Expert Opinion on Drug Delivery, 2007; 4:427-440). The increase in the permeability of connective tissue through the hydrolysis of hyaluronan correlates with the efficacy of hyaluronidase for their capability to increase the dispersion and absorption of co-administered molecules.

The human genome contains several hyaluronidase genes. Only the PH20 gene product possesses effective hyaluronidase activity under physiologic extracellular conditions and acts as a spreading agent, whereas acid-active hyaluronidases do not have this property.

rHuPH20 is the first and only recombinant human hyaluronidase enzyme currently available for therapeutic use. Naturally occurring human PH20 protein has a lipid anchor attached to the carboxy terminal amino acid that anchors it to the plasma membrane. The rHuPH20 enzyme developed by Halozyme is a truncated deletion variant that lacks such amino acids in the carboxy terminus responsible for the lipid attachment. This gives rise to a soluble, neutral pH-active enzyme similar to the protein found in bovine testes preparations. The rHuPH20 protein is synthesized with a 35 amino acid signal peptide that is removed from the N-terminus during the process of secretion. The mature rHuPH20 protein contains an authentic N-terminal amino acid sequence orthologous to that found in some bovine hyaluronidase preparations.

The PH20 hyaluronidases, including the animal derived PH20 and recombinant human rHuPH20, depolymerize hyaluronan by the hydrolysis of the $\beta$-1,4 linkage between the $C_1$ position of N-acetyl glucosamine and the $C_4$ position of glucuronic acid. The tetrasaccharide is the smallest digestion product (Weissmann, B., "The transglycosylative action of testicular hyaluronidase", J. Biol. Chem., 1955; 216: 783-94). This N-acetyl glucosamine/glucuronic acid structure is not found in N-linked glycans of recombinant biological products and therefore rHuPH20 will not affect the glycosylation of antibodies it is formulated with, such as e.g. pertuzumab or pertuzumab and trastuzumab. The rHuPH20 enzyme itself possesses six N-linked glycans per molecule with core structures similar to that found in monoclonal antibodies. As anticipated, these N-linked structures do not change over time, confirming the lack of enzymatic activity of rHuPH20 on these N-linked glycan structures. The short half-life of rHuPH20 and the constant synthesis of hyaluronan lead to a short and local action of the enzyme on tissues.

The hyaluronidase enzyme present in the subcutaneous formulation in accordance with the present invention can be prepared by using recombinant DNA technology. In this way it is ensured that the same protein (identical amino acid sequence) is obtained all the time and that an allergic reaction, e.g. caused by contaminating proteins co-purified during extraction from a tissue, is avoided. The hyaluronidase enzyme used in the formulation as exemplified herein is a human enzyme, viz. rHuPH20.

The amino acid sequence of rHuPH20 (HYLENEX™) is well known and available under CAS Registry No. 75971-58-7. The approximate molecular weight is 61 kDa.

While the safety and efficacy of hyaluronidase products has been established, there are only two monoclonal antibodies (Herceptin® and MabThera®) that have been approved for subcutaneous delivery, using hyaluronidase containing formulations. There is no known hyaluronidase containing subcutaneous formulation comprising two antibodies in the same formulation (co-formulation of two antibodies).

The concentration of the hyaluronidase enzyme depends on the actual hyaluronidase enzyme used in the preparation of the formulation in accordance with the invention. An effective amount of the hyaluronidase enzyme can be readily determined by the person skilled in the art based on the disclosure further below.

The hyaluronidase enzyme should be provided in sufficient amount to result in an increase in the dispersion and absorption of the co-administered anti-HER2 antibody or antibodies, such as pertuzumab and/or trastuzumab. The minimal amount of the hyaluronidase enzyme is at least about 150 U/ml. More particularly the effective amount of the hyaluronidase enzyme is about 150 U/ml to about 16,000 U/ml, or about 600 U/ml to about 16,000 ml, or about 1000 to 16,000 U/ml, where the latter corresponds to about 0.01 mg to 0.16 mg protein based on an assumed specific activity of 100,000 U/mg. Alternatively the concentration of the hyaluronidase enzyme is about 1,500 to 12,000 U/ml, or more particularly about 2000 U/ml or about 12,000 U/ml. The amounts specified correspond to the amount of hyaluronidase enzyme initially added to the formulation. The hyaluronidase enzyme concentrations measured in the final formulation may vary within a certain range. The ratio (w/w) of the hyaluronidase enzyme to the anti-HER2 antibody or antibodies is generally in the range of 1:1000 to 1:8,000, or in the range of 1:4,000 to 1:5,000 or about 1:6,000.

The hyaluronidase enzyme may be derived from animals, human samples or manufactured based on the recombinant DNA technology as described further below.

In some embodiments, the subcutaneous HER2 antibody formulations herein comprise recombinant human hyaluronidase (rHuPH20) at a concentration of about 600 U/mL to about 16,000 U/mL, or about 1000 U/mL to about 16,000 U/mL, or about 1000 to about 2000 U/ml, or at a concentration of about 600 U/ml, or about 667 U/mL, or about 1000 U/mL, or about 2000 U/mL, preferable about 2000 U/mL.

In some embodiments the highly concentrated, stable pertuzumab formulations of the present invention comprise a fixed dose of 600 mg or 1200 mg of pertuzumab and recombinant human hyaluronidase (rHuPH20) at a concentration of 1000 U/mL.

As noted above the soluble hyaluronidase glycoprotein may be considered to be a further excipient in the anti-HER2 formulation. The soluble hyaluronidase glycoprotein may be added to the anti-HER2 formulation at the time of manufacturing the anti-HER2 formulation or may be added shortly before the injection. Alternatively the soluble hyaluronidase glycoprotein may be provided as a separate injection. In the latter case the soluble hyaluronidase glycoprotein may be provided in a separate vial either in lyophilized form which must be reconstituted with suitable diluents before the subcutaneous injection takes place, or may be provided as a liquid formulation by the manufacturer. The anti-HER2 formulation and the soluble hyaluronidase glycoprotein may be procured as separate entities or may also be provided as kits comprising both injection components and suitable instructions for their subcutaneous administration. Suitable instructions for the reconstitution and/or administration of one or both of the formulations may also be provided.

In addition to the hyaluronidase enzyme, such as rHuPH20, the subcutaneous formulations of the present invention comprise one or more additional excipients, such as one or more buffering agents, one or more stabilizers, and/or one or more surfactants.

The buffer used in the formulations in accordance with the present invention has a pH in the range from about 5.0 to about 7.0, or from about 5.0 to about 6.0, or from about 5.3 to about 5.8, or from about 5.5 to about 5.7.

For the subcutaneous (SC) pertuzumab formulations the pH of about 5.7 has been found most suitable. A preferred pH of a subcutaneous (SC) trastuzumab formulation is about 5.5.

Examples of buffering agents that will control the pH in this range include acetate, succinate, gluconate, histidine, citrate, glycylglycine and other organic acid buffers. The most suitable buffer in accordance with the present invention is a histidine buffer, such as, for example, histidine chloride, histidine acetate, histidine phosphate, histidine sulfate, preferably a histidine chloride buffer. A histidine chloride buffer can be prepared by titrating L-histidine (free base, solid) with diluted hydrochloric acid. In particular the histidine buffer or histidine chloride buffer is an L-histidine buffer at pH of 5.5±0.6, more particularly at a pH from about 5.3 to about 5.8, and most particularly has a pH of 5.5 or 5.7.

The stabilizer may, for example, be a saccharide or a combination of saccharides, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, and iso-maltulose. A particularly suitable saccharide for use in the trastuzumab SC formulations is trehalose, and a particularly suitable saccharide for use in the pertuzumab SC formulations is sucrose.

The surfactant preferably is a nonionic surfactant. Examples of surfactants herein include polysorbate; poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. Polysorbate 20 (PS20) and Polysorbate 80 (PS80), respectively are particularly suitable for use in the formulations described herein.

III. Selecting Patients for Therapy

Detection of HER2 expression or amplification can be used to select patients for treatment in accordance with the present invention. Several FDA-approved commercial assays are available to identify HER2-positive, HER2-expressing, HER2-overexpressing or HER2-amplified cancer patients. These methods include HERCEPTEST® (Dako) and PATHWAY® HER2 (immunohistochemistry (IHC) assays) and PathVysion® and HER2 FISH pharmDx™ (FISH assays). Users should refer to the package inserts of specific assay kits for information on the validation and performance of each assay.

For example, HER2 expression or overexpression may be analyzed by IHC, e.g. using the HERCEPTEST® (Dako). Paraffin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as HER2-negative, whereas those tumors with 2+ or 3+ scores may be characterized as HER2-positive.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)).

The presence of HER2 protein overexpression and gene amplification are highly correlated, therefore, alternatively, or additionally, the use of in situ hybridization (ISH), e.g. fluorescent in situ hybridization (FISH), assays to detect gene amplification may also be employed for selection of patients appropriate for treatment in accordance with the present invention. FISH assays such as the INFORM™ (sold by Ventana, Arizona) or PathVysion® (Vysis, Illinois) may be carried out on formalin-fixed, paraffin-embedded tumor tissue to determine the extent (if any) of HER2 amplification in the tumor.

Most commonly, HER2-positive status is confirmed using archival paraffin-embedded tumor tissue, using any of the foregoing methods.

Preferably, HER2-positive patients having a 2+ or 3+ IHC score and/or who are FISH or ISH positive are selected for treatment in accordance with the present invention. Patients with 3+ IHC score and FISH/ISH positivity are particularly suitable for treatment in accordance with the present invention.

HER2 mutations associated with responsiveness to HER2-directed therapy have also been identified. Such mutations include, without limitation, insertions in exon 20 of HER2, deletions around amino acid residues 755-759 of HER2, any of the mutations G309A, G309E, S310F, D769H, D769Y, V777L, P780-Y781insGSP, V842I, R896C (Bose et al., Cancer Discov 2013; 3:1-14), as well as previously reported identical non-synonymous putative activating mutations (or indels) in COSMIC database found in two or more unique specimens.

See also U.S. Pat. No. 7,981,418 for alternative assays for screening patients for therapy with pertuzumab, and the Examples.

IV. Pharmaceutical Formulations

Therapeutic formulations of the HER2 antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), generally in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The present application specifically contemplates stable fixed-dose co-formulations (FDC) of pertuzumab and trastuzumab for subcutaneous (SC) administration.

The following SC FDC loading and maintenance formulations were found to be stable and suitable for subcutaneous administration of a single co-formulation of pertuzumab and trastuzumab to human patients:

---

Loading Dose

Pertuzumab
  Dose: 1200 mg
  Concentration: 80 mg/mL
Trastuzumab
  Dose: 600 mg
  Concentration: 40 mg/mL
rHuPH20
  Concentration: 2000 U/mL
pH: 5.5
20 mM L-Histidine/HCl
Trehalose: 70 mM
Sucrose: 133 mM
Polysorbate 20 (PS20): 0.04%; 0.4 mg/mL
10 mM Methionine
Nominal fill volume 15 mL
Vial: 20 mL/20 mm Maintenance Dose:

Pertuzumab
  Dose: 600 mg
  Concentration: 60 mg/mL
Trastuzumab
  Dose: 600 mg
  Concentration: 60 mg/mL
rHuPH20
  Concentration: 2000 U/mL
pH: 5.5
20 mM L-Histidine/HCl
Trehalose: 105 mM
Sucrose: 100 mM
Polysorbate PS20: 0.04%; 0.4 mg/mL
10 mM methionine
Nominal fill volume: 10 mL
Vial: 15 mL/20 mm

---

The formulation herein may also contain more than one active compound as necessary for the particular indication being treated, preferably those with complementary activities that do not adversely affect each other. Various drugs which can be combined with the HER dimerization inhibitor are described in the Method Section below. Such molecules are suitably present in combination in amounts that are effective for the purpose intended.

The formulations to be used for in vivo administration must be sterile. This is readily accomplished by filtration through sterile filtration membranes.

V. Treatment Methods

The invention concerns a method of treating HER2-positive cancer in a patient comprising administering a fixed dose combination (FDC) of pertuzumab, trastuzumab, and recombinant human hyaluronidase (rHuPH20) by subcutaneous injection in the thigh of the patient with a subcutaneous administration device at a rate of about 2 mL/min over about 8 minutes. This can be considered an initial or loading administration of the FDC. Optionally, the administration is followed by an about 30 minute observation period.

The method optionally further comprises administering one or more maintenance doses of the FDC in the thigh of the patient at a rate of about 2 mL/min over about 5 min. Optionally, administration of the maintenance doses are followed by an about 15 minute observation period, provided the loading dose was well tolerated. For example, 2 to 10 (e.g. about 4) administrations of the FDC are given to the patient (e.g. as a neoadjuvant therapy prior to surgery) and, optionally, further post-surgery administrations, for example about 10 to 20 (e.g. about 18) maintenance administrations of the FDC are given to the patient following surgery.

In certain embodiments, the cancer is breast cancer, ovarian cancer, peritoneal cancer, fallopian tube cancer, lung cancer, prostate cancer, colorectal cancer, biliary cancer and bladder cancer. In other embodiments, the cancer is breast cancer, peritoneal cancer, fallopian tube cancer, lung cancer, colorectal cancer, biliary cancer and bladder cancer. In a particular embodiment, the cancer is breast cancer, such as early breast cancer or metastatic breast cancer.

In one embodiment, the HER2-positive cancer breast cancer, e.g. early breast cancer (EBC) or metastatic breast cancer (MBC).

In one embodiment, the FDC comprises a liquid pharmaceutical composition comprising 1200 mg pertuzumab at a concentration of 80 mg/mL, 600 mg trastuzumab at a concentration of 40 mg/mL, 2000 U/mL rHuPH20, 20 mM His-HCl pH 5.5, 70 mM trehalose, 133 mM sucrose, 0.04% polysorbate 20, and 10 mM methionine and comprises an initial or loading FDC formulation.

In one embodiment, the FDC comprises a liquid pharmaceutical composition comprising 600 mg pertuzumab at a concentration of 60 mg/mL, 600 mg trastuzumab at a concentration of 60 mg/mL, 2000 U/mL rHuPH20, 20 mM His-HCl pH 5.5, 105 mM trehalose, 100 mM sucrose, 0.04% polysorbate 20, and 10 mM methionine and comprises a subsequent or maintenance FDC formulation.

In another embodiment, the invention comprises administering the FDC to the patient, monitoring the patient for injection-related reaction, and slowing down or pausing the injection wherein an injection-related reaction occurs. In one embodiment, the method comprising permanently discontinuing administration of the FDC if a severe injection-related reaction occurs.

In one embodiment, the method comprising alternating the subcutaneous injection site for each administration of the FDC between a left and right thigh of the patient.

In another embodiment, the invention concerns a method of treating HER2-positive cancer comprising administering a fixed dose combination (FDC) of pertuzumab, trastuzumab, and recombinant human hyaluronidase (rHuPH20) by subcutaneous injection to the patient and measuring treatment-emergent anti-pertuzumab, anti-trastuzumab, and anti-recombinant human hyaluronidase PH20 antibodies.

The invention also relates to a method of therapy HER2-positive early breast cancer comprising administering a pertuzumab plus trastuzumab fixed dose combination (PH FDC) and chemotherapy (e.g. dose dense anthracycline (ddAC) and paclitaxel), for example: comprising administering ddAC every 2 weeks for 4 weeks (q2w×4) followed by PH FDC q3 w×4 in combination with paclitaxel every week (qw) for 12 weeks.

In one embodiment, the patient has hormone receptor-negative disease and/or has stage II-IIIA disease.

The FeDeriCa data demonstrated that the FDC was more effective (tpCR) in hormone-receptor negative EBC patients, stage II-IIIA EBC patients, and EBC patients who received ddAC→paclitaxel.

In one embodiment, the method comprises administering PH FDC to the patient following surgery q3w for about 1 year (up to 18 cycles).

The PH FDC herein is administered subcutaneously to treat: HER2-positive metastatic breast cancer (MBC) who have not received prior anti-HER2 therapy or chemotherapy for metastatic disease.

For use in combination with trastuzumab and chemotherapy as:
 neoadjuvant treatment of patients with HER2-positive, locally advanced, inflammatory, or early stage breast cancer (either greater than 2 cm in diameter or node positive) as part of a complete treatment regimen for early breast cancer.
 adjuvant treatment of patients with HER2-positive early breast cancer at high risk of recurrence.

For maintenance administration, the FDC is typically administered about every three weeks as subcutaneous injection, starting with a fixed loading dose of about 1200 mg of pertuzumab and 600 mg of trastuzumab, followed by a second and any subsequent fixed maintenance doses of about 600 mg of pertuzumab and 600 mg of trastuzumab.

The injection site should be alternated between a left and the right thigh. New injections should be given at least 2.5 cm from the old site on healthy skin and not into areas where the skin is red, bruised, tender or hard.

VI. Articles of Manufacture

In another embodiment of the invention, an article of manufacture containing materials useful for the treatment of cancer. The article of manufacture comprises a subcutaneous administration device able to administer a FDC as disclosed herein by subcutaneous administration to a patient, for example a syringe, an injection device, an infusion pump, an injector pen, a needleless device, an autoinjector, and a subcutaneous patch delivery system.

In one embodiment, the device is a hand-held syringe, e.g. comprising a 25G-27G (⅜"-⅝") hypodermic injection needle.

The subcutaneous administration device contains and delivers the FDC of the pertuzumab and trastuzumab, e.g. comprising approximately 600 mg or approximately 1200 mg of pertuzumab combined with approximately 600 mg of trastuzumab, and optionally further comprising 20,000 or 30,000 units of rHuPH20.

The article of manufacture preferably further comprises a package insert. The package insert may provide instructions to administer the FDC to a patient with HER2-expressing, e.g. HER2-positive, HER2-amplified, or HER2-mutated cancer subcutaneously. In certain embodiments, the cancer is breast cancer, ovarian cancer, peritoneal cancer, fallopian tube cancer, lung cancer, prostate cancer, colorectal cancer, biliary cancer and bladder cancer. In other embodiments, the cancer is breast cancer, peritoneal cancer, fallopian tube cancer, lung cancer, colorectal cancer, biliary cancer and bladder cancer. In a particular embodiment, the cancer is breast cancer, such as early breast cancer or metastatic breast cancer.

Another form of an article of manufacture is a syringe, containing the formulation to be administered, which may be attached to a stainless steel hypodermic needle for subcutaneous administration.

Optionally, the subcutaneous administration device comprises a 25G-27G (⅜"-⅝") hypodermic hypodermic injection needle.

Optionally, the volume of the formulation in the subcutaneous administration device is adjusted to 15 mL for the initial or loading dose, and to 10 mL for the subsequent or maintenance doses.

In one embodiment, the article of manufacture comprises two vials, wherein a first vial contains loading dose FDC (e.g. comprising 1200 mg pertuzumab, 600 mg trastuzumab, 30,000 units of rHuPH20, e.g. total volume of about 15 mL), and a second vial contains a maintenance dose FDC (e.g. comprising 600 mg pertuzumab, 600 mg trastuzumab, 30,000 units of rHuPH20, e.g. total volume of about 10 mL).

VII. Deposit of Biological Materials

The following hybridoma cell lines have been deposited with the American Type Culture Collection, 10801 University Boulevard, Manassas, VA 20110-2209, USA (ATCC):

| Antibody Designation | ATCC No. | Deposit Date |
| --- | --- | --- |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

Example 1: Subcutaneous Administration of the FDC of Pertuzumab and Trastuzumab in Combination with Chemotherapy in HER2-Positive Early Breast Cancer (FeDeriCa)

A new subcutaneous formulation, for the first time combining two monoclonal antibodies, pertuzumab and trastuzumab, with recombinant human hyaluronidase in one ready-to-use, fixed-dose combination vial (PH FDC SC), has been developed. Administration of PH FDC SC is less invasive and more rapid compared with two separate intravenous infusions of pertuzumab and trastuzumab (P+H IV; 5-8 min vs 30-90 min per infusion of each antibody). This example reports the primary analysis results from the pivotal phase 3 FeDeriCa study, which was designed to assess the pharmacokinetics, efficacy, and safety of this novel PH FDC SC compared with P+H IV in patients with HER2-positive early breast cancer in the neoadjuvant-adjuvant setting. This study is registered with ClinicalTrials.gov, number NCT03493854.

Methods

FeDeriCa is a randomised, open-label, international, multicentre, two-arm phase 3 non-inferiority study in the neoadjuvant-adjuvant setting. Patients were enrolled at 106 sites in 19 countries. Patients aged 18 years and older, with an Eastern Cooperative Oncology Group performance status of 0 or 1, and HER2-positive, operable, locally advanced, or inflammatory stage II-IIIC breast cancer were randomly assigned (1:1), using a voice- or web-based response system, to receive P IV (840 mg loading dose, 420 mg maintenance dose) plus H IV (8 mg/kg loading dose, 6 mg/kg maintenance dose) or PH FDC SC (1200 mg/600 mg loading dose in 15 mL, 600 mg/600 mg maintenance dose in 10 mL), both administered every 3 weeks in combination with neoadjuvant chemotherapy. Patients were stratified by hormone receptor status (estrogen or progesterone receptor-positive, or oestrogen and progesterone receptor-negative); clinical stage (II-IIIA or IIIB-IIIC); and chemotherapy regimen (4 cycles of dose-dense doxorubicin 60 mg/m$^2$ plus cyclophosphamide 600 mg/m$^2$ every 2 weeks followed by paclitaxel 80 mg/m$^2$ once weekly for 12 weeks, or 4 cycles of doxorubicin 60 mg/m$^2$ plus cyclophosphamide 600 mg/m$^2$ every 3 weeks (AC) followed by 4 cycles of docetaxel 75-100 mg/m$^2$ every 3 weeks). The investigator selected one of the two protocol-approved standard chemotherapy regimens before randomisation. Four cycles of HER2-targeted therapy were administered concurrently with the taxane. After surgery, patients continued the HER2-targeted therapy to receive an additional 14 cycles for a total of 18 cycles. The primary endpoint was non-inferiority of the cycle 7 P serum trough concentration ($C_{trough}$; i.e., cycle 8 pre-dose P concentration) within PH FDC SC versus P IV in the per-protocol pharmacokinetic population. Non-inferiority was concluded if the lower bound of the 90% confidence interval (CI) of the geometric mean ratio was ≥0.8. Enrolment, neoadjuvant therapy, and surgery have been completed; adjuvant treatment and follow-up are ongoing. The trial is registered with ClinicalTrials.gov, number NCT03493854.

Clinical Data 500 patients were randomised: 252 to receive P+H IV and 248 to receive PH FDC SC. The geometric mean ratio P serum $C_{trough}$ SC/serum $C_{trough}$ IV was 1.22 (90% CI 1.14-1.31) with the lower limit of the 90% CI being above the pre-specified non-inferiority margin of 0.8. Total pathological complete response was achieved by 150/252 patients (59.5%, 95% CI 53.18-65.64) in the P+H IV arm and 148/248 patients (59.7%, 95% CI 53.28-65.84) in the PH FDC SC arm. The between-arm difference was 0.15% (95% CI –8.67-8.97). The most common grade 3-4 adverse events occurring during neoadjuvant treatment with HER2-targeted therapy plus chemotherapy in at least 5% of patients were neutropenia (13.5% [34/252] in the P+H IV arm vs 14.1% [35/248] in the PH FDC SC arm), decreased neutrophil count (12.3% [31/252] vs 10.9% [27/248]), febrile neutropenia (5.6% [14/252] vs 6.5% [16/248]), diarrhoea (4.8% [12/252] vs 6.9% [17/248]), and decreased white blood cell count (7.1% [18/252] vs 3.6% [9/248]). At least one treatment-related serious adverse event was reported in 9.9% of patients in the P+H IV arm (25/252) vs 10.5% (26/248) in the PH FDC SC arm. One patient in each treatment arm died; neither death was related to HER2-targeted therapy.

CONCLUSIONS

The study met its primary endpoint: PH FDC SC was non-inferior to P+H IV, based on cycle 7 P serum $C_{trough}$ concentrations. The two regimens produced nearly identical total pathological complete response rates. Safety was comparable between arms, and in line with other P, H, and chemotherapy trials. Overall, PH FDC SC offers a faster, more convenient, and less invasive method of P+H administration for patients with HER2-positive breast cancer.

Methods

Study Design and Participants

FeDeriCa is a randomised, open-label, international, multicentre, two-arm, phase 3 non-inferiority trial conducted at 106 sites in 19 countries.

Eligible patients had HER2-positive EBC and were candidates for preoperative neoadjuvant treatment. Selection criteria were similar to those used in previous P IV+H IV studies: ≥18 years, operable, locally advanced, or inflammatory HER2-positive (immunohistochemistry 3+ or in situ hybridisation-positive) stage II-IIIC BC with a primary tumour >2 cm in diameter, or node-positive disease, an Eastern Cooperative Oncology Group performance status of 0 or 1 and a left ventricular ejection fraction (LVEF) of ≥55% (by echocardiography or multiple-gated acquisition scan). HER2 and hormone receptor status were confirmed centrally. Patients were ineligible if they had received any systemic therapy for treatment or prevention of BC, or radiation treatment for cancer. Patients were also ineligible if they had a serious cardiac condition, impaired liver function, or inadequate renal or bone marrow function.

Randomisation and Masking

Patients were randomly assigned 1:1 in permuted blocks to receive P+H IV or PH FDC SC via central voice- or web-based response system. Stratification factors were hormone receptor status (oestrogen or progesterone receptor-positive, or oestrogen and progesterone receptor-negative); clinical stage (II-IIIA or IIIB-IIIC); and chemotherapy regimen (doxorubicin plus cyclophosphamide every 2 weeks (ddAC)→paclitaxel every week, or AC every 3 weeks→docetaxel every 3 weeks).

Procedures

Figure 6A:
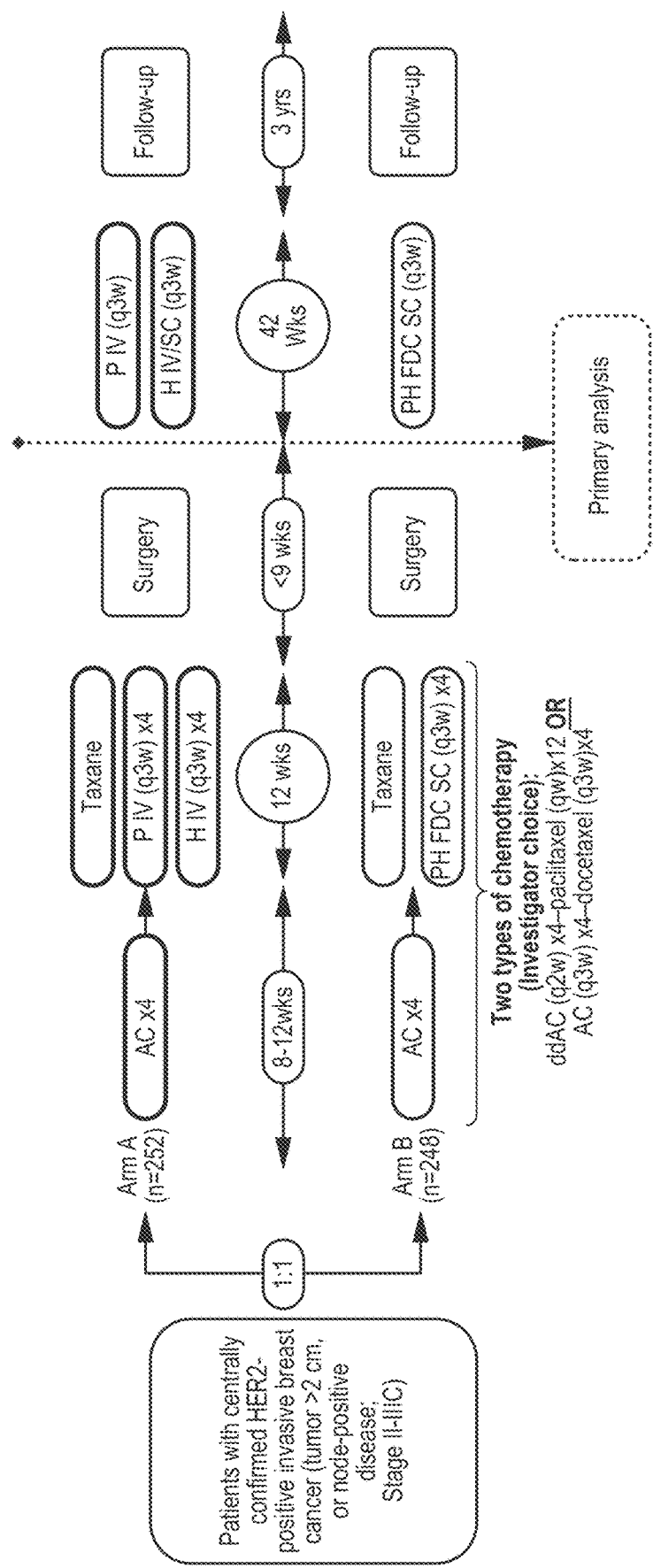
FIG. 6A shows the study design for the FeDeriCa study. Randomisation was stratified by hormone receptor status, stage at presentation and type of chemotherapy. Abbreviations: (dd)AC=(dose-dense) doxorubicin+cyclophosphamide. FDC=fixed-dose combination. FPI=first patient in. H=trastuzumab. IV=intravenous. LPI=last patient in. P=pertuzumab. qw=every week. q2w=every 2 weeks. q3w=every 3 weeks. SC=subcutaneous. Study dosing: PH FDC SC q3w: 1200 mg P SC/600 mg H SC loading dose in 15 mL, 600 mg each maintenance in 10 mL; P IV q3w: 840 mg loading dose, 420 mg maintenance; H IV q3w: 8 mg/kg loading dose, 6 mg/kg maintenance; H SC q3w: 600 mg; ddAC q2w: 60 mg/m² A/600 mg/m² C; paclitaxel qw: 80 mg/m²; docetaxel q3w: 75 mg/m², escalating to 100 mg/m² if tolerated; AC q3w: same dose as ddAC.

Patients received 8 neoadjuvant chemotherapy cycles, comprising 4 ddAC cycles (doxorubicin 60 mg/m² plus cyclophosphamide 600 mg/m² every 2 weeks, with granulocyte colony-stimulating factor as needed, per local guidelines)→paclitaxel 80 mg/m² once weekly for 12 weeks, or 4 AC cycles (doxorubicin 60 mg/m² plus cyclophosphamide 600 mg/m² every 3 weeks)→4 docetaxel cycles 75-100 mg/m² every 3 weeks (FIG. 6A). The choice between chemotherapy regimen options was at the investigator's discretion before randomisation. Four P+H IV or PH FDC SC cycles were administered at 3-week intervals concurrently with the taxane component of either regimen. After completion of the neoadjuvant regimen, patients underwent surgery, followed by a further 14 P+H IV/H SC or PH FDC SC cycles (maximum total of 18). Treatment was to be discontinued in cases of investigator-assessed radiographic or clinical disease progression or recurrence or unmanageable toxicity.

Figure 6B:
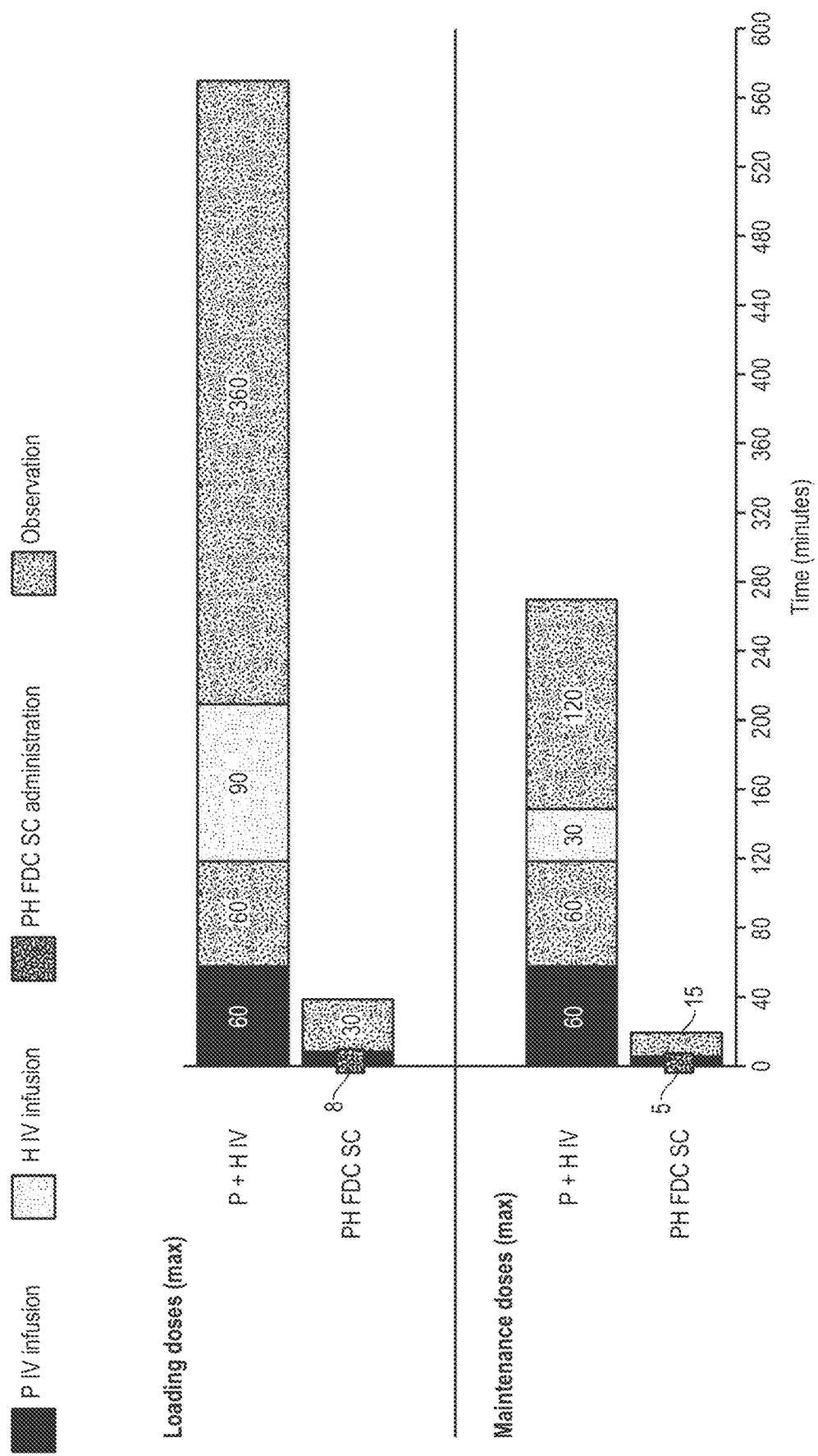
FIG. 6B shows the infusion, administration and observation times for the FeDeriCa study.

For patients randomised to P+H IV, P was administered as an initial 840 mg loading dose→420 mg maintenance doses every 3 weeks. H IV was administered as an initial 8 mg/kg loading→6 mg/kg maintenance doses every 3 weeks. mAb administration order per investigator preference. Chemotherapy was given after HER2-targeted treatment on the same day. For patients randomised to PH FDC SC, the FDC was administered as an initial 1200 mg/600 mg loading dose of P/H in 15 mL→600 mg/600 mg maintenance doses of P/H in 10 mL every 3 weeks. The loading dose was selected based on approximate dose proportionality of data in BO30185.[24] The PH FDC SC contained 2000 U/mL recombinant human hyaluronidase (rHuPH20). SC injections were administered in the thigh with a hand-held syringe at a rate of mL/min over 8 min (loading) and 5 min (maintenance) followed by a 30 min observation period after the first dose and, if well tolerated, 15 min after subsequent doses (FIG. 6B).

Dose modifications of HER2-targeted therapy were not permitted. Patients were withdrawn from all study treatment if HER2-targeted therapy was withheld for >2 cycles (>9 weeks between doses) or needed to be permanently discontinued for treatment-related toxicity. Patients who discontinued chemotherapy due to toxicity were not automatically withdrawn from study treatment. In such events, surgery could be brought forward and the assigned HER2-targeted therapy was to be completed up to a maximum of 18 cycles in total, per the schedule.

Figure 8:
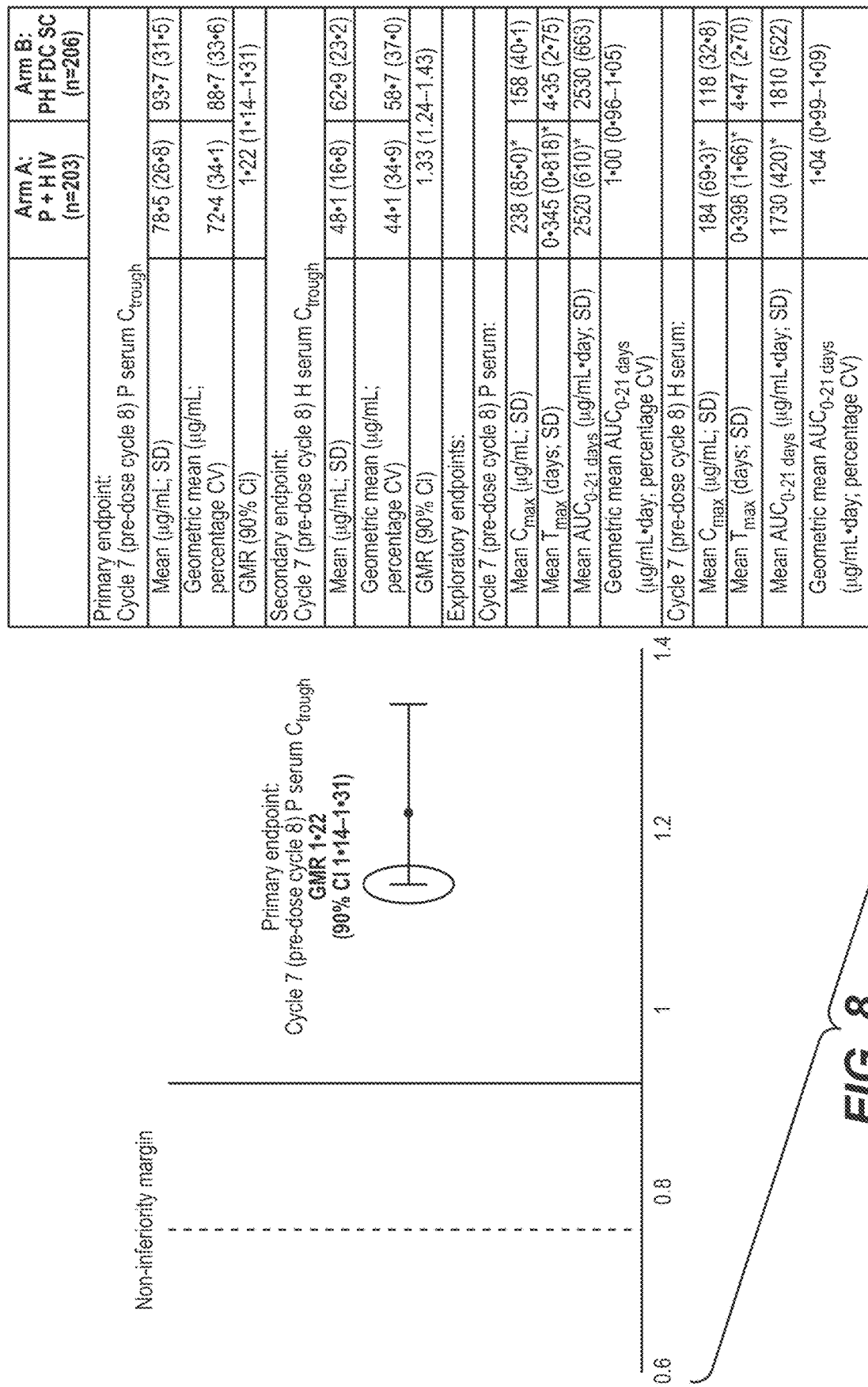
FIG. 8 shows the pharmacokinetic parameters in the per-protocol pharmacokinetic population for FeDeriCa (*n=202). $AUC_{0-21\ days}$=area under the serum concentration-time curve from 0-21 days. CI=confidence interval. $C_{max}$=maximum serum concentration; $C_{trough}$=serum trough concentration. CV=coefficient of variation. GMR=geometric mean ratio. H=trastuzumab. P=pertuzumab. P+H IV=intravenous pertuzumab and trastuzumab. PH FDC SC=subcutaneous pertuzumab and trastuzumab fixed-dose combination. SD=standard deviation. $T_{max}$=time to $C_{max}$.

Blood samples for PK assessments were collected prior to IV infusion/SC injection of HER2-targeted therapy, and after administration, at times indicated in FIG. 8. Exact collection times were recorded for PK samples.

Outcomes

The primary objective was non-inferiority of the cycle 7 (ie, pre-dose cycle 8) P serum $C_{trough}$ within PH FDC SC, versus P IV. Non-inferiority of cycle 7 H serum $C_{trough}$ within PH FDC SC, versus H IV (tested hierarchically with the primary endpoint to adjust for multiple statistical testing) was a secondary endpoint. Key exploratory PK endpoints included maximum serum concentration ($C_{max}$) of P and H, time to $C_{max}$ ($T_{max}$), and AUC from 0-21 days ($AUC_{0-21\ days}$).

Concerning efficacy, the main endpoint was total pCR (tpCR; eradication of invasive disease in the breast and axilla per local pathologist assessment [tpCR; ypT0/is, ypN0]). Additional secondary efficacy endpoints include: IDFS (time from the first date of no disease [ie, the date of primary surgery] to the first occurrence of invasive disease or death from any cause), IDFS including second primary non-BC (defined in the same way as IDFS but including second primary non-breast invasive cancer as an event [with the exception of non-melanoma skin cancers and in situ carcinoma of any site]), event-free survival (time from enrolment to the first occurrence of BC progression, recurrence, or death from any cause), event-free survival including second primary non-BC, distant recurrence free interval (time between surgery and the date of distant BC recurrence), and overall survival (time from randomisation to death from any cause). Time-to-event endpoints will be reported at a later date once data are mature. Clinical response (complete/partial), assessed locally by clinical examination or mammography, was an exploratory efficacy endpoint.

Concerning safety, incidence and severity of adverse events (AEs), serious AEs, and laboratory test abnormalities determined according to National Cancer Institute Common Terminology—Criteria for Adverse Events (NCI-CTCAE) v4 were assessed. Primary cardiac safety endpoints were defined as incidence of symptomatic ejection fraction decreases ("heart failure") of New York Heart Association (NYHA) Class III or IV and a drop in LVEF of ≥10 percentage points from baseline and to an absolute value of <50%, and cardiac death. The incidence of asymptomatic or mildly symptomatic left ventricular systolic dysfunction (NYHA Class II heart failure) defined as a decrease in LVEF of ≥10 percentage points to an absolute LVEF of <50%, confirmed by a second assessment, was also reported as a secondary cardiac endpoint.

Samples were collected for detection of anti-drug antibodies (ADAs) to pertuzumab, trastuzumab, and anti-rHuPH20 (in the PH FDC SC arm) at baseline, during treatment, and during the post-treatment follow-up phase. ADAs to pertuzumab and trastuzumab were detected in serum samples using validated enzyme-linked immunosorbent assays. Anti-rHuPH20 antibodies were detected in plasma samples using a validated electrochemiluminescent assay. All immunogenicity samples were analysed in a central laboratory. Associations between ADAs and tpCR and safety were assessed in an exploratory manner.

Statistical Analysis

The primary analysis was conducted when all patients completed neoadjuvant therapy and underwent surgery (unless prematurely withdrawn). The primary PK analysis was done in the per protocol PK (PPP) population, which included all enrolled patients who adhered to pre-specified criteria for PK assessment (patients were excluded if they were missing the cycle 7 $C_{trough}$ (ie, pre-dose cycle 8) PK sample, had a $C_{trough}$ sample collected with ≥2 days deviation from the planned date on Day 21 (ie, before Day 19 or after Day 23), were given a dose amount that deviated from the planned dose by >20% within 3 cycles (from cycle 5), had a dose delay of >7 days, an SC injection not in the thigh, cycle 8 pre-dose and post-dose samples switched in the P+H IV arm, or if there was an assay error impacting $C_{trough}$ measurement). Efficacy analyses were performed on the intention-to-treat (ITT) population, which comprised all randomised patients. The safety population included all patients who received ≥1 dose of study medication, including chemotherapy or HER2-targeted therapy.

The study was designed to have ≥80% power to demonstrate non-inferiority of the cycle 7 serum $C_{trough}$ of P when administered as part of PH FDC SC versus P as part of P+H IV. Assuming a coefficient of variation (CV) of 60% for P serum $C_{trough}$, based on previous studies, a minimum of 130 patients per study arm were needed to demonstrate non-inferiority if the true means of the two formulations did not differ by >5%. An additional 240 patients were to be recruited to provide a substantial database to assess tpCR and the safety profile. Thus, the overall planned enrolment was 500 patients.

For the primary PK endpoint, non-inferiority was assessed by a one-sided testing procedure. Non-inferiority was concluded if the lower bound of the two-sided 90% CI of the observed geometric mean ratio (GMR) of the cycle 7 P serum $C_{trough}$ subcutaneous/$C_{trough}$ intravenous was ≥0.8.

The non-inferiority of the SC and IV doses of trastuzumab was assessed using the same criteria as for the primary analysis and was tested in a hierarchical procedure to control the type I error rate at a one-sided significance level of 5%. Thus, H pre-dose cycle 7 serum $C_{trough}$ SC/serum $C_{trough}$ IV was only tested if non-inferiority was concluded for the primary endpoint.

Efficacy endpoints were analysed descriptively. tpCR rates in each arm, between-group differences and corresponding 95% Hauck-Anderson CIs were calculated. The lower bound of the CI was used to reflect the largest tpCR difference that could be considered unlikely.

As part of an exploratory analysis, a multiple logistic regression analysis of tpCR, adjusting for the stratification factors and selected baseline characteristics (age, race, menopausal status, and weight), was conducted to investigate whether the results were still consistent with the unadjusted result.

Statistical analyses were performed with SAS software (version 9.4).

Results

Figure 7:
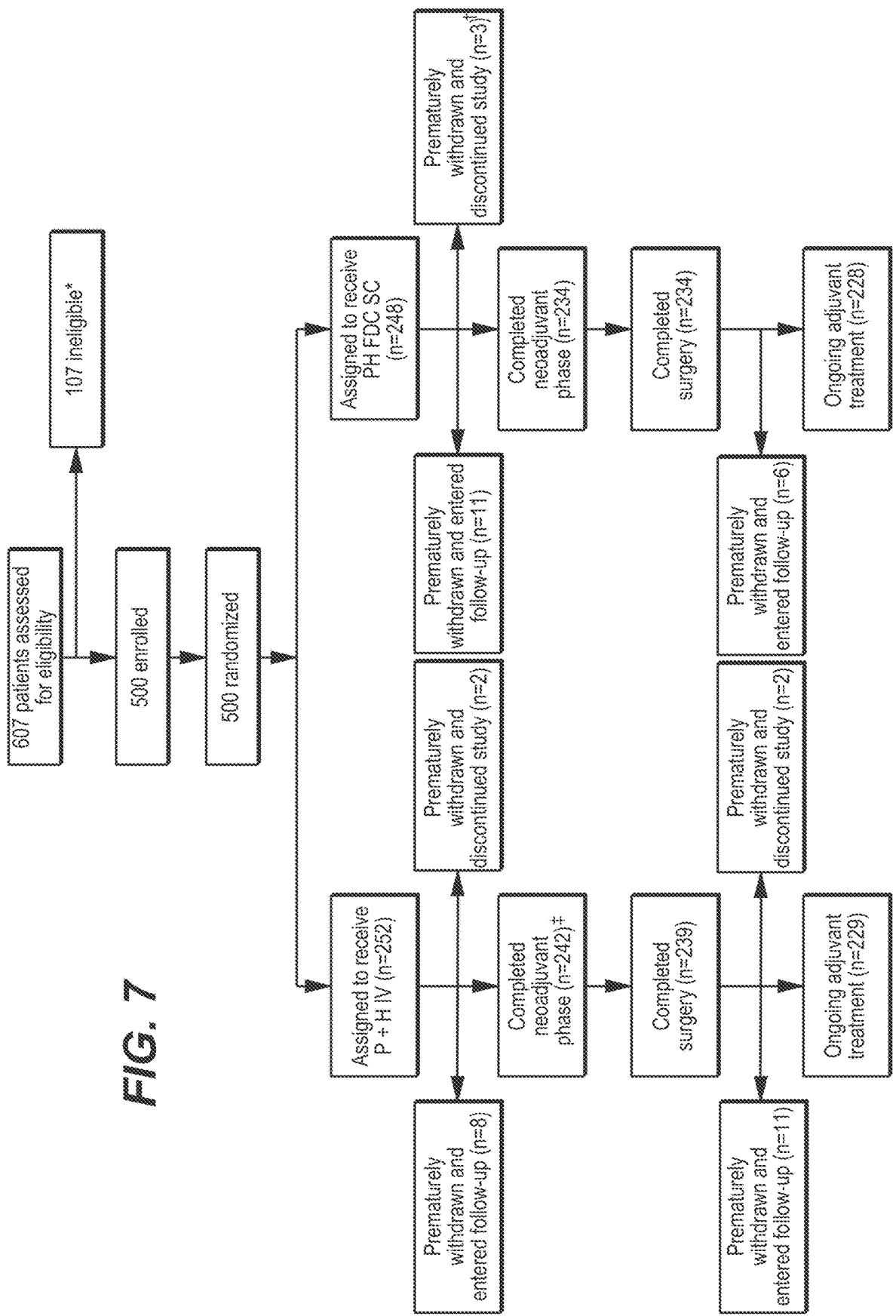
FIG. 7 shows the FeDeriCa study trial profile. *Reasons for exclusion between screening and randomisation: HER2-negative by central laboratory (n=46); non-stage II-IIIC early disease/no needle core biopsy for inflammatory disease (n=1); no formalin-fixed, paraffin-embedded tumour tissue block (n=1); inadequate liver function (n=6); no signed consent (n=16); metastatic disease (n=16); inability to comply to protocol (n=5); sentinel lymph node biopsy prior to neoadjuvant therapy (n=1); received previous systemic therapy/radiotherapy for breast cancer (n=2); active liver disease (n=2); primary tumour ≤2 cm or node-negative (n=1); pregnancy (n=1); serious cardiac illness or medical condition (n=2); major surgical procedure within 28 days prior to randomisation/major surgery expected during the course of the study (n=1); bilateral breast cancer (n=2); inadequate bone marrow function (n=1); baseline left ventricular ejection fraction <55% (n=2); history of ventricular dysrhythmias or risk factors for ventricular dysrhythmias (n=1). Includes one patient who died. Three patients discontinued the study prior to undergoing surgery.

Five hundred patients were enrolled. At clinical cut-off, enrolment was complete, all patients had completed neoadjuvant treatment, had undergone surgery, and had started adjuvant therapy, but none had completed follow-up (FIG. 7).

Baseline demographic and tumour characteristics were generally well balanced in the ITT (Table 1) and PPP populations. In both arms, ~48% of patients received ddAC→paclitaxel and ~52% received AC→docetaxel.

In both arms, over 98% of patients completed the assigned anthracycline regimen, ~90%-95% completed the assigned taxane regimen, and ~97% completed the four scheduled cycles of HER2-targeted treatment during the neoadjuvant period.

The dose intensity exceeded 98.0% for all drugs in each regimen. Most patients did not experience delays or require dose modifications for chemotherapy (~60-94%), or for experience delays to anti-HER2 therapy (~71-74%). A total of 473 patients (239 in the P+H IV arm and 234 in the PH FDC SC arm) had a cycle 7 PK measurement. Sixty-four patients (36 in the P+H IV arm and 28 in the PH FDC SC arm) were excluded from the primary PK analysis for violations of the protocol; thus, the PPP population comprised 409 patients (203 in the P+H IV arm and 206 in the PH FDC SC arm). The GMR of cycle 7 serum P $C_{trough}$ was 1.22 (90% CI 1.14-1.31) (FIG. 8). The GMR of cycle 7 serum H $C_{trough}$ was 1.33 (90% CI 1.24-1.43) (FIG. 8). The observed lower limits of the two-sided 90% CIs were above the pre-specified non-inferiority margin of 0.8.

Figure 9:
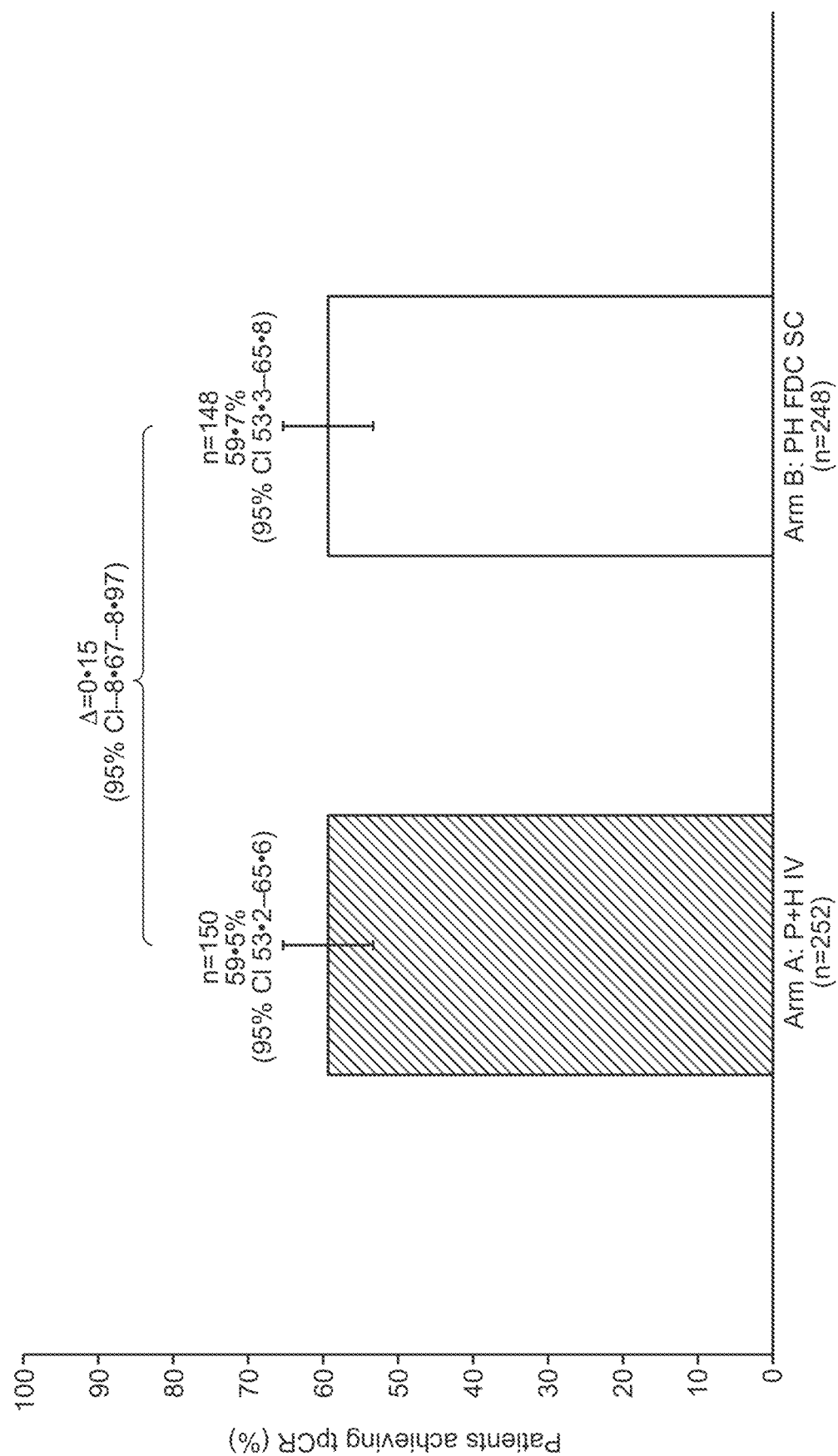
FIG. 9 shows the total pathological complete response (pCR) in the intention-to-treat population for FeDeriCa. CI=confidence interval. P+H IV=intravenous pertuzumab and trastuzumab. PH FDC SC=subcutaneous pertuzumab and trastuzumab fixed-dose combination. tpCR=total pathological complete response.
Figure 10:
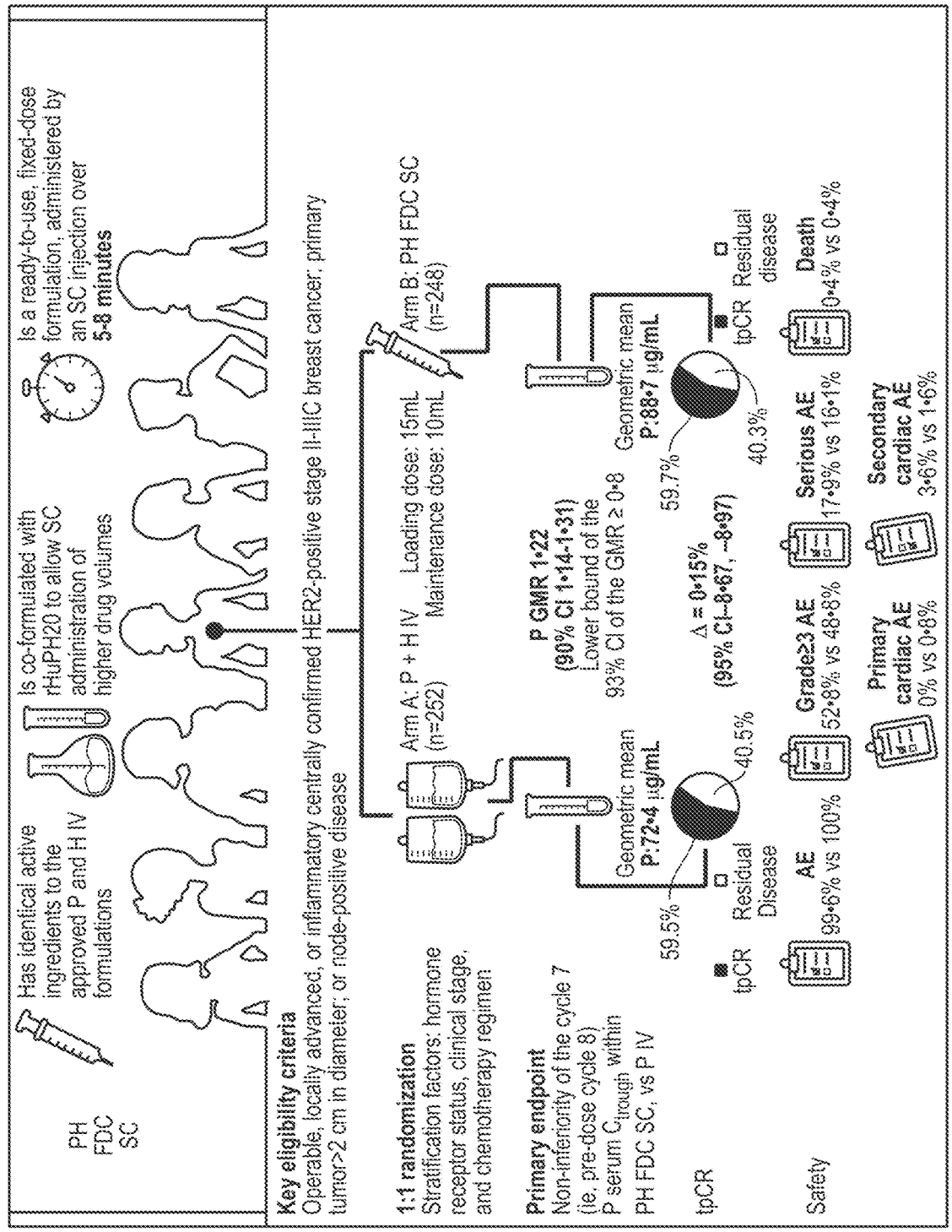
FIG. 10 provides a visual abstract of the FeDeriCa study.
Figure 11:
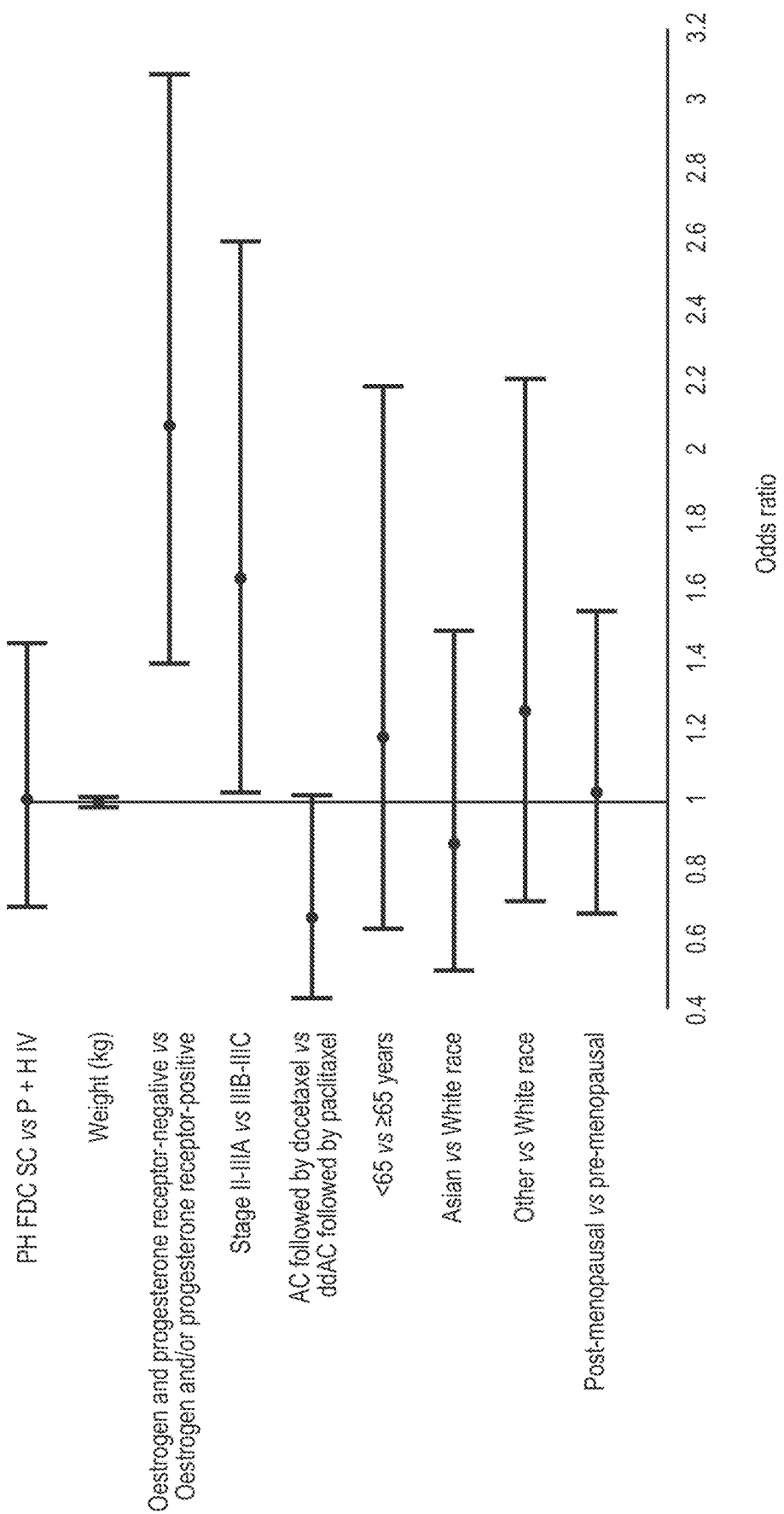
FIG. 11 depicts the Odds ratios and 95% Wald confidence limits for the exploratory multiple logistic regression analysis of total pCR in the intention-to-treat population for FeDeriCa.

P and H exposure, as shown by values for serum $AUC_{0-21\ days}$, was similar in both arms. Serum P $AUC_{0-21\ days}$ GMR was 1.00 (90% CI 0.96-1.05) and H $AUC_{0-21\ days}$ GMR was 1.04 (90% CI 0.99-1.09) (FIG. 8). Mean cycle 7 P and H $C_{max}$ was higher for P+H IV compared with PH FDC SC (FIG. 8).

tpCR was achieved by 150/252 patients (59.5%, 95% CI 53.2-65.6) in the P+H IV arm and 148/248 patients (59.7%, 95% CI 53.3-65.8) in the PH FDC SC arm (FIG. 9). The between-arm difference was 0.15% (95% CI −8.67-8.97).

Figure 13:
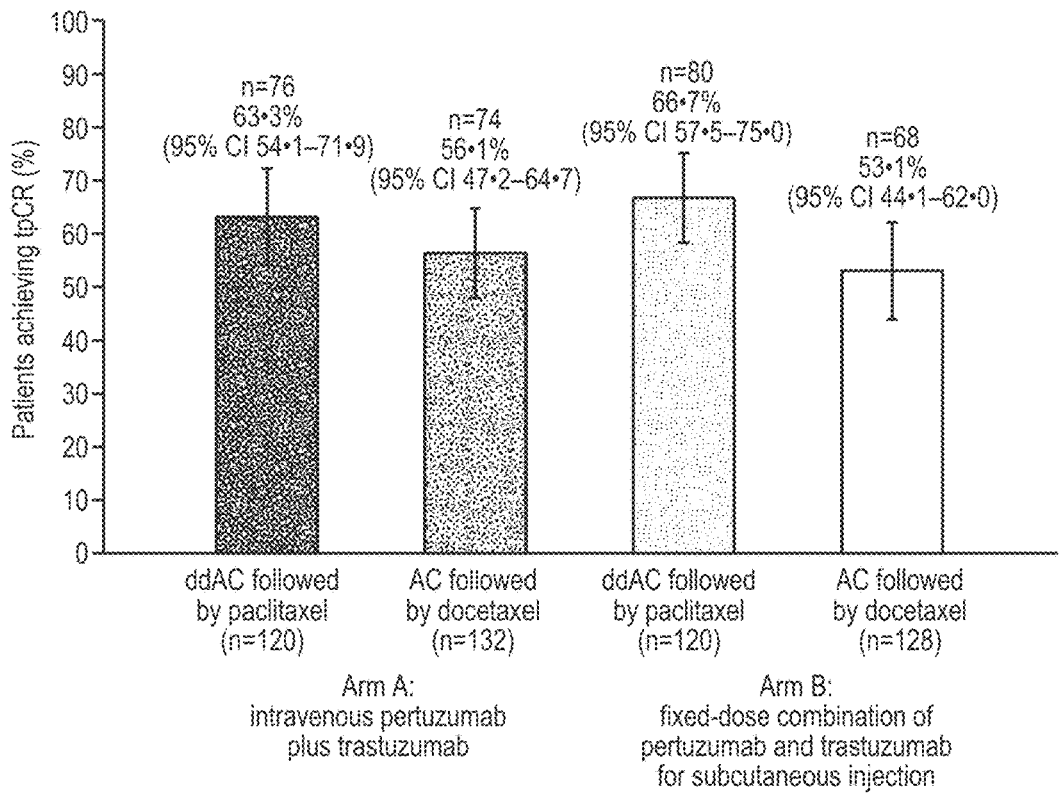
FIG. 13 depicts total pathological complete response (pCR) for FeDeriCa based on chemotherapy type. CI=confidence interval. (dd)AC=(dose-dense) doxorubicin+cyclophosphamide.
Figure 14:
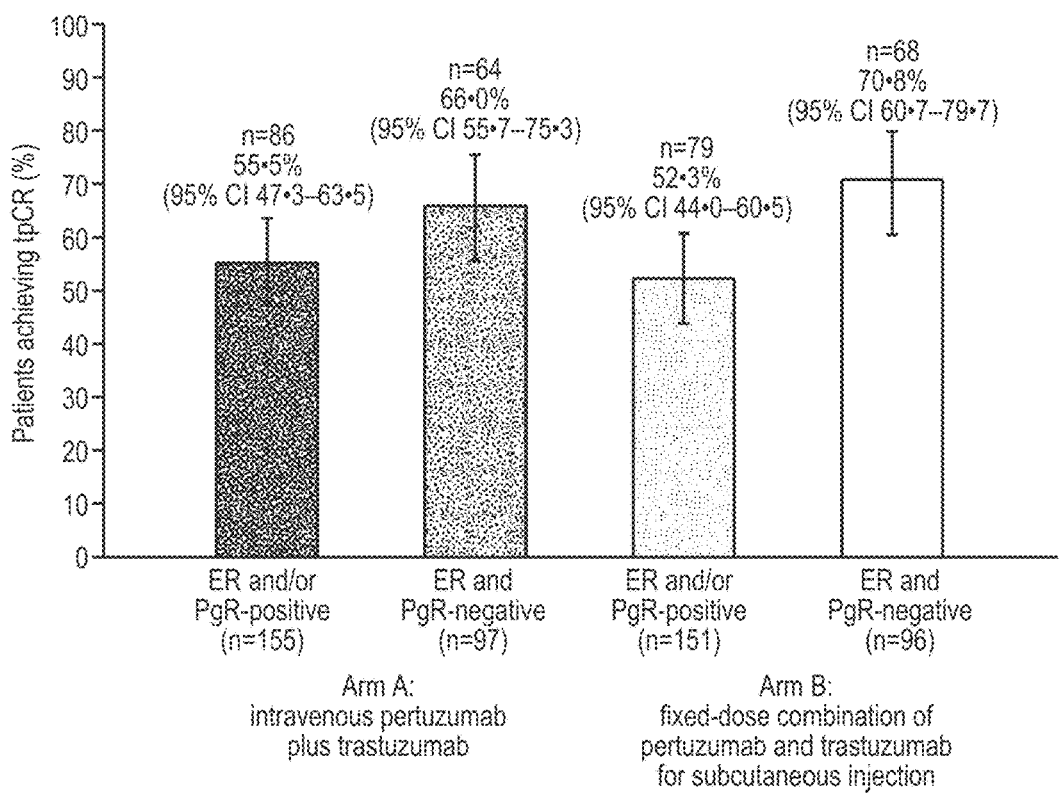
FIG. 14 depicts total (pCR) for FeDeriCa based on hormone receptor status. ER=estrogen receptor. PgR=progesterone receptor.

Total pCR in patient subgroups in the intention-to-treat population is shown in FIGS. 13-14 and Table 4. In both arms, the total pCR rate was higher in patients who had: hormone receptor-negative disease; stage II-IIIA disease; or received ddAC→paclitaxel (FIGS. 13-14 and Table 4). Recent studies have reported no increased benefit of adjuvant ddAC in HER2-positive disease with trastuzumab;[31,32] however, patients who received ddAC followed by paclitaxel appeared to have numerically greater total pCR rates in FeDeriCa than those who received AC followed by docetaxel. In this study, the chemotherapy choice seemed to be dependent upon the region (eg, the higher ddAC numbers were in Asia). The differences in total pCR between chemotherapy type are most likely a chance finding. Additional analyses (not shown) were conducted to assess total pCR in Asian patients, where 48.1% achieved pCR in the intravenous arm and 60.8% achieved total pCR in the subcutaneous arm. No reason was found to explain this difference based on biological or pharmacokinetic parameters.

Clinical response rates were 85.3% (215/252) in the intravenous arm and 83.1% (206/248) in the subcutaneous arm.

Multiple logistic regression analysis results shown in Table 5 agreed with unadjusted analyses and showed no effect of body weight on tpCR.

A safety overview is given in Table 2; the numbers of patients experiencing AEs by grade, in FIGS. 15A-D. Almost all patients experienced an AE, which were related to chemotherapy in 97.2% (245/252) and 99.2% (246/248) of cases in the P+H IV and PH FDC SC arms, respectively, and to HER2-targeted therapy in 65.9% (166/252) and 66.1% (164/248), respectively (Table 2).

The most common AEs (any grade, >30% of patients) were alopecia (70.2% [177/252] in the P+H IV arm vs 77.0% [191/248] in the PH FDC SC arm), nausea (60.3% [152/252] vs 58.9% [146/248]), diarrhoea (55.2% [139/252] vs 58.5% [145/248]; the majority of diarrhoea events were low grade and occurred during the first cycle of HER2-targeted treatment), and anaemia (40.9% [103/252] vs 33.9% [84/248]) (Table 2). The most common HER2-targeted treatment-related AE (any grade, >30% of patients) was diarrhoea (32.5% [82/252] vs 30.6% [76/248], respectively). Systemic injection-/infusion-related reactions related to and occurring within 24 hours of HER2-targeted treatment were reported in 10.3% (26/252) of patients in the P+H IV arm vs 1.2% (3/248) in the PH FDC SC arm, most of which were grade 1 or 2 (24/26 vs 3/3). The incidence of systemic reactions within 24 hours was highest after the first administration of HER2-targeted treatment and incidence decreased in subsequent administrations.

Within the AE category "infusion-related and administration-related reactions occurring within 24 hours", 0/252 patients in the P+H IV arm reported injection site reactions versus 12.9% (32/248) in the PH FDC SC arm. All were grade 1 or 2 (29/32 and 3/32, respectively), with injection site pain and erythema as the most common symptom.

The most common grade 3-4 AEs were neutropenia (13.5% [34/252] in the P+H IV arm vs 14.1% [35/248] in the PH FDC SC arm), decreased neutrophil count (12.3% [31/252] vs 10.9% [27/248]), febrile neutropenia (5.6% [14/252] vs 6.5% [16/248]), diarrhoea (4.8% [12/252] vs 6.9% [17/248]), and decreased white blood cell count (7.1% [18/252] vs 3.6% [9/248]). The most common HER2-targeted treatment-related grade 3-4 AE was diarrhoea (2.0% [5/252] vs 3.6% [9/248], respectively).

The most common serious AEs were febrile neutropenia (4.0% [10/252] in the P+H IV arm vs 3.6% [9/248] in the PH FDC SC arm), pyrexia (1.6% [4/252] vs 0.8% [2/248]), neutropenic sepsis (0.4% [1/252] vs 1.2% [3/248]), neutropenia (1.2% [3/252] vs 0.4% [1/248]), decreased neutrophil count (0.4% [1/252] vs 1.2% [3/248]), and cardiac failure (0.8% [2/248] vs 0.8% [2/248]).

One patient in each arm experienced AE that led to death (urosepsis in the P+H IV arm; acute myocardial infarction in the PH FDC SC arm). Neither death was considered to be related to HER2-targeted therapy, as both occurred prior to the start of HER2-targeted therapy, in the PH FDC SC arm.

Two of 248 patients (0.8%) in the PH FDC SC arm experienced primary cardiac events: one heart failure (resolved by clinical cut-off), and one cardiac death (prior to the start of HER2-targeted therapy, not related to PH FDC SC) (Table 2). Secondary cardiac events were reported in 0.8% of patients (2 of 252) in the P+H IV arm and in 0.4% of patients (1 of 248) in the PH FDC SC arm.

LVEF was evaluated in all patients at baseline and in 494 patients (98.8%) post-baseline. The mean change from baseline to worst LVEF value was −5.50% (standard deviation 5.74) in the P+H IV arm and −5.17% (standard deviation 5.56) in the PH FDC SC arm (mean difference 0.33%; 95% CI −0.7-1.3). Seven patients (2.8%) in the P+H IV arm and five (2.0%) in the PH FDC SC arm experienced at least one significant LVEF drop (of at least 10 ejection fraction points from baseline and to below 50%).

The overall incidence of treatment-emergent ADAs was <5% in each arm (Table 6). Exploratory analyses did not suggest that the presence of ADAs had an adverse effect on tpCR rates or safety (injection-/infusion-related reactions or administration-related reactions) at clinical cut-off.

DISCUSSION

The FeDeriCa primary analysis demonstrated that PH FDC SC was non-inferior to P+H IV, based on cycle 7 P and H serum $C_{trough}$ concentrations.

The P and H cycle 7 $C_{trough}$ of IV PH FDC SC was higher than P+H, with the H $C_{trough}$ GMR very similar to that reported in the HannaH study.[9] The overall exposure on the basis of AUC was comparable between PH FDC SC and P+H IV.

All patients in the PH FDC SC arm showed $C_{trough}$ concentrations above the therapeutic target threshold of 20 µg/ml, which is the effective concentration identified from nonclinical mouse xenograft models and early clinical response data,[25] suggesting that the fixed dose was appropriate and ensured adequate receptor saturation.

Efficacy analyses demonstrated that PH FDC SC was comparable to P+H IV in terms of tpCR, with subgroup analyses consistent with the main efficacy results. In particular, there was no discernible association between body weight and tpCR rates. Multiple logistic regression analyses were in line with the corresponding unadjusted results. In addition, tpCR rates were consistent with the results from other trials with P+H IV in patients with HER2-positive BC, where P+H IV was given in combination with an anthracycline/taxane-based regimen before surgery with rates of tpCR ranging from 54% to 64%.[26-29]

Approximately half of patients in each arm experienced grade 3-5 AEs and this did not result in premature withdrawal from HER2-targeted therapy, as evidenced by the high number of patients who completed neoadjuvant treatment at the time of clinical cut-off (which itself indicates good tolerability).

The overall safety profile of PH FDC SC was comparable to that of P+H IV, with the exception of AEs associated with the different routes of administration (ie, injection site reactions). No new or unexpected toxicities were observed. As expected, the most common grade 3-4 AEs with PH FDC SC were neutropenia, decreased neutrophil count, febrile neutropenia, diarrhoea, and decreased white blood cell count. Diarrhoea rarely led to discontinuation. Local injection site reactions reported in the PH FDC SC arm were infrequent and all low grade, and rates are in line with injection site reactions reported with H SC.[9] In contrast, systemic infusion-related reactions were more frequent in the P+H IV arm. This numerical difference may be attributable to differences in systemic absorption and the low $C_{max}$ associated with SC administration (the mean cycle 7 $C_{max}$ for P and H in the PH FDC SC arm were lower than in the P+H IV arm).

The incidence of primary and secondary cardiac events was low in both arms with no meaningful difference, and consistent with rates reported in previous studies with similar chemotherapy regimens.[26] The extent and proportion of patients with changes in LVEF were also similar in the two arms. The only cardiac death was reported in the PH FDC SC arm, although it occurred during treatment with anthracyclines and before the start of the HER2-targeted therapy. None of the fatal events were related to HER2 treatment.

Immunogenicity analyses showed that the incidence of ADAs in the PH FDC SC arm was low, comparable to the P+H IV arm, and did not appear to have any adverse clinical consequences with respect to PK, efficacy, and safety.

Overall, the efficacy and safety data for PH FDC SC in combination with chemotherapy from this study were consistent with the known efficacy and safety profile of P+H in combination with chemotherapy in patients with HER2-positive BC.[26-29]

The current analysis has limitations. The primary analysis was conducted after completion of the neoadjuvant phase; however, HER2-targeted treatment is continuing up to 18 cycles, as per standard of care. Therefore, safety, efficacy, and PK results from the adjuvant phase and 3-year end of follow-up results are not yet available. However, the long-term safety and efficacy profile of PH FDC SC in FeDeriCa is expected to be comparable to that of P+H IV.

No chemotherapy is administered in the adjuvant setting in FeDeriCa; hence, safety is not expected to worsen during longer follow-up based on the large body of evidence regarding the pattern and incidence of AEs, which are most frequently reported when P+H IV is given concomitantly with chemotherapy. Long-term efficacy results of the HannaH study support the established non-inferiority of H SC versus H IV, and the safety profile remained consistent with that associated with IV administration over time.[11] In addition, the final results from the MetaPHER study (a phase 3 single-arm study assessing the safety of H SC in combination with P IV and docetaxel in patients with previously untreated advanced BC) demonstrated that the safety, including long-term safety, of this regimen was comparable to historical data from P+H IV and docetaxel in patients with HER2-positive advanced BC.[19] At a follow-up of 26.7 months (max. 45 months), no cumulative toxicity or late cardiac safety issues were observed with H SC.

In conclusion, PH FDC SC was non-inferior to P+H IV based on cycle 7 P and H serum $C_{trough}$ concentrations. The two regimens produced nearly identical tpCR rates and had comparable safety profiles, including cardiac safety. The shorter duration of administration of PH FDC SC compared with P+H IV has the potential to provide substantial time-saving for patients, physicians, nurses, and pharmacy staff. Based on the positive experience with H SC home administration, PH FDC SC also has the potential to be administered at home in the future.[30]

PH FDC SC offers a faster, more convenient, and less invasive method of P+H administration for HER2-positive BC, potentially freeing up resources and increasing capacity in healthcare systems.

P IV and H IV can be given in any order. The 15-minute PH FDC SC maintenance dose observation period assumes that the loading dose injection was well tolerated; patients could be observed for longer at the discretion of the investigator, per local requirements.

TABLE 1

Baseline patient demographic and tumor characteristics for the intention-to-treat population

|  | Arm A: P + H IV (n = 252) | Arm B: PH FDC SC (n = 248) |
|---|---|---|
| Age, years | 49.0 (42.0-58.0) | 52.0 (44.0-58.5) |
| Body weight, kg | 66.0 (57.0-76.6) | 65.0 (58.0-77.1) |
| Ethnic origin | | |
| White | 164 (65.1%) | 165 (66.5%) |
| Asian | 54 (21.4%) | 51 (20.6%) |
| Black or African American | 3 (1.2%) | 3 (1.2%) |
| Unknown/other | 31 (12.3%) | 29 (11.7%) |
| ECOG performance status | | |
| 0 | 235 (93.3%) | 227 (91.5%) |
| 1 | 16 (6.3%) | 19 (7.7%) |
| Unknown | 1 (0.4%) | 2 (0.8%) |
| Menopausal status | | |
| Premenopausal | 144 (57.1%) | 118 (47.6%) |
| Postmenopausal | 106 (42.1%) | 130 (52.4%) |
| Unknown | 2 (0.8%) | 0 |
| Histological subtype | | |
| Invasive carcinoma NST | 194 (77.0%) | 197 (79.4%) |
| Invasive lobular carcinoma | 16 (6.3%) | 13 (5.2%) |
| Invasive micropapillary carcinoma | 2 (0.8%) | 1 (0.4%) |
| Mucinous carcinoma | 3 (1.2%) | 2 (0.8%) |
| Apocrine carcinoma | 3 (1.2%) | 2 (0.8%) |
| Other | 34 (13.5%) | 33 (13.3%) |
| Histological grade | | |
| GX | 2 (0.8%) | 4 (1.6%) |
| G1 | 9 (3.6%) | 3 (1.2%) |
| G2 | 119 (47.2%) | 116 (46.8%) |
| G3 | 80 (31.7%) | 90 (36.3%) |
| Unknown | 42 (16.7%) | 35 (14.1%) |
| Hormone receptor status* | | |
| Estrogen and progesterone receptor-negative | 97 (38.5%) | 96 (38.7%) |
| Estrogen or progesterone receptor-positive | 155 (61.5%) | 151 (60.9%) |
| Estrogen or progesterone receptor status unknown | 0 | 1 (0.4%) |
| HER2 immunohistochemistry | | |
| 0 | 3 (1.2%) | 0 |
| 1+ | 6 (2.4%) | 2 (0.8%) |
| 2+ | 68 (27.0%) | 74 (29.8%) |
| 3+ | 175 (69.4%) | 170 (68.5%) |
| Unknown | 0 | 2 (0.8%) |
| HER2 in situ hybridisation* | | |
| Positive | 252 (100%) | 247 (99.6%) |
| Negative | 0 | 1 (0.4%)[†] |
| Clinical stage at presentation | | |
| II-IIIA | 202 (80.2%) | 196 (79.0%) |
| IIIB-IIIC | 50 (19.8%) | 52 (21.0%) |

Data are median (IQR) or number (%).
*Determined by a central laboratory.
ECOG = Eastern Cooperative Oncology Group. IQR = interquartile range. NST = no special type. P + H IV = intravenous pertuzumab and trastuzumab. PH FDC SC = subcutaneous pertuzumab and trastuzumab fixed-dose combination.

TABLE 2

Safety overview (safety population)

|  | Arm A: P + H IV (n = 252) | Arm B: PH FDC SC (n = 248) |
|---|---|---|
| Patients with ≥1 adverse event (any grade) | 251 (99.6%) | 248 (100%) |
| Related to any study drug | 245 (97.2%) | 247 (99.6%) |
| Related to HER2-targeted therapy | 166 (65.9%) | 164 (66.1%) |
| Related to any chemotherapy drug | 245 (97.2%) | 246 (99.2%) |
| Patients with ≥1 adverse event (grade 3-5) | 133 (52.8%) | 121 (48.8%) |
| Patients with ≥1 serious adverse event | 45 (17.9%) | 40 (16.1%) |
| Related to any study drug | 25 (9.9%) | 26 (10.5%) |
| Patients with adverse events leading to death | 1 (0.4%)* | 1 (0.4%)[†] |
| Primary cardiac event | 0 | 2 (0.8%) |
| Heart failure (NYHA Class III/IV) and significant LVEF decline | 0 | 1 (0.4%)[‡] |
| Definite or probable cardiac death | 0 | 1 (0.4%)[†§] |
| Secondary cardiac event | 9 (3.6%) | 4 (1.6%) |
| Identified by initial LVEF assessment | 9 (3.6%) | 4 (1.6%) |
| Confirmed by second LVEF assessment | 2 (0.8%) | 1 (0.4%) |

Data are number of patients (%).
*Urosepsis.
[†]Acute myocardial infarction.
[‡]Decline in LVEF of ≥10 percentage points from baseline and to an absolute value <50%. The event resolved.
[§]Not related to HER2 treatment: The event occurred after cycle 2; hence, occurred prior to the start of anti-HER2 treatment with PH FDC SC.
LVEF = left ventricular ejection fraction. NCI-CTCAE = National Cancer Institute - Common Terminology Criteria for Adverse Events. NYHA = New York Heart Association. P + H IV = intravenous pertuzumab and trastuzumab. PH FDC SC = subcutaneous pertuzumab and trastuzumab fixed-dose combination.

TABLE 3

Pharmacokinetic sampling during the neoadjuvant period

| Period/study arm | | | 2- or 3-week cycles | | | | 3-week cycles | | | | | | | | |
|---|---|---|---|---|---|---|---|---|---|---|---|---|---|---|---|
| Cycle | Screening | Baseline | 1 | 2 | 3 | 4 | 5 | | 6 | 7 | | | | 8 | Surgery |
| Day | −28 to −1 | −7 to −1 | 1 | 1 | 1 | 1 | 1 | 2 | 15 | 1 | 1 | 2 | 4 | 8 | 15 | 1 | 1 |
| P + H IV | | | | | | | x | x | x | x | x | x | x | x | x | x |
| PH FDC SC | | | | | | | x | x | x | x | x | x | x | x | x | x |

P + H IV = intravenous pertuzumab and trastuzumab. PH FDC SC = subcutaneous pertuzumab and trastuzumab fixed-dose combination.

TABLE 4

Total pathological complete response (pCR) in patient subgroups in the intention-to-treat population

| | Arm A: intravenous pertuzumab plus trastuzumab (n = 252) n/N (%; 95% CI) | Arm B: fixed-dose combination of pertuzumab and trastuzumab for subcutaneous injection (n = 248) n/N (%, 95% CI) |
|---|---|---|
| Clinical stage at presentation | | |
| II-IIIA | 124/201 (61.7%; 54.59-68.44) | 121/198 (61.1%; 53.94-67.94) |
| IIIB-IIIC | 26/51 (51.0%; 36.60-65.25) | 27/50 (54.0%; 39.32-68.19) |
| Chemotherapy regimen | | |
| ddAC followed by paclitaxel | 76/120 (63.3%; 54.05-71.94) | 80/120 (66.7%; 57.48-75.01) |
| AC followed by docetaxel | 74/132 (56.1%; 47.16-64.68) | 68/128 (53.1%; 44.11-62.00) |
| Hormone receptor status | | |
| Estrogen and/or progesterone receptor-positive | 86/155 (55.5%; 47.30-63.46) | 79/151 (52.3%; 44.04-60.50) |
| Estrogen and progesterone receptor-negative | 64/97 (66.0%; 55.66-75.30) | 68/96 (70.8%; 60.67-79.67) |
| Estrogen or progesterone receptor status unknown | 0/0 | 1/1 (100%; 2.50-100.00) |
| Age (years) | | |
| <65 | 131/219 (59.8%; 53.00-66.37) | 134/222 (60.4%; 53.60-66.84) |
| ≥65 | 19/33 (57.6%; 39.22-74.52) | 14/26 (53.8%; 33.37-73.41) |
| Body mass index (WHO classification) | | |
| Underweight (<18.5 kg/m$^2$) | 3/3 (100%; 29.24-100) | 3/7 (42.9%; 9.90-81.59) |
| Normal (18.5-<25.0 kg/m$^2$) | 71/120 (59.2%; 49.82-68.05) | 70/112 (62.5%; 52.85-71.47) |
| Overweight (25.0-<30.0 kg/m$^2$) | 45/80 (56.3%; 44.70-67.32) | 49/75 (65.3%; 53.46-75.96) |
| Obese (≥30.0 kg/m$^2$) | 31/49 (63.3%; 48.29-76.58) | 26/54 (48.1%; 34.34-62.16) |
| Histological subtype | | |
| Invasive carcinoma NST | 114/194 (58.8%; 51.49-65.77) | 117/197 (59.4%; 52.18-66.31) |
| Invasive lobular carcinoma | 10/16 (62.5%; 35.43-84.80) | 9/13 (69.2%; 38.57-90.91) |
| Invasive micropapillary carcinoma | 1/2 (50.0%; 1.26-98.74) | 0/1 (0-97.50) |
| Mucinous carcinoma | 1/3 (33.3%; 0.84-90.57) | 1/2 (50.0%; 1.26-98.74) |
| Apocrine carcinoma | 3/3 (100%; 29.24-100) | 1/2 (50.0%; 1.26-98.74) |
| Other | 21/34 (61.8%; 43.56-77.83) | 20/33 (60.6%; 42.14-77.09) |
| Histological grade | | |
| GX | 2/2 (100%; 15.81-100) | 2/4 (50.0%; 6.76-93.24) |
| G1 | 4/9 (44.4%; 13.70-78.80) | 2/3 (66.7%; 9.43-99.16) |

TABLE 4-continued

Total pathological complete response (pCR) in patient subgroups in the intention-to-treat population

| | Arm A:<br>intravenous pertuzumab<br>plus trastuzumab<br>(n = 252)<br>n/N (%; 95% CI) | Arm B:<br>fixed-dose combination of<br>pertuzumab and trastuzumab<br>for subcutaneous injection<br>(n = 248)<br>n/N (%, 95% CI) |
|---|---|---|
| G2 | 73/119 (61.3%; 51.98-70.13) | 66/116 (56.9%; 47.38-66.06) |
| G3 | 49/80 (61.3%; 49.70-71.94) | 59/90 (65.6%; 54.80-75.26) |
| Unknown | 22/42 (52.40%; 36.42-68.00) | 19/35 (54.3%; 36.65-71.17) |
| Menopausal status | | |
| Premenopausal | 88/144 (61.1%; 52.64-69.12) | 69/118 (58.5%; 49.04-67.47) |
| Postmenopausal | 61/106 (57.5%; 47.57-67.09) | 79/130 (60.8%; 51.82-69.21) |
| Unknown | 1/2 (50.0%; 1.26-98.74) | 0 |
| Ethnic origin | | |
| White | 99/164 (60.4%; 52.44-67.91) | 99/165 (60.0%; 52.10-67.54) |
| Asian | 26/54 (48.1%; 34.34-62.16) | 31/51 (60.8%; 46.11-74.16) |
| Black or African American | 2/3 (66.7%; 9.43-99.16) | 3/3 (100%; 29.24-100) |
| American Indian or Alaskan Native | 8/10 (80.0%; 44.39-97.48) | 6/10 (60.0%; 26.24-87.84) |
| Multiple | 1/2 (50.0%; 1.26-98.74) | 2/3 (66.7%; 9.43-99.16) |
| Unknown | 14/19 (73.7%; 48.80-90.85) | 7/16 (43.8%; 19.75-70.12) |

Values are number of responders/total number of patients in the subgroup (n/N) tpCR rate (%, 95% confidence interval).
AC = doxorubicin plus cyclophosphamide. CI = confidence interval (calculated by the Pearson-Clopper method). ddAC = dose-dense doxorubicin plus cyclophosphamide. NST = no special type. WHO = World Health Organization.

TABLE 5

Multiple logistic regression analysis of total pCR (exploratory endpoint) in the intention-to-treat population

| | Estimate | Standard error | Wald Chi-square p |
|---|---|---|---|
| Intercept | 0.8232 | 0.4883 | 0.0918 |
| Age <65 years | 0.0799 | 0.1576 | 0.6123 |
| Post-menopausal | 0.0089 | 0.1044 | 0.9319 |
| Race | | | |
| Asian | −0.1668 | 0.1906 | 0.3813 |
| Other | 0.1944 | 0.1993 | 0.3293 |
| Estrogen and progesterone receptor-negative | 0.3625 | 0.1014 | 0.0003 |
| Clinical stage II-IIIA at presentation | 0.2437 | 0.1187 | 0.0401 |
| AC followed by docetaxel | −0.2077 | 0.1080 | 0.0545 |
| PH FDC SC | −0.0010 | 0.0945 | 0.9917 |
| Body weight | −0.0074 | 0.0067 | 0.2672 |

Degrees of freedom = 1. Estimate = coefficient of logistic regression such that odds ratio = exponential of the estimate. PH FDC SC = subcutaneous pertuzumab and trastuzumab fixed-dose combination.

TABLE 6

Incidence of treatment-emergent anti-drug and anti-recombinant human hyaluronidase antibodies and their relationship to cycle 7 (i.e., pre-dose cycle 8) serum trough concentration, total pCR, and injection-/infusion-related or administration-related reactions (post-baseline-evaluable patients in the per-protocol pharmacokinetic, intention-to-treat, and safety populations, respectively)

| | Arm A:<br>P + H IV | Arm B:<br>PH FDC SC |
|---|---|---|
| Anti-P | | |
| Negative | 230/237 (97.0%) | 220/231 (95.2%) |
| Cycle 7 $C_{trough}$ | 80.0 (28.1)* | 93.6 (30.8)* |
| tpCR | 143/230 (62.2%) | 132/220 (60.0%) |
| Injection-/infusion-related reactions (relevant to P + H IV) or administration-associated reactions (relevant to PH FDC SC SC) | 31/230 (13.5%) | 42/220 (19.1%) |
| Positive | 7/237 (3.0%) | 11/231 (4.8%) |
| Cycle 7 $C_{trough}$ | 56.0 (27.0)† | 90.6 (34.0)† |
| tpCR | 5/7 (71.4%) | 7/11 (63.6%) |
| Injection-/infusion-related reactions (relevant to P + H IV) or administration-associated reactions (relevant to PH FDC SC SC) | 1/7 (14.3%) | 0/11 |

TABLE 6-continued

Incidence of treatment-emergent anti-drug and anti-recombinant human hyaluronidase antibodies and their relationship to cycle 7 (i.e., pre-dose cycle 8) serum trough concentration, total pCR, and injection-/infusion-related or administration-related reactions (post-baseline-evaluable patients in the per-protocol pharmacokinetic, intention-to-treat, and safety populations, respectively)

|  | Arm A: P + H IV | Arm B: PH FDC SC |
|---|---|---|
| Anti-H | | |
| Negative | 236/237 (99.6%) | 230/232 (99.1%) |
| Cycle 7 $C_{trough}$ | 48.8 (21.3)‡ | 63.0 (23.2)‡ |
| tpCR | 147/236 (62.3%) | 138/230 (60.0%) |
| Injection-/infusion-related reactions (relevant to P + H IV) or administration-associated reactions (relevant to PH FDC SC SC) | 32/236 (13.6%) | 43/230 (18.7%) |
| Positive | 1/237 (0.4%) | 2/232 (0.9%) |
| Cycle 7 $C_{trough}$ | 57.0 (not evaluable)§ | 41.3 (not evaluable)§ |
| tpCR | 0/1 | 2/2 (100%) |
| Injection-/infusion-related reactions (relevant to P + H IV) or administration-associated reactions (relevant to PH FDC SC SC) | 0/1 | 0/2 |
| Anti-rHuPH20 | | |
| Negative | — | 223/225 (99.1%) |
| tpCR | — | 136/223 (61.0%) |
| Injection-/infusion-related reactions (relevant to P + H IV) or administration-associated reactions (relevant to PH FDC SC SC) | — | 41/223 (18.4%) |
| Positive | — | 2/225 (0.9%) |
| tpCR | — | 0/2 |
| Injection-/infusion-related reactions (relevant to P + H IV) or administration-associated reactions (relevant to PH FDC SC SC) | — | 0/2 |

Data are number of patients (%) or mean (SD).
*n = 193 and 192, respectively.
†n = 5 and 8, respectively.
‡n = 197 and 200, respectively.
§n = 1 per arm.
$C_{trough}$ = serum trough concentration P + H IV = intravenous pertuzumab and trastuzumab. PH FDC SC = subcutaneous pertuzumab and trastuzumab fixed-dose combination. rHuPH20 = recombinant human hyaluronidase. SD = standard deviation. tpCR = total pathological complete response (ypT0/is, ypN0).

Publications Cited in Example 1

1. Wolff et al. Human epidermal growth factor receptor 2 testing in breast cancer: American Society of Clinical Oncology/College of American Pathologists clinical practice guideline focused update. Arch Pathol Lab Med 2018; 142(11): 1364-82.
2. Slamon et al. Human breast cancer: Correlation of relapse and survival with amplification of the HER-2/neu oncogene. Science 1987; 235(4785): 177-82.
3. Swain et al. Pertuzumab, trastuzumab, and docetaxel in HER2-positive metastatic breast cancer. N Engl J Med 2015; 372(8): 724-34.
4. Gianni et al. Efficacy and safety of neoadjuvant pertuzumab and trastuzumab in women with locally advanced, inflammatory, or early HER2-positive breast cancer (NeoSphere): a randomised multicentre, open-label, phase 2 trial. Lancet Oncol 2012; 13(1): 25-32.
5. von Minckwitz et al. Adjuvant pertuzumab and trastuzumab in early HER2-positive breast cancer. N Engl J Med 2017; 377(2): 122-31.
6. Poorter et al. Complications of an implantable venous access device (Port-a-Cath) during intermittent continuous infusion of chemotherapy. Eur J Cancer 1996; 32A (13): 2262-6.
7. Shivakumar et al. Catheter-associated thrombosis in patients with malignancy. J Clin Oncol 2009; 27(29): 4858-64.
8. De Cock et al. A time and motion study of subcutaneous versus intravenous trastuzumab in patients with HER2-positive early breast cancer. Cancer Med 2016; 5(3): 389-97.
9. Ismael et al. Subcutaneous versus intravenous administration of (neo)adjuvant trastuzumab in patients with HER2-positive, clinical stage I-III breast cancer (HannaH study): a phase 3, open-label, multicentre randomised trial. Lancet Oncol 2012; 13(9): 869-78.
10. Jackisch et al. HannaH phase III randomised study: Association of total pathological complete response with event-free survival in HER2-positive early breast cancer treated with neoadjuvant-adjuvant trastuzumab after 2 years of treatment-free follow-up. Eur J Cancer 2016; 62: 62-75.
11. Jackisch et al. Subcutaneous vs intravenous trastuzumab for patients with ERBB2-positive early breast cancer: Final analysis of the HannaH phase 3 randomized clinical trial. JAMA Oncol 2019; 5(5): e190339.
12. Pivot et al. Preference for subcutaneous or intravenous administration of trastuzumab in patients with HER2-positive early breast cancer (PrefHer): An open-label randomised study. Lancet Oncol 2013; 14(10): 962-70.

13. Pivot et al. Patients' preferences for subcutaneous trastuzumab versus conventional intravenous infusion for the adjuvant treatment of HER2-positive early breast cancer: Final analysis of 488 patients in the international, randomized, two-cohort PrefHer study. Ann Oncol 2014; 25(10): 1979-87.
14. Pivot et al. Efficacy and safety of subcutaneous trastuzumab and intravenous trastuzumab as part of adjuvant therapy for HER2-positive early breast cancer: Final analysis of the randomised, two-cohort PrefHer study. Eur J Cancer 2017; 86: 82-90.
15. Davies et al. Pharmacokinetics and safety of subcutaneous rituximab in follicular lymphoma (SABRINA): Stage 1 analysis of a randomised phase 3 study. Lancet Oncol 2014; 15(3): 343-52.
16. Assouline et al. Pharmacokinetics and safety of subcutaneous rituximab plus fludarabine and cyclophosphamide for patients with chronic lymphocytic leukaemia. Br J Clin Pharmacol 2015; 80(5): 1001-9.
17. Rummel et al. Preference for subcutaneous or intravenous administration of rituximab among patients with untreated CD20+ diffuse large B-cell lymphoma or follicular lymphoma: Results from a prospective, randomized, open-label, crossover study (PrefMab). Ann Oncol 2017; 28(4): 836-42.
18. Gligorov et al. Safety and tolerability of subcutaneous trastuzumab for the adjuvant treatment of human epidermal growth factor receptor 2-positive early breast cancer: SafeHer phase III study's primary analysis of 2573 patients. Eur J Cancer 2017; 82: 237-46.
19. Kümmel et al. Subcutaneous trastuzumab and hyaluronidase-oysk with intravenous pertuzumab and docetaxel in HER2-positive advanced breast cancer: Final analysis of the phase IIIb, multicenter, open-label, single-arm MetaPHER study. Cancer Res 2019; 20(4 Suppl): Abstract P1-18-05.
20. Haller M F. Converting intravenous dosing to subcutaneous dosing with recombinant human hyaluronidase. Pharm Technol 2007; 31(10): 118-32.
21. Pivot et al. Patients' preference of trastuzumab administration (subcutaneous versus intravenous) in HER2-positive metastatic breast cancer: Results of the randomised MetaspHer study. Eur J Cancer 2017; 82: 230-6.
22. Beaute et al. Economic evaluation of immunoglobulin replacement in patients with primary antibody deficiencies. Clin Exp Immunol 2010; 160(2): 240-5.
23. Gardulf A. Immunoglobulin treatment for primary antibody deficiencies: Advantages of the subcutaneous route. BioDrugs 2007; 21(2): 105-16.
24. Kirschbrown et al. Development of a subcutaneous fixed-dose combination of pertuzumab and trastuzumab: Results from the phase Ib dose-finding study. J Clin Pharmacol 2019; 59(5): 702-16.
25. Pegram et al. Inhibitory effects of combinations of HER-2/neu antibody and chemotherapeutic agents used for treatment of human breast cancers. Oncogene 1999; 18(13): 2241-51.
26. Swain et al. Pertuzumab, trastuzumab, and standard anthracycline- and taxane-based chemotherapy for the neoadjuvant treatment of patients with HER2-positive localized breast cancer (BERENICE): A phase II, open-label, multicenter, multinational cardiac safety study. Ann Oncol 2018; 29(3): 646-53.
27. Schneeweiss et al. Pertuzumab plus trastuzumab in combination with standard neoadjuvant anthracycline-containing and anthracycline-free chemotherapy regimens in patients with HER2-positive early breast cancer: A randomized phase II cardiac safety study (TRYPHAENA). Ann Oncol 2013; 24(9): 2278-84.
28. Loibl et al. Dual HER2-blockade with pertuzumab and trastuzumab in HER2-positive early breast cancer: A subanalysis of data from the randomized phase III GeparSepto trial. Ann Oncol 2017; 28(3): 497-504.
29. Hurvitz et al. Neoadjuvant trastuzumab, pertuzumab, and chemotherapy versus trastuzumab emtansine plus pertuzumab in patients with HER2-positive breast cancer (KRISTINE): A randomised, open-label, multicentre, phase 3 trial. Lancet Oncol 2018; 19(1): 115-26.
30. Denys et al. Safety and tolerability of subcutaneous trastuzumab at home administration, results of the phase IIIb open-label BELIS study in HER2-positive early breast cancer. Breast Cancer Res Treat 2020 (epub ahead of print).
31. Papakonstantinou et al. Efficacy and Safety of Tailored and Dose-Dense Adjuvant Chemotherapy and Trastuzumab for Resected HER2-positive Breast Cancer: Results From the Phase 3 PANTHER Trial. Cancer 2020; 126(6): 1175-82.
32. Lambertini et al. Dose-dense Adjuvant Chemotherapy in HER2-positive Early Breast Cancer Patients Before and After the Introduction of Trastuzumab: Exploratory Analysis of the GIM2 Trial. Int J Cancer 2020; 147(1): 160-9.

Example 2: Pertuzumab-Trastuzumab Fixed Dose Combination (PH FDC) Full Prescribing Information Warning: Cardiomyopathy, Embryo-Fetal Toxicity, and Pulmonary Toxicity
Cardiomyopathy
PH FDC administration can result in subclinical and clinical cardiac failure. The incidence and severity was highest in patients receiving PH FDC with anthracycline-containing chemotherapy regimens.
  1. Evaluate cardiac function prior to and during treatment with PH FDC. Discontinue PH FDC treatment in patients receiving adjuvant therapy and withhold PH FDC in patients with metastatic disease for clinically significant decrease in left ventricular function [see Dosage and Administration (2.3) and Warnings and Precautions (5.1)].
Embryo-Fetal Toxicity
Exposure to PH FDC can result in embryo-fetal death and birth defects, including oligohydramnios and oligohydramnios sequence manifesting as pulmonary hypoplasia, skeletal abnormalities, and neonatal death. Advise patients of these risks and the need for effective contraception [see Warnings and Precautions (5.2) and Use in Specific Populations (8.1), (8.3)].
Pulmonary Toxicity
PH FDC administration can result in serious and fatal pulmonary toxicity. Discontinue PH FDC for anaphylaxis, angioedema, interstitial pneumonitis, or acute respiratory distress syndrome. Monitor patients until symptoms completely resolve [see Warnings and Precautions (5.3)].
1 Indications and Usage
1.1 Early Breast Cancer (EBC)
PH FDC is indicated for use in combination with chemotherapy for
  the neoadjuvant treatment of adult patients with HER2-positive, locally advanced, inflammatory, or early stage breast cancer (either greater than 2 cm in diameter or node positive) as part of a complete treatment regimen for early breast cancer [see Dosage and Administration (2.2) and Clinical Studies (14.2)].

the adjuvant treatment of adult patients with HER2-positive early breast cancer at high risk of recurrence [see Dosage and Administration (2.2) and Clinical Studies (14.2)].

Select patients for therapy based on an FDA-approved companion diagnostic test [see Dosage and Administration (2.1)].

1.2 Metastatic Breast Cancer (MBC)

PH FDC is indicated for use in combination with docetaxel for the treatment of adult patients with HER2-positive metastatic breast cancer who have not received prior anti-HER2 therapy or chemotherapy for metastatic disease [see Dosage and Administration (2.2) and Clinical Studies (14.1)].

Select patients for therapy based on an FDA-approved companion diagnostic test [see Dosage and Administration (2.1)].

2 Dosage and Administration 2.1 Patient Selection

Select patients based on HER2 protein overexpression or HER2 gene amplification in tumor specimens [see Indications and Usage (1) and Clinical Studies (14)]. Assessment of HER2 protein overexpression and HER2 gene amplification should be performed using FDA-approved tests specific for breast cancer by laboratories with demonstrated proficiency. Information on the FDA-approved tests for the detection of HER2 protein overexpression and HER2 gene amplification is available from the FDA.

Improper assay performance, including use of suboptimally fixed tissue, failure to utilize specified reagents, deviation from specific assay instructions, and failure to include appropriate controls for assay validation, can lead to unreliable results.

2.2 Important Dosage and Administration Information

PH FDC is for subcutaneous use only in the thigh. Do not administer intravenously.

PH FDC has different dosage and administration instructions than intravenous pertuzumab, intravenous trastuzumab, and subcutaneous trastuzumab when administered alone.

Do not substitute PH FDC for or with pertuzumab, trastuzumab, ado-trastuzumab emtansine, or fam-trastuzumab deruxtecan.

PH FDC must always be administered by a healthcare professional.

In patients receiving an anthracycline-based regimen for early breast cancer, administer PH FDC following completion of the anthracycline.

In patients receiving PH FDC for early breast cancer with docetaxel or paclitaxel, administer docetaxel or paclitaxel after PH FDC.

In patients receiving PH FDC for metastatic breast cancer with docetaxel, administer docetaxel after PH FDC.

Observe patients for a minimum of 30 minutes after loading dose of PH FDC and 15 minutes after each maintenance dose of PH FDC for signs or hypersensitivity symptoms or administration-related reactions. Medications to treat such reactions, as well as emergency equipment, should be available for immediate use [see Warnings and Precautions (5.5)].

2.3 Recommended Doses and Schedules

The recommended dosage and administration schedule for PH FDC are shown in Table 7.

TABLE 7

Recommended Dosage and Administration Schedule

| Dose | Strength | Administration Instructions |
|---|---|---|
| Initial dose | 1200 mg pertuzumab, 600 mg trastuzumab, and 30,000 units hyaluronidase in 15 mL (1200 mg, 600 mg, and 30,000 units/15 mL) | Administer subcutaneously over approximately 8 minutes |
| Maintenance dose (administer every 3 weeks) | 600 mg pertuzumab, 600 mg trastuzumab, and 20,000 units hyaluronidase in 10 mL (600 mg, 600 mg, and 20,000 units/10 mL) | Administer subcutaneously over approximately 5 minutes every 3 weeks |

No dose adjustments for PH FDC are required for patient body weight or for concomitant chemotherapy regimen.

Patients currently receiving intravenous pertuzumab and trastuzumab can transition to PH FDC. In patients receiving intravenous pertuzumab and trastuzumab with <6 weeks since their last dose, administer PH FDC as a maintenance dose of 600 mg pertuzumab/600 mg trastuzumab and every 3 weeks for subsequent administrations. In patients receiving intravenous pertuzumab and trastuzumab with ≥6 weeks since their last dose, administer PH FDC as an initial dose of 1200 mg pertuzumab/600 mg trastuzumab, followed by a maintenance dose of 600 mg pertuzumab/600 mg trastuzumab every 3 weeks for subsequent administrations.

Neoadjuvant Treatment of Breast Cancer

Administer PH FDC every 3 weeks for 3 to 6 cycles as part of a treatment regimen for early breast cancer [see Clinical Studies (14.2)].

Refer to the prescribing information for pertuzumab, administered in combination with trastuzumab and chemotherapy, for recommended dose and dosage modifications.

Following surgery, patients should continue to receive PH FDC to complete 1 year of treatment (up to 18 cycles) or until disease recurrence or unmanageable toxicity, whichever occurs first, as a part of a complete regimen for early breast cancer.

Adjuvant Treatment of Breast Cancer

Administer PH FDC every 3 weeks for a total of 1 year (up to 18 cycles) or until disease recurrence or unmanageable toxicity, whichever occurs first, as part of a complete regimen for early breast cancer, including standard anthracycline- and/or taxane-based chemotherapy. Start PH FDC on Day 1 of the first taxane-containing cycle [see Clinical Studies (14.2)].

Metastatic Breast Cancer (MBC)

When administered with PH FDC, the recommended initial dose of docetaxel is 75 mg/m$^2$ administered as an intravenous infusion. The dose may be escalated to 100 mg/m$^2$ administered every 3 weeks if the initial dose is well tolerated. Administer PH FDC until disease progression or unmanageable toxicity, whichever occurs first.

2.4 Dose Modification

Dose Modification for Delayed or Missed Doses

For delayed or missed doses of PH FDC, if the time between two sequential injections is less than 6 weeks, administer the maintenance dose of 600 mg, 600 mg, and 20,000 units/10 mL. Do not wait until the next planned dose.

If the time between two sequential injections is 6 weeks or more, re-administer the loading dose of 1200 mg, 600 mg, and 30,000 units/15 mL, followed every 3 weeks thereafter by a maintenance dose of 600 mg, 600 mg, and 20,000 units/10 mL.

For chemotherapy dose modifications, see relevant prescribing information.

Cardiomyopathy [See Boxed Warning, Warnings and Precautions (5.1)]

Assess left ventricular ejection fraction (LVEF) prior to initiation of PH FDC and at regular intervals during treatment as indicated in Table 8.

The recommendations on dose modifications in the event of LVEF dysfunction are indicated in Table 8 [see Warnings and Precautions (5.1)].

administered is PH FDC and not intravenous pertuzumab, or intravenous trastuzumab, or subcutaneous trastuzumab.

Parenteral drug products should be inspected visually for particulate matter and discoloration prior to administration, whenever solution and container permit. Do not use vial if particulates or discoloration is present. Do not shake. Discard any unused portion remaining in the vial.

For both the initial and maintenance dose, each corresponding PH FDC vial is ready-to-use for one subcutaneous injection and should not be diluted.

A syringe, a transfer needle, and an injection needle are needed to withdraw PH FDC solution from the vial and inject it subcutaneously. PH FDC may be injected using 25G-27G (⅜"-⅝") hypodermic injection needles.

To avoid needle clogging, attach the hypodermic injection needle to the syringe immediately prior to administration followed by volume adjustment to 15 mL (loading dose) and 10 mL (maintenance dose). If the dose is not to be administered immediately, and the solution of PH FDC has been withdrawn from the vial into the syringe, replace the transfer needle with a syringe closing cap. Label the syringe with the peel-off sticker and store the syringe in the refrigerator [2° C. to 8° C. (36° F. to 46° F.)] for up to 24 hours and at room temperature [20° C. to 25° C. (68° F. to 77° F.)] for up to 4 hours and avoid unnecessary storage.

PH FDC is compatible with stainless steel, polypropylene, polycarbonate, polyethylene, polyurethane, polyvinyl chloride and fluorinated ethylene polypropylene.

TABLE 8

Dose Modifications for Left Ventricular Dysfunction

| | Pre-treatment LVEF: | Monitor LVEF every: | Withhold PH FDC for at least 3 weeks for an LVEF decrease to: | | Resume PH FDC after 3 weeks if LVEF has recovered to: | |
|---|---|---|---|---|---|---|
| Early Breast Cancer | ≥55%* | ~12 weeks (once during neoadjuvant therapy) | <50% with a fall of ≥10%-points below pre-treatment value | | Either | |
| | | | | | ≥50% | <10% points below pre-treatment value |
| Metastatic Breast Cancer | ≥50% | ~12 weeks | Either | | Either | |
| | | | <40% | 40%-45% with a fall of ≥10%-points below pre-treatment value | >45% | 40%-45% with a fall of <10%-points below pre-treatment value |

*For patients receiving anthracycline-based chemotherapy, a LVEF of ≥50% is required after completion of anthracyclines, before starting PH FDC If after a repeat assessment within approximately 3 weeks, the LVEF has not improved, has declined further, and/or the patient is symptomatic, permanently discontinue PH FDC [see Warnings and Precautions (5.1)].

Hypersensitivity and Administration-Related Reactions

Discontinue the injection immediately if the patient experiences a serious hypersensitivity reaction (e.g. anaphylaxis) [see Warnings and Precautions (5.5)].

2.5 Preparation for Administration

To prevent medication errors, it is important to check the vial labels to ensure that the drug being prepared and Administration
  Administer PH FDC 1200 mg, 600 mg, 30,000 units/15 mL subcutaneously over approximately 8 minutes
  Administer PH FDC 600 mg, 600 mg, 20,000 units/10 mL subcutaneously over approximately 5 minutes The subcutaneous injection site should be alternated between the left and right thigh only. New injections should be given at least 1 inch (2.5 cm) from the previous site on healthy skin and never into areas where the skin is red, bruised, tender, or hard. Do not split the dose between two syringes or between two sites of administration. During the treatment course with PH FDC, other medications for subcutaneous administration should preferably be injected at different sites.

3 Dosage Forms and Strengths

Injection: PH FDC is a clear to opalescent, and colorless to slightly brownish solution provided as:
- 1200 mg pertuzumab, 600 mg trastuzumab, and 30,000 units hyaluronidase/15 mL (80 mg, 40 mg, and 2,000 units/mL) of solution in a single-dose vial
- 600 mg pertuzumab, 600 mg trastuzumab, and 20,000 units hyaluronidase/10 mL (60 mg, 60 mg, and 2,000 units/mL) of solution in a single-dose vial 4 Contraindications PH FDC is contraindicated in patients with known hypersensitivity to pertuzumab, or trastuzumab, or hyaluronidase, or to any of its excipients 5 Warnings and Precautions 5.1 Cardiomyopathy PH FDC can cause hypertension, arrhythmias, left ventricular cardiac dysfunction, disabling cardiac failure, cardiomyopathy, and cardiac death [see Boxed Warning: Cardiomyopathy]. PH FDC can cause asymptomatic decline in LVEF.

An increased incidence of LVEF decline has been observed in patients treated with intravenous pertuzumab, intravenous trastuzumab, and docetaxel. A 4-6 fold increase in the incidence of symptomatic myocardial dysfunction has been reported among patients receiving trastuzumab, with the highest absolute incidence occurring when trastuzumab was administered with an anthracycline.

Patients who receive anthracycline after stopping PH FDC may also be at increased risk of cardiac dysfunction [see Drug Interactions (7) and Clinical Pharmacology (12.2)].

Cardiac Monitoring

Prior to initiation of PH FDC, conduct a thorough cardiac assessment, including history, physical examination, and determination of LVEF by echocardiogram or MUGA scan.

During treatment with PH FDC, assess LVEF at regular intervals [see Dosage and Administration (2.4)].

If after a repeat assessment within approximately 3 weeks, the LVEF has not improved, has declined further, and/or the patient is symptomatic, permanently discontinue PH FDC.

Following completion of PH FDC, continue to monitor for cardiomyopathy and assess LVEF measurements every 6 months for at least 2 years as a component of adjuvant therapy.

PH FDC

In the FeDeriCa study, the percentage of patients with at least one cardiac disorder was 22% in the PH FDC arm. The most frequent cardiac adverse reaction in the PH FDC arm was ejection fraction decreased.

The incidence of cardiac failure (NYHA Class III/IV) with a LVEF decline ≥10% and a drop to less than 50% was 0.8% in the PH FDC arm. Confirmed asymptomatic or mildly symptomatic (NYHA Class II) declines in LVEF≥10% and a drop to less than 50% was 1.2% in the PH FDC arm [see Adverse Reactions (6.1)].

PH FDC and/or intravenous pertuzumab and trastuzumab have not been studied in patients with a pretreatment LVEF value of <55% (EBC) or <50% (MBC); a prior history of CHF, conditions that could impair left ventricular function such as uncontrolled hypertension, recent myocardial infarction, serious cardiac arrhythmia requiring treatment or a cumulative prior anthracycline exposure to >360 mg/m$^2$ of doxorubicin or its equivalent.

5.2 Embryo-Fetal Toxicity

PH FDC can cause fetal harm when administered to a pregnant woman. In post-marketing reports, use of intravenous trastuzumab during pregnancy resulted in cases of oligohydramnios and oligohydramnios sequence manifesting as pulmonary hypoplasia, skeletal abnormalities, and neonatal death. In an animal reproduction study, administration of intravenous pertuzumab to pregnant cynomolgus monkeys during the period of organogenesis resulted in oligohydramnios, delayed fetal kidney development, and embryo-fetal death at exposures 2.5 to 20 times the exposure in humans at the recommended dose, based on $C_{max}$.

Verify the pregnancy status of females of reproductive potential prior to the initiation of PH FDC. Advise pregnant women and females of reproductive potential that exposure to PH FDC during pregnancy or within 7 months prior to conception can result in fetal harm. Advise females of reproductive potential to use effective contraception during treatment and for 7 months following the last dose of PH FDC [see Use in Specific Populations (8.1, 8.3) and Clinical Pharmacology (12.3)].

5.3 Pulmonary Toxicity

PH FDC can cause serious and fatal pulmonary toxicity. These adverse reactions have been reported with intravenous trastuzumab. Pulmonary toxicity includes dyspnea, interstitial pneumonitis, pulmonary infiltrates, pleural effusions, non-cardiogenic pulmonary edema, pulmonary insufficiency and hypoxia, acute respiratory distress syndrome, and pulmonary fibrosis. Patients with symptomatic intrinsic lung disease or with extensive tumor involvement of the lungs, resulting in dyspnea at rest, appear to have more severe toxicity.

5.4 Exacerbation of Chemotherapy-Induced Neutropenia

PH FDC may exacerbate chemotherapy-induced neutropenia. In randomized controlled clinical trials with intravenous trastuzumab, Grade 3-4 neutropenia and febrile neutropenia were higher in patients receiving trastuzumab in combination with myelosuppressive chemotherapy as compared to those who received chemotherapy alone. The incidence of septic death was similar among patients who received trastuzumab and those who did not.

5.5 Hypersensitivity and Administration-Related Reactions

Severe administration-related reactions (ARRs), including hypersensitivity, anaphylaxis, and events with fatal outcomes, have been associated with intravenous pertuzumab and trastuzumab. Patients experiencing dyspnea at rest due to complications of advanced malignancy and comorbidities may be at increased risk of a severe or of a fatal ARR.

In the FeDeriCa study, the incidence of hypersensitivity was 1.2% in the PH FDC arm. Administration-related reactions occurred in 21% of patients who received PH FDC. In the PH FDC arm, the most common administration-related reactions were injection site reaction (15%) and injection site pain (2%).

Closely monitor patients during and for 30 minutes after the injection of initial dose and during and for 15 minutes following subsequent injections of maintenance dose of PH FDC. If a significant injection-related reaction occurs, slow down or pause the injection and administer appropriate medical therapies. Evaluate and carefully monitor patients until complete resolution of signs and symptoms.

Permanently discontinue with PH FDC in patients who experience anaphylaxis or severe injection-related reactions. Medications to treat such reactions, as well as emergency equipment, should be available for immediate use. For patients experiencing reversible Grade 1 or 2 hypersensitivity reactions, consider pre-medication with an analgesic, antipyretic, or an antihistamine prior to readministration of PH FDC [see Adverse Reactions (6.1)].

PH FDC is contraindicated in patients with known hypersensitivity to pertuzumab, trastuzumab, hyaluronidase or to any of its excipients [see Contraindications (4)].

6 Adverse Reactions

The following adverse reactions are discussed in greater detail in other sections of the label:
 Cardiomyopathy [see Warnings and Precautions (5.1)]
 Embryo-Fetal Toxicity [see Warnings and Precautions (5.2)]
 Pulmonary Toxicity [see Warnings and Precautions (5.3)]
 Exacerbation of Chemotherapy-Induced Neutropenia [see Warnings and Precautions (5.4)]
 Hypersensitivity and Administration-Related Reactions [see Warnings and Precautions (5.5)]

6.1 Clinical Trials Experience

Because clinical trials are conducted under widely varying conditions, adverse reaction rates observed in the clinical trials of a drug cannot be directly compared to rates in the clinical trials of another drug and may not reflect the rates observed in practice.

Neoadjuvant and Adjuvant Treatment of Breast Cancer

The safety of PH FDC was evaluated in an open-label, multicenter, randomized study (FeDeriCa) conducted in 500 patients with HER2 overexpressing early breast cancer [see Clinical Studies (14.2)].

Patients were randomized to receive either PH FDC (1200 mg pertuzumab, 600 mg trastuzumab, and 30,000 units hyaluronidase/15 mL) followed every 3 weeks by a maintenance dose of 600 mg pertuzumab, 600 mg trastuzumab, and 20,000 units hyaluronidase/10 mL or the recommended dosages for intravenous pertuzumab and intravenous trastuzumab. Patients were randomized to receive 8 cycles of neoadjuvant chemotherapy with concurrent administration of 4 cycles of either PH FDC or intravenous pertuzumab and trastuzumab during cycles 5-8, followed by surgery. Following surgery, patients continued therapy with PH FDC or intravenous pertuzumab and trastuzumab (intravenous or subcutaneously administered) as treated prior to surgery, for an additional 14 cycles, to complete 18 cycles. The median duration of treatment for PH FDC was 24 weeks (range: 0-42 weeks).

Serious adverse reactions occurred in 16% of patients who received PH FDC. Serious adverse reactions in >1% of patients included febrile neutropenia (4%), neutropenic sepsis (1%), and neutrophil count decreased (1%). One fatal adverse reaction occurred in 1/248 (0.4%) of patients, which was due to acute myocardial infarction, and occurred prior to the start of HER2 targeted treatment with PH FDC.

Adverse reactions resulting in permanent discontinuation of any study drug occurred in 8% of patients on the PH FDC arm. Adverse reactions which resulted in permanent discontinuation of PH FDC were ejection fraction decreased (1.2%), cardiac failure (0.8%), and pneumonitis/pulmonary fibrosis (0.8%).

Dosage interruptions due to an adverse reaction occurred in 40% of patients who received PH FDC. Adverse reactions which required dosage interruption in >1% of patients who received PH FDC included neutropenia (8%), neutrophil count decreased (4%), and diarrhea (7%).

Table 9 summarizes the adverse reactions in FeDeriCa.

TABLE 9

Adverse Reactions (≥5%) in Patients Who Received PH FDC in FeDeriCa

| Body System/Adverse Reactions | PH FDC (n = 248) | | Intravenous pertuzumab plus intravenous or subcutaneous trastuzumab (n = 252) | |
|---|---|---|---|---|
| | All Grades % | Grades 3-4 % | All Grades % | Grades 3-4 % |
| Skin and subcutaneous tissue disorders | | | | |
| Alopecia | 77 | 0 | 71 | 0.4 |
| Dry skin | 15 | 0.4 | 13 | 0 |
| Rash | 16 | 0.4 | 21 | 0 |
| Nail discoloration | 9 | 0 | 6 | 0 |
| Erythema | 9 | 0 | 5 | 0 |
| Dermatitis | 7 | 0 | 6 | 0 |
| Nail disorder | 7 | 0 | 7 | 0.4 |
| Palmar-plantar erythrodysesthesia syndrome | 6 | 0.8 | 5 | 0.4 |
| Gastrointestinal disorders | | | | |
| Nausea | 60 | 2 | 61 | 1.6 |
| Diarrhea | 60 | 7 | 57 | 4.8 |
| Stomatitis | 25 | 0.8 | 24 | 0.8 |
| Constipation | 22 | 0 | 21 | 0 |
| Vomiting | 20 | 0.8 | 19 | 1.2 |
| Dyspepsia | 14 | 0 | 12 | 0 |
| Hemorrhoids | 9 | 0 | 4.0 | 0 |
| Abdominal pain upper | 8 | 0 | 6 | 0 |
| Abdominal pain | 9 | 0.4 | 6 | 0 |
| Blood and lymphatic system disorders | | | | |
| Anemia | 36 | 1.6 | 43 | 4.4 |
| Neutropenia | 22 | 14 | 27 | 14 |
| Leukopenia | 9 | 2.4 | 14 | 2 |
| Febrile neutropenia | 7 | 7 | 6 | 6 |

TABLE 9-continued

Adverse Reactions (≥5%) in Patients Who Received PH FDC in FeDeriCa

| Body System/Adverse Reactions | PH FDC (n = 248) | | Intravenous pertuzumab plus intravenous or subcutaneous trastuzumab (n = 252) | |
|---|---|---|---|---|
| | All Grades % | Grades 3-4 % | All Grades % | Grades 3-4 % |
| *General disorders and administration site conditions* | | | | |
| Asthenia | 31 | 0.4 | 32 | 2.4 |
| Fatigue | 29 | 2 | 24 | 2 |
| Mucosal inflammation | 15 | 0.8 | 20 | 1.2 |
| Injection site reaction | 15 | 0 | 0.8 | 0 |
| Pyrexia | 13 | 0 | 16 | 0.4 |
| Edema peripheral | 8 | 0 | 10 | 0 |
| Malaise | 7 | 0 | 6 | 0.4 |
| Influenza-like illness | 5 | 0 | 3.6 | 0 |
| *Nervous system disorders* | | | | |
| Dysgeusia | 17 | 0 | 14 | 0 |
| Peripheral sensory neuropathy | 16 | 0.8 | 14 | 0.4 |
| Headache | 17 | 0 | 25 | 0.8 |
| Neuropathy peripheral | 12 | 0.4 | 15 | 2 |
| Paresthesia | 10 | 0.8 | 8 | 0 |
| Dizziness | 13 | 0 | 11 | 0 |
| *Investigations* | | | | |
| Weight decreased | 11 | 0.8 | 6 | 0.8 |
| *Musculoskeletal and connective tissue disorders* | | | | |
| Myalgia | 25 | 0.4 | 19 | 0.4 |
| Arthralgia | 24 | 0 | 28 | 0.4 |
| Back pain | 10 | 0 | 4.8 | 0 |
| Bone pain | 7 | 0 | 5 | 0 |
| Pain in extremity | 6 | 0 | 8 | 0 |
| Muscle spasms | 6 | 0 | 7 | 0 |
| Musculoskeletal pain | 6 | 0.4 | 8 | 0 |
| *Respiratory, thoracic and mediastinal disorder* | | | | |
| Cough | 15 | 0.4 | 13 | 0 |
| Epistaxis | 12 | 0 | 14 | 0.4 |
| Dyspnea | 10 | 1.2 | 5 | 0 |
| Rhinorrhea | 7 | 0 | 4.4 | 0 |
| *Infections and infestations* | | | | |
| Upper respiratory tract infection | 11 | 0 | 8 | 0.8 |
| Nasopharyngitis | 9 | 0 | 10 | 0 |
| Paronychia | 7 | 0.4 | 3.6 | 0 |
| Urinary tract infection | 7 | 0.4 | 5 | 0 |
| *Injury, poisoning and procedural complications* | | | | |
| Procedural pain | 13 | 0 | 10 | 0 |
| Radiation skin injury | 19 | 0.4 | 19 | 0.4 |
| Infusion related reaction | 3.6 | 0 | 15 | 0.8 |
| *Metabolism and nutrition disorders* | | | | |
| Decreased appetite | 17 | 0.8 | 19 | 0.4 |
| Hypokalemia | 7 | 1.6 | 8 | 0 |
| *Psychiatric disorders* | | | | |
| Insomnia | 17 | 0 | 13 | 0.4 |
| *Eye disorders* | | | | |
| Lacrimation increased | 5 | 0.4 | 6 | 0 |
| Dry eye | 5 | 0.4 | 3.2 | 0 |
| *Vascular disorders* | | | | |
| Hot flush | 12 | 0 | 13 | 0 |

Clinically relevant adverse reactions in <5% of patients who received PH FDC include ejection fraction decreased (3.6%) and pruritus (3.2%).

Table 10 summarizes the laboratory abnormalities in FeDeriCa.

TABLE 10

Select Laboratory Abnormalities (≥5%) that Worsened
from Baseline in Patients Who Received PH FDC in FeDeriCa [1]

| Laboratory Abnormality | PH FDC (n = 248) | | Intravenous pertuzumab plus intravenous or subcutaneous trastuzumab (n = 252) | |
|---|---|---|---|---|
| | All Grades % | Grades 3-4 % | All Grades % | Grades 3-4 % |
| Hematology | | | | |
| Hemoglobin (low) | 90 | 2.8 | 92 | 4.4 |
| Lymphocytes, Absolute (low) | 89 | 37 | 88 | 36 |
| Total Leukocyte Count (low) | 82 | 25 | 78 | 25 |
| Neutrophils. Total Absolute (low) | 68 | 30 | 67 | 33 |
| Platelet (low) | 27 | 0 | 28 | 0.4 |
| Chemistry | | | | |
| Creatinine (high) | 84 | 0 | 87 | 0.4 |
| Alanine aminotransferase (high) | 58 | 1.6 | 68 | 2.4 |
| Aspartate aminotransferase (high) | 50 | 0.8 | 58 | 0.8 |
| Potassium (low) | 17 | 5.2 | 17 | 2.8 |
| Albumin (low) | 16 | 0 | 20 | 0.4 |
| Potassium (high) | 13 | 1.2 | 9 | 0 |
| Sodium (low) | 13 | 0.4 | 10 | 1.6 |
| Bilirubin (high) | 9 | 0 | 9 | 0.4 |
| Glucose (low) | 9 | 0 | 9 | 0.4 |
| Sodium (high) | 7 | 0.8 | 10 | 0.8 |

[1] The denominator used to calculate the rate varied from 163 to 252 based on the number of patients with a baseline value and at least one post-treatment value.

Other Clinical Trials Experience

The safety of the addition of intravenous pertuzumab to trastuzumab in combination with chemotherapy has been established in studies conducted in patients with HER2 overexpressing early breast cancer. The following adverse reactions have been reported following administration of intravenous pertuzumab and trastuzumab: diarrhea, alopecia, nausea, fatigue, neutropenia, vomiting, peripheral neuropathy, constipation, anemia, asthenia, mucosal inflammation, myalgia, and thrombocytopenia. Refer to the Prescribing Information for pertuzumab for more information.

The safety of intravenous pertuzumab, trastuzumab and docetaxel has been established in patients with HER2 overexpressing metastatic breast cancer. The following adverse reactions have been reported following administration of intravenous pertuzumab and trastuzumab: diarrhea, alopecia, neutropenia, nausea, fatigue, rash, and peripheral neuropathy. Refer to the Prescribing Information for pertuzumab for more information.

6.2 Immunogenicity

As with all therapeutic proteins, there is potential for immunogenicity with PH FDC. The detection of antibody formation is highly dependent on the sensitivity and specificity of the assay. Additionally, the observed incidence of antibody (including neutralizing antibody) positivity in an assay may be influenced by several factors including assay methodology, sample handling, timing of sample collection, concomitant medications, and underlying disease. For these reasons, comparison of the incidence of antibodies to PH FDC and intravenous pertuzumab and trastuzumab in the FeDeriCa study with the incidence of antibodies in other studies or to other products may be misleading.

In the FeDeriCa study, the incidence of treatment-emergent anti-pertuzumab and anti-trastuzumab antibodies in most patients completing 1-4 cycles of therapy was 3% (7/237) and 0.4% (1/237), respectively, in patients treated with intravenous pertuzumab and trastuzumab. The incidence of treatment-emergent anti-pertuzumab, anti-trastuzumab, and anti-recombinant human hyaluronidase PH20 antibodies in most patients completing 1-4 cycles of therapy was 4.8% (11/231), 0.9% (2/232), and 0.9% (2/225), respectively, in patients treated with PH FDC. Among patients who tested positive to anti-pertuzumab antibodies, neutralizing anti-pertuzumab antibodies were detected in one patient treated with intravenous pertuzumab and trastuzumab and in one patient treated with PH FDC. Among patients who tested positive to anti-trastuzumab antibodies, neutralizing anti-trastuzumab antibodies were detected in one patient treated with PH FDC.

The clinical relevance of the development of anti-pertuzumab, anti-trastuzumab or anti-recombinant human hyaluronidase PH20 antibodies after treatment with PH FDC is unknown.

6.3 Postmarketing Experience

The following adverse reactions have been identified with the use of intravenous pertuzumab and trastuzumab. Because these reactions are reported voluntarily from a population of uncertain size, it is not always possible to reliably estimate their frequency or establish a causal relationship to drug exposure.

Glomerulopathy

Immune thrombocytopenia

Tumor lysis syndrome (TLS): Patients with significant tumor burden (e.g. bulky metastases) may be at a higher risk. Patients could present with hyperuricemia, hyperphosphatemia, and acute renal failure which may represent possible TLS. Providers should consider additional monitoring and/or treatment as clinically indicated.

7 Drug Interactions

Patients who receive anthracycline after stopping PH FDC may be at increased risk of cardiac dysfunction because of PH FDC's long washout period [see Clinical Pharmacology (12.3)]. If possible, avoid anthracycline-based therapy for up to 7 months after stopping PH FDC. If anthracyclines are used, carefully monitor the patient's cardiac function.

8 Use in Specific Populations

Patients who receive anthracycline after stopping PH FDC may be at increased risk of cardiac dysfunction because of PH FDC's long washout period [see Clinical Pharmacology (12.3)]. If possible, avoid anthracycline-based therapy for up to 7 months after stopping PH FDC. If anthracyclines are used, carefully monitor the patient's cardiac function.

8.1 Pregnancy

Pregnancy Pharmacovigilance Program

There is a pregnancy pharmacovigilance program for PH FDC. If PH FDC is administered during pregnancy, or if a patient becomes pregnant while receiving PH FDC or within 7 months following the last dose of PH FDC, health care providers and patients should immediately report PH FDC exposure to Genentech at 1-888-835-2555.

Risk Summary

PH FDC can cause fetal harm when administered to a pregnant woman. In post-marketing reports, use of intravenous trastuzumab during pregnancy resulted in cases of oligohydramnios and oligohydramnios sequence manifesting as pulmonary hypoplasia, skeletal abnormalities, and neonatal death (see Data). In an animal reproduction study, administration of pertuzumab to pregnant cynomolgus monkeys during the period of organogenesis resulted in oligohydramnios, delayed fetal kidney development, and embryo-fetal deaths at clinically relevant exposures that were 2.5 to 20-fold greater than exposures in humans receiving the recommended dose, based on $C_{max}$ (see Data). Apprise the patient of the potential risks to a fetus. There are clinical considerations if PH FDC is used during pregnancy or within 7 months prior to conception (see Clinical Considerations).

The estimated background risk of major birth defects and miscarriage for the indicated population is unknown. In the U.S. general population, the estimated background risk of major birth defects and miscarriage in clinically recognized pregnancies is 2-4% and 15-20%, respectively.

Clinical Considerations

Fetal/Neonatal Adverse Reactions

Monitor women who received PH FDC during pregnancy or within 7 months prior to conception for oligohydramnios. If oligohydramnios occurs, perform fetal testing that is appropriate for gestational age and consistent with community standards of care.

Data

Human Data

In post-marketing reports, use of trastuzumab during pregnancy resulted in cases of oligohydramnios and of oligohydramnios sequence, manifesting in the fetus as pulmonary hypoplasia, skeletal abnormalities, and neonatal death. These case reports described oligohydramnios in pregnant women who received trastuzumab either alone or in combination with chemotherapy. In some case reports, amniotic fluid index increased after trastuzumab was stopped. In one case, trastuzumab therapy resumed after amniotic index improved and oligohydramnios recurred.

Animal Data

PH FDC for subcutaneous injection contains pertuzumab, trastuzumab, and hyaluronidase [see Description (11)].

Pertuzumab:

Pregnant cynomolgus monkeys were treated on Gestational Day (GD) 19 with loading doses of 30 to 150 mg/kg pertuzumab, followed by bi-weekly doses of 10 to 100 mg/kg. These dose levels resulted in clinically relevant exposures of 2.5 to 20-fold greater than exposures in humans receiving the recommended dose, based on $C_{max}$. Intravenous administration of pertuzumab from GD19 through GD50 (period of organogenesis) was embryotoxic, with dose-dependent increases in embryo-fetal death between GD25 to GD70. The incidences of embryo-fetal loss were 33, 50, and 85%. At Caesarean section on GD100, oligohydramnios, decreased relative lung and kidney weights, and microscopic evidence of renal hypoplasia consistent with delayed renal development were identified in all pertuzumab dose groups. Pertuzumab exposure was reported in offspring from all treated groups, at levels of 29% to 40% of maternal serum levels at GD100.

Trastuzumab:

In studies where intravenous trastuzumab was administered to pregnant cynomolgus monkeys during the period of organogenesis at doses up to 25 mg/kg given twice weekly (up to 25 times the recommended weekly human dose of 2 mg/kg), trastuzumab crossed the placental barrier during the early (Gestation Days 20 to 50) and late (Gestation Days 120 to 150) phases of gestation. The resulting concentrations of trastuzumab in fetal serum and amniotic fluid were approximately 33% and 25%, respectively, of those present in the maternal serum but were not associated with adverse developmental effects.

Hyaluronidase:

In an embryo-fetal study, mice have been dosed daily by subcutaneous injection during the period of organogenesis with hyaluronidase (recombinant human) at dose levels up to 2,200,000 U/kg, which is >2,400 and 3,600, based on loading and maintenance doses, respectively, times higher than the human dose. The study found no evidence of teratogenicity. Reduced fetal weight and increased numbers of fetal resorptions were observed, with no effects found at a daily dose of 360,000 U/kg, which is >400 and 600, based on loading and maintenance doses, respectively, times higher than the human dose.

In a peri- and post-natal reproduction study, mice have been dosed daily by subcutaneous injection, with hyaluronidase (recombinant human) from implantation through lactation and weaning at dose levels up to 1,100,000 U/kg, which is >1200 and 1,800, based on loading and maintenance doses, respectively, times higher than the human dose. The study found no adverse effects on sexual maturation, learning and memory or fertility of the offspring.

8.2 Lactation

Risk Summary

There is no information regarding the presence of pertuzumab, trastuzumab or hyaluronidase in human milk, the effects on the breastfed infant, or the effects on milk production. Published data suggest that human IgG is present in human milk but does not enter the neonatal and infant circulation in substantial amounts. Trastuzumab was present in the milk of lactating cynomolgus monkeys but not associated with neonatal toxicity (see Data). Consider the developmental and health benefits of breast feeding along with the mother's clinical need for PH FDC treatment and any potential adverse effects on the breastfed child from PH FDC or from the underlying maternal condition. This consideration should also take into account the elimination half-life of pertuzumab and the trastuzumab wash out period of 7 months [see Clinical Pharmacology (12.3)].

Data

In lactating cynomolgus monkeys, trastuzumab was present in breast milk at about 0.3% of maternal serum concentrations after pre- (beginning Gestation Day 120) and post-partum (through Post-partum Day 28) doses of 25 mg/kg administered twice weekly (25 times the recommended weekly human dose of 2 mg/kg of intravenous trastuzumab). Infant monkeys with detectable serum levels of trastuzumab did not exhibit any adverse effects on growth or development from birth to 1 month of age.

8.3 Females and Males of Reproductive Potential

PH FDC can Cause Embryo-Fetal Harm when Administered During Pregnancy.

Pregnancy Testing

Verify the pregnancy status of females of reproductive potential prior to the initiation of PH FDC.

Contraception

Females

Advise females of reproductive potential to use effective contraception during treatment and for 7 months following the last dose of PH FDC [see Use in Specific Populations (8.1) and Clinical Pharmacology (12.3)].

8.4 Pediatric Use

The safety and effectiveness of PH FDC in pediatric patients have not been established.

8.5 Geriatric Use

Of the total number of patients in the FeDeriCa study (n=500) treated with PH FDC, 11% were 65 and over, while 1.6% were 75 and over. Clinical studies of PH FDC did not include sufficient numbers of patients age 65 years and older to determine whether they respond differently from younger patients.

In the intravenous trastuzumab trials, the risk of cardiac dysfunction was increased in geriatric patients as compared to younger patients, in both those receiving treatment for adjuvant therapy or metastatic disease. Other differences in safety or effectiveness were not observed between elderly patients and younger patients. In the intravenous pertuzumab in combination with trastuzumab trials, the risk of decreased appetite, anemia, weight decreased, asthenia, dysgeusia, neuropathy peripheral and hypomagnesemia was increased in patients 65 years of age and older compared to patients less than 65 years of age.

11 Description

PH FDC is a combination of pertuzumab, trastuzumab, and hyaluronidase.

Pertuzumab is a recombinant humanized monoclonal antibody that targets the extracellular dimerization domain (Subdomain II) of the human epidermal growth factor receptor 2 protein (HER2). Pertuzumab is produced by recombinant DNA technology in a mammalian cell (Chinese Hamster Ovary) culture. Pertuzumab has an approximate molecular weight of 148 kDa.

Trastuzumab is a humanized IgG1 kappa monoclonal antibody that selectively binds with high affinity to the extracellular domain of the human epidermal growth factor receptor 2 protein, HER2. Trastuzumab is produced by recombinant DNA technology in a mammalian cell (Chinese Hamster Ovary) culture. Trastuzumab has a molecular weight of approximately 148 kDa.

Hyaluronidase (recombinant human) is an endoglycosidase used to increase the dispersion and absorption of co-administered drugs when administered subcutaneously. It is a glycosylated single-chain protein produced by mammalian (Chinese Hamster Ovary) cells containing a DNA plasmid encoding for a soluble fragment of human hyaluronidase (PH20). Hyaluronidase (recombinant human) has a molecular weight of approximately 61 kDa.

PH FDC (pertuzumab, trastuzumab, and hyaluronidase-zzxf) injection is a sterile, preservative-free, clear to opalescent, and colorless to slightly brownish solution supplied in single-dose vials for subcutaneous administration.

PH FDC injection is supplied as two different configurations:

PH FDC is supplied in a 15 mL single-dose vial containing 1200 mg of pertuzumab, 600 mg of trastuzumab, and 30,000 units of hyaluronidase, and α,α-trehalose (397 mg), L-histidine (6.75 mg), L-histidine hydrochloric monohydrate (53.7 mg), L-methionine (22.4 mg), polysorbate 20 (6 mg), and sucrose (685 mg) with a pH of 5.5.

PH FDC is supplied in a 10 mL single-dose vial containing 600 mg of pertuzumab, 600 mg of trastuzumab, and 20,000 units of hyaluronidase, and α,α-trehalose (397 mg), L-histidine (4.4 mg), L-histidine hydrochloric monohydrate (36.1 mg), L-methionine (14.9 mg), polysorbate 20 (4 mg), and sucrose (342 mg) with a pH of 5.5.

12 Clinical Pharmacology 12.1 Mechanism of Action

Pertuzumab targets the extracellular dimerization domain (subdomain II) of HER2 and, thereby, blocks ligand-dependent heterodimerization of HER2 with other HER family members, including EGFR, HER3 and HER4. As a result, pertuzumab inhibits ligand-initiated intracellular signaling through two major signaling pathways, mitogen-activated protein (MAP) kinase and phosphoinositide 3-kinase (PI3K). Inhibition of these signaling pathways can result in cell growth arrest and apoptosis, respectively.

Trastuzumab binds to subdomain IV of the extracellular domain of the HER2 protein to inhibit the ligand-independent, HER2 mediated cell proliferation and PI3K signaling pathway in human tumor cells that overexpress HER2.

Both pertuzumab and trastuzumab-mediated antibody-dependent cell-mediated cytotoxicity (ADCC) have been shown to be preferentially exerted on HER2 overexpressing cancer cells compared with cancer cells that do not overexpress HER2.

While pertuzumab alone inhibited the proliferation of human tumor cells, the combination of pertuzumab and trastuzumab augmented anti-tumor activity in HER2-overexpressing xenograft models.

Hyaluronan is a polysaccharide found in the extracellular matrix of the subcutaneous tissue. It is depolymerized by the naturally occurring enzyme hyaluronidase. Unlike the stable structural components of the interstitial matrix, hyaluronan has a half-life of approximately 0.5 days. Hyaluronidase increases permeability of the subcutaneous tissue by depolymerizing hyaluronan. In the doses administered, hyaluronidase in PH FDC acts transiently and locally.

The effects of hyaluronidase are reversible and permeability of the subcutaneous tissue is restored within 24 to 48 hours.

Hyaluronidase has been shown to increase the absorption rate of a trastuzumab product into the systemic circulation when given in the subcutis of Göttingen Minipigs.

12.2 Pharmacodynamics

Cardiac Electrophysiology

The effect of intravenous pertuzumab with an initial dose of 840 mg followed by a maintenance dose of 420 mg every three weeks on QTc interval was evaluated in a subgroup of 20 patients with HER2-positive breast cancer (NCT00567190). No large changes in the mean QT interval (i.e., greater than 20 ms) from placebo based on Fridericia correction method were detected in the trial. A small increase in the mean QTc interval (i.e., less than 10 ms) cannot be excluded because of the limitations of the trial design.

The effects of trastuzumab on electrocardiographic (ECG) endpoints, including QTc interval duration, were evaluated in patients with HER2 positive solid tumors. Trastuzumab had no clinically relevant effect on the QTc interval duration and there was no apparent relationship between serum trastuzumab concentrations and change in QTcF interval duration in patients with HER2 positive solid tumors.

12.3 Pharmacokinetics

The pharmacokinetics (PK) of pertuzumab and trastuzumab was characterized in the FeDeriCa study following subcutaneous administration of PH FDC (1200 mg pertuzumab/600 mg trastuzumab initial dose followed by 600 mg pertuzumab/600 mg trastuzumab every 3 weeks) and intravenous administration of pertuzumab and trastuzumab (840 mg pertuzumab/8 mg/kg trastuzumab initial dose followed by 420 mg pertuzumab/6 mg/kg trastuzumab every 3 weeks). The pharmacokinetic parameters of pertuzumab and trastuzumab are described in Table 11. Trastuzumab is estimated to reach concentrations that are <1 mcg/mL by 7 months in at least 95% patients.

Pertuzumab Cycle 7 $C_{trough}$ (i.e., pre-dose cycle 8) showed non-inferiority of pertuzumab within PH FDC (88.7 mcg/mL) to intravenous pertuzumab (72.4 mcg/mL), with a geometric mean ratio of 1.22 (90% CI: 1.14-1.31). Trastuzumab Cycle 7 $C_{trough}$ showed non-inferiority of trastuzumab within PH FDC (58.7 mcg/mL) to intravenous trastuzumab (44.1 mcg/mL), with a geometric mean ratio of 1.33 (90% CI: 1.24-1.43). [see Clinical Studies (14.2)].

A population PK analysis reported that, following subcutaneous administration of PH FDC, the mean Cycle 7 $C_{max}$ and $AUC_{0-21\ days}$ of pertuzumab were 34% lower and 5% higher, respectively, than that following intravenous administration of pertuzumab. The mean Cycle 7 $C_{max}$ and $AUC_{0-21\ days}$ of trastuzumab were 31% lower and 9% higher, respectively, than that following intravenous administration of trastuzumab.

TABLE 11

PK Parameters of Pertuzumab and Trastuzumab Following Subcutaneous Administration of PH FDC *

|  | Pertuzumab[a] | Trastuzumab[b] |
|---|---|---|
| Absorption | | |
| Absolute Bioavailability | 0.7 (18) | 0.8 (13) |
| First-order absorption rate, ka (day$^{-1}$) | 0.4 (8) [†] | 0.4 (2.9) [†] |
| $T_{max}$ (day) | 4 (1-21) [‡] | 4 (1-22) [‡] |
| Distribution | | |
| Volume of Central Compartment (L) | 2.8 (35) | 2.9 (19) |
| Elimination | | |
| Linear Elimination Clearance (L/day) | 0.2 (24) | 0.1 (30) |
| Non-linear Elimination $V_{max}$ (mg/day) | N/A | 12 (20) |
| Non-linear Elimination $K_m$ (mg/L) | N/A | 34 (39) |

* Parameters represented as population mean (intersubject variability) unless otherwise specified
[a] Parameters obtained from FeDeriCa population PK model unless otherwise specified
[b] Parameters obtained from subcutaneous trastuzumab population PK model unless otherwise specified
[†] Residual standard error
[‡] Median (range) values from FeDeriCa study Specific Populations Lean body weight and baseline serum albumin level were included as significant covariates in the pertuzumab population PK model. However, no dose adjustments based on body weight or baseline albumin level are needed, as the exposure changes are not considered clinically relevant.

Body weight showed a statistically significant influence on trastuzumab PK. In patients with a body weight <58 kg, mean Cycle 7 $AUC_{0-21\ days}$ of trastuzumab was about 34% higher after PH FDC than after intravenous trastuzumab treatment, whereas in the highest BW group (>77 kg) Cycle 7 $AUC_{0-21\ days}$ was 24% lower after PH FDC than after intravenous trastuzumab treatment. However, no body weight-based dose adjustments are needed, as the exposure changes are not considered clinically relevant.

No clinically significant differences in the pharmacokinetics of pertuzumab and trastuzumab were observed based on age (25 to 80 years), race (Asian and non-Asian) and renal impairment (creatinine clearance determined by Cockcroft-Gault 30 mL/min or greater). The effects of hepatic impairment on the pharmacokinetics of pertuzumab and trastuzumab are unknown.

Drug Interaction Studies

There have been no formal drug interaction studies performed with PH FDC in humans. Clinically significant interactions among pertuzumab, trastuzumab, and concomitant medications used in clinical trials have not been observed.

13 Nonclinical Toxicology 13.1 Carcinogenesis, Mutagenesis, Impairment of Fertility PH FDC contains pertuzumab, trastuzumab, and hyaluronidase.

Pertuzumab

Studies have not been performed to evaluate the carcinogenicity or mutagenic potential of pertuzumab. No specific fertility studies in animals have been performed to evaluate the effect of pertuzumab.

No adverse effects on male and female reproductive organs were observed in repeat-dose toxicity studies of up to six months duration in cynomolgus monkeys.

Trastuzumab

Trastuzumab has not been tested for carcinogenicity potential.

No evidence of mutagenic activity was observed when trastuzumab was tested in the standard Ames bacterial and human peripheral blood lymphocyte mutagenicity assays at concentrations of up to 5000 mcg/mL. In an in vivo micronucleus assay, no evidence of chromosomal damage to mouse bone marrow cells was observed following bolus intravenous doses of up to 118 mg/kg of trastuzumab.

A fertility study was conducted in female cynomolgus monkeys at doses up to 25 times the weekly recommended human dose of 2 mg/kg of intravenous trastuzumab and has revealed no evidence of impaired fertility, as measured by menstrual cycle duration and female sex hormone levels.

Hyaluronidase

Hyaluronidases are found in most tissues of the body. Long-term animal studies have not been performed to assess the carcinogenic or mutagenic potential of hyaluronidase. In addition, when subcutaneous hyaluronidase (recombinant human) was administered to cynomolgus monkeys for 39 weeks at dose levels up to 220,000 U/kg, which is >223 and 335, based on loading and maintenance doses, respectively, times higher than the human dose, no evidence of toxicity to the male or female reproductive system was found through periodic monitoring of in-life parameters, e.g., semen analyses, hormone levels, menstrual cycles, and also from gross pathology, histopathology and organ weight data.

14 Clinical Studies 14.1 Neoadjuvant and Adjuvant Treatment of Breast Cancer

The effectiveness of PH FDC for use in combination with chemotherapy has been established for the treatment of patients with HER2-positive early breast cancer. Use of PH FDC for this indication is supported by evidence from adequate and well-controlled studies conducted with intravenous pertuzumab and intravenous trastuzumab administered in combination with chemotherapy in adults with HER2-overexpressing early breast cancer (NCT00545688, NCT00976989, NCT02132949, NCT01358877) and additional pharmacokinetic and safety data that demonstrated comparable pharmacokinetics and safety profiles between PH FDC and intravenous pertuzumab and intravenous trastuzumab in FeDeriCa [see Adverse Reactions (6.1) and Clinical Pharmacology (12.3)].

FeDeriCa

The FeDeriCa study (NCT03493854) was an open-label, multicenter, randomized study conducted in 500 patients with operable or locally advanced (including inflammatory) HER2-positive breast cancer with a tumor size >2 cm or node-positive. HER2 overexpression was defined as IHC 3+ in >10% of immunoreactive cells or HER2 gene amplification by ISH (ratio of HER2 gene signals to centromere 17 signals ≥2.0) using an FDA-approved test. Patients were randomized to receive 8 cycles of neoadjuvant chemotherapy with concurrent administration of 4 cycles of either PH FDC or intravenous pertuzumab and trastuzumab during cycles 5-8, followed by surgery. Investigators selected one of two of the following neoadjuvant chemotherapy regimens for individual patients:

- 4 cycles of doxorubicin (60 mg/m$^2$) and cyclophosphamide (600 mg/m$^2$) every 2 weeks followed by paclitaxel (80 mg/m$^2$) weekly for 12 weeks
- 4 cycles of doxorubicin (60 mg/m$^2$) and cyclophosphamide (600 mg/m$^2$) every 3 weeks followed by 4 cycles of docetaxel (75 mg/m$^2$ for the first cycle and then 100 mg/m$^2$ at subsequent cycles at the investigator's discretion) every 3 weeks Following surgery, patients continued therapy with PH FDC or intravenous pertuzumab and trastuzumab as treated prior to surgery, for an additional 14 cycles, to complete 18 cycles of anti-HER2 therapy. Patients also received adjuvant radiotherapy and endocrine therapy as per investigator's discretion. In adjuvant period, substitution of intravenous trastuzumab for subcutaneous trastuzumab was permitted at investigator discretion. Patients received HER2-targeted therapy every 3 weeks according to Table 12 as follows:

TABLE 12

Dosing and Administration of PH FDC, Intravenous Pertuzumab, Intravenous Trastuzumab, and Subcutaneous Trastuzumab

| Medication | Administration | Dose Initial | Dose Maintenance |
|---|---|---|---|
| PH FDC | Subcutaneously | 1200 mg/600 mg | 600 mg/600 mg |
| Pertuzumab | Intravenously | 840 mg | 420 mg |
| Trastuzumab | Intravenously | 8 mg/kg | 6 mg/kg |
| Trastuzumab-oysk | Subcutaneously* | 600 mg | |

*In adjuvant period substitution of intravenous trastuzumab for subcutaneous trastuzumab was permitted at investigator discretion FeDeriCa was designed to demonstrate non-inferiority of the Cycle 7 (i.e., pre-dose Cycle 8) pertuzumab serum $C_{trough}$ from PH FDC pertuzumab to the intravenous pertuzumab (primary endpoint) [see Clinical Pharmacology 12.3]. Secondary endpoints included Cycle 7 serum trastuzumab $C_{trough}$, efficacy (pathological complete response [pCR], defined as the absence of invasive neoplastic cells in the breast and in the axillary lymph nodes), and safety. The median age was 51 years (range: 25-81), and the majority of patients were White (66%). The majority of patients had hormone receptor-positive disease (61%) or node-positive disease (58%).

The pCR rate was 59.7% (95% CI: 53.3, 65.8) in the PH FDC arm and 59.5% (95% CI: 53.2, 65.6) in the intravenous pertuzumab and trastuzumab arm.

TABLE 13

Summary of Pathological Complete Response (pCR) (FeDeriCa)

| | PH FDC n = 248 | Intravenous pertuzumab + trastuzumab n = 252 |
|---|---|---|
| pCR (ypT0/is, ypN0) | 148 (59.7%) | 150 (59.5%) |
| Exact 95% CI for pCR Rate[1] | (53.3%, 65.8%) | (53.2%. 65.6%) |
| Difference in pCR rate (SC minus IV arm) | 0.15% | |
| 95% CI for the difference in pCR[2] rate | (−8.7%; 9.0%) | |

[1]Confidence interval for one sample binomial using Pearson-Clopper method
[2]Hauck-Anderson continuity correction has been used in this calculation 14.2 Metastatic Breast Cancer The effectiveness of PH FDC for use in combination with docetaxel has been established for the treatment of patients with HER2-positive metastatic breast cancer who have not received prior anti-HER2 therapy or chemotherapy for metastatic disease. Use of PH FDC for this indication is supported by evidence from adequate and well-controlled studies conducted with intravenous pertuzumab and intravenous trastuzumab administered in combination with chemotherapy in adults with HER2-overexpressing metastatic breast cancer (NCT00567190) and additional pharmacokinetic and safety data that demonstrated comparable pharmacokinetics and safety profiles between PH FDC and intravenous pertuzumab and intravenous trastuzumab in FeDeriCa [see Adverse Reactions (6.1), Clinical Pharmacology (12.3), and Clinical Studies (14.2)].

14.3 Patient Experience

The PHranceSCa study (NCT03674112) was a randomized, multi-center, open-label cross-over trial conducted in 160 patients with HER2-positive breast cancer undergoing adjuvant treatment. All patients completed neoadjuvant treatment with pertuzumab, trastuzumab and chemotherapy and had surgery before randomization. Following randomization, 80 patients in arm A received 3 cycles of intravenous pertuzumab and trastuzumab followed by 3 cycles of PH FDC and 80 patients in arm B received 3 cycles of PH FDC followed by 3 cycles of intravenous pertuzumab and trastuzumab. All patients received 18 total cycles of HER2-targeted therapy. After Cycle 6, 136 out of 160 patients (85%) reported preferring subcutaneous administration of PH FDC over intravenous pertuzumab and trastuzumab and the most common reason was that administration required less time in the clinic. After Cycle 6, 22 out of 160 patients (14%) reported preferring intravenous pertuzumab and trastuzumab over PH FDC and the most common reason was feels more comfortable during administration. Two out of 160 patients (1%) had no preference for the route of administration. All 160 patients (100%) completed the preference questionnaire 16 How Supplied/Storage and Handling 16.1 How Supplied PH FDC (pertuzumab, trastuzumab, and hyaluronidase-zzxf) injection is a sterile, preservative-free, clear to opalescent, and colorless to slightly brownish solution in single-dose vials for subcutaneous administration supplied as each carton containing one single-dose vial:

- 1200 mg pertuzumab, 600 mg trastuzumab, and 30,000 units hyaluronidase/15 mL (80 mg, 40 mg, and 2,000 units/mL) (NDC 50242-245-01).
- 600 mg pertuzumab, 600 mg trastuzumab, and 20,000 units hyaluronidase/10 mL (60 mg, 60 mg, 2,000 units/mL) (NDC 50242-260-01).

16.2 Storage and Handling

Store PH FDC vials in the refrigerator at 2° C. to 8° C. (36° F. to 46° F.) in the original carton to protect from light.

Do not freeze. Do not shake.

17 Patient Counseling Information

Cardiomyopathy

Advise patients to contact a health care professional immediately for any of the following: new onset or worsening shortness of breath, cough, swelling of the ankles/legs, swelling of the face, palpitations, weight gain of more than 5 pounds in 24 hours, dizziness or loss of consciousness [see Warnings and Precautions (5.1)].

Embryo-Fetal Toxicity

Advise pregnant women and females of reproductive potential that exposure to PH FDC during pregnancy or within 7 months prior to conception can result in fetal harm. Advise female patients to contact their healthcare provider with a known or suspected pregnancy [see Use in Specific Populations (8.1)].

Advise women who are exposed to PH FDC during pregnancy or within 7 months prior to conception that there is a pregnancy pharmacovigilance program that monitors pregnancy outcomes. Encourage these patients to report their pregnancy to Genentech [see Use in Specific Populations (8.1)].

Advise females of reproductive potential to use effective contraception during treatment and for 7 months following the last dose of PH FDC [see Use in Specific Populations (8.3

Hypersensitivity and Administration-Related Reactions

Advise patients to contact their healthcare provider immediately and to report any symptoms of hypersensitivity and administration-related reactions including dizziness, nausea, chills, fever, vomiting, diarrhea, urticaria, angioedema, breathing problems, or chest pain [see Warnings and Precautions (5.5)].

Figure 15:
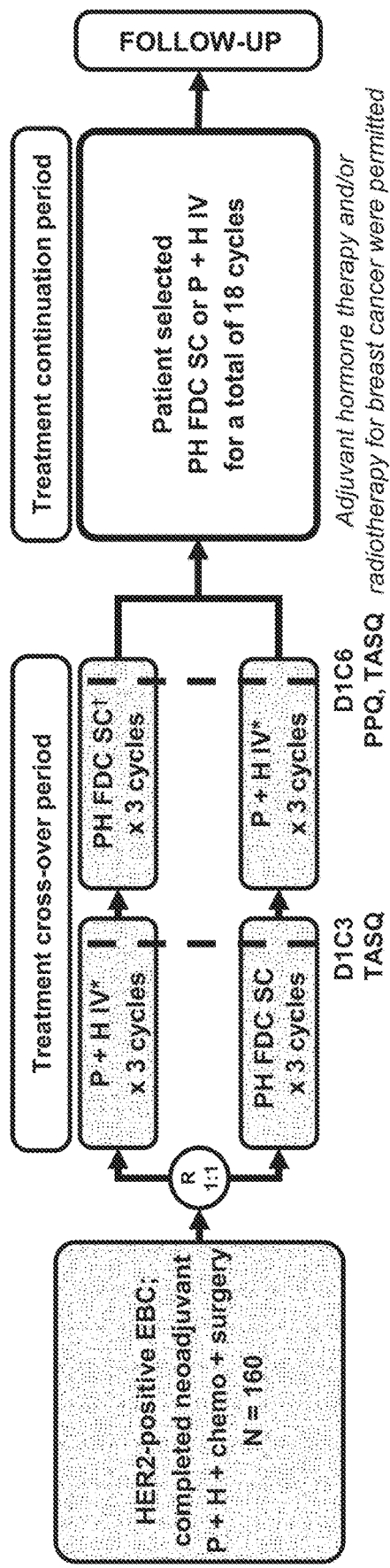
FIG. 15 depicts the PHranceSCa Protocol in Example 3. All patients were female; median age was 49 years. †P IV loading dose if needed: 840 mg; maintenance: 420 mg q3w. H IV loading dose if needed: 8 mg/kg; maintenance: 6 mg/kg IV q3w. †PH FDC SC loading dose if needed: P 1200 mg/H 600 mg in 15 mL; maintenance: P 600 mg/H 600 mg in 10 mL q3w. Loading doses were only required for patients who had ≥6 weeks since their last neoadjuvant dose of P+H IV at study entry, or had ≥6 weeks since their last study treatment during the study. Maintenance doses were used for subsequent administrations or dose delays <6 weeks. H, trastuzumab; HCP, healthcare professional; HR, hormone receptor; IV, intravenous; NACT, neoadjuvant chemotherapy; P, pertuzumab; PH FDC SC, fixed-dose combination of pertuzumab and trastuzumab for subcutaneous injection; PPQ, Patient Preference Questionnaire; SC, subcutaneous; TASQ, Therapy Administration Satisfaction Questionnaire.

Example 3: Primary Analysis of the Open-Label, Randomized Crossover PHranceSCa Study PHranceSCa was an open-label, randomized cross-over study for PH FDC SC versus P+H IV. The protocol was posted as NCT03674112 Sep. 18, 2018. Patients had HER2-positive EBC and had completed neoadjuvant P IV+H IV+chemo+surgery and were treated as shown in FIG. 15.

Primary and Secondary Objectives:

Primary Objective:

Patient preference for PH FDC SC

Key Secondary Objectives:

Patient satisfaction

Patients' choice of formulation for the continuation period health-related quality of life, HCP perception on time/resource, safety and tolerability (including safety of switching from SC to IV formulations and vice-versa), efficacy Stratification Factors:

NACT regimen pCR vs non-pCR

HR status

Patient Preference

Figure 16:
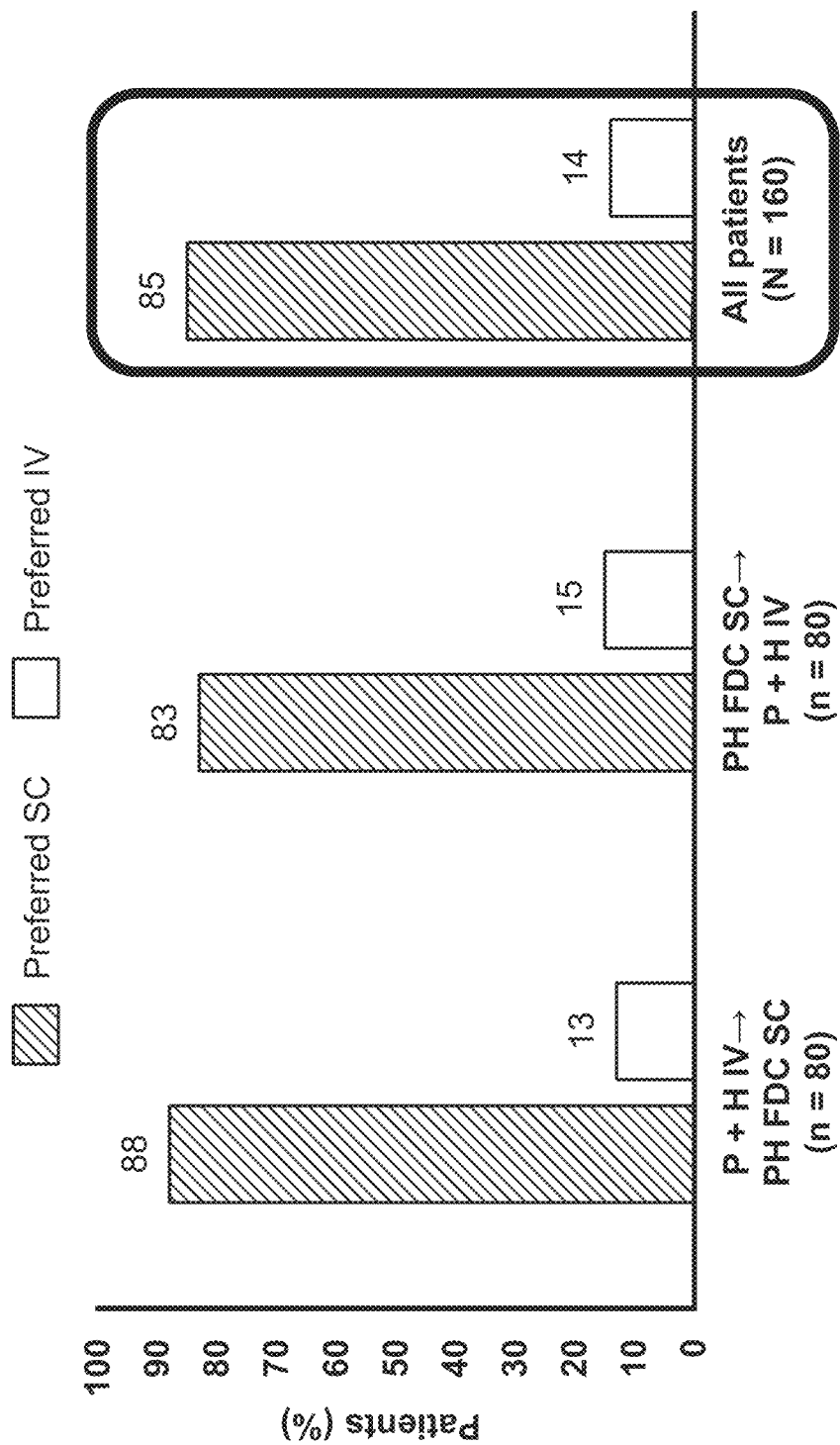
FIG. 16 depicts primary analysis of patient preference for PHranceSCa. CI, confidence interval; H, trastuzumab; IV, intravenous; P, pertuzumab; PH FDC SC, fixed-dose combination of pertuzumab and trastuzumab for subcutaneous injection; PPQ, Patient Preference Questionnaire; SC, subcutaneous.

FIG. 16 depicts patient preference at the primary analysis. At the primary analysis, 85% of patients (95% CI: 79-90) preferred PH FDC SC, regardless of sequencing. The PPQ Q1 was: "All things considered, which method of administration did you prefer?" Main reasons for SC preference were:

Less time in clinic (42%)

More comfortable during administration (26%)

The findings at the primary analysis were consistent with the interim analysis (O'Shaughnessy J, et al. ESMO Breast Cancer Virtual Meeting 2020; abstract 800). The PPQ findings were consistent with treatment continuation choice: 87% PH FDC SC vs 13% P+H IV.

Safety Data

FIG. 17 reports adverse events at the primary analysis of PHranceSCa. No new safety signals observed with PH FDC SC at the primary analysis, and AEs were in line with previous studies of P+H IV (von Minckwitz G, et al. N Engl J Med 2017; 377:122-131; Baselga J, et al. N Engl J Med 2012; 366:109-119) and PH FDC SC (Tan A R, et al. SABCS 2019, Abstract PD4-07). There was a low incidence of SAEs and grade ≥3 AEs with PH FDC SC across both treatment periods. No grade 4 or 5 AEs had been reported during the study at the clinical cut-off date. There were more injection site reactions with PH FDC SC, as expected (all grade 1 or 2), with no discontinuations due to local injection site reactions with PH FDC SC.

FIG. 18 reports AEs at the primary analysis before and after switching. AE rates before and after switching were similar (P+H IV→PH FDC SC: 78%→73%; PH FDC SC→P+H IV: 78%→64%), with no new safety signals. These data support the approved use for PH FDC SC following P+H IV as included in the USPI in Example 2.

Example 4: Fixed Dose Combination (FDC) Anti-Drug Antibody (ADA) Assay

The clinical anti-drug antibody (ADA) strategy included the use of validated assays to detect ADAs to pertuzumab and trastuzumab in serum and ADAs to rHuPH20 in plasma samples from patients in FeDeriCa.

The ADA assay strategy used a tiered approach for analysis. Samples were tested using a panel of validated assays, in a sequential fashion, to screen, confirm, and titer the antibody response in human matrix.

Each panel of method was used in the following manner:

a. Antibody screening assays to detect ADAs to pertuzumab and trastuzumab in serum samples or ADAs to rHuPH20 in plasma samples.

b. Confirmatory assays to assess the specificity of the screen-positive results by competition with excess pertuzumab, trastuzumab, or rHuPH20.
c. Titration assays to determine the antibody titers for confirmed positive samples.

Samples that were positive in the confirmatory assays for ADAs to pertuzumab, trastuzumab, and rHuPH20 will be further analyzed for neutralizing activity.

ELISA Method for the Detection of Antibodies to Pertuzumab

ADAs to pertuzumab in human serum were detected using a validated enzyme-linked immunosorbent assay (ELISA) method that was based on the formation of bridging antibody complexes with labeled pertuzumab molecules. This assay used two conjugated reagents, biotin-conjugated pertuzumab and digoxin (DIG)-conjugated pertuzumab, to capture ADAs directed against pertuzumab. Bound ADAs to pertuzumab were then detected with a mouse anti-DIG antibody conjugated with horseradish peroxidase (HRP). A peroxidase substrate (tetramethyl benzidine) was used for color development.

The specificity of the immune response for samples that screened positive for ADA was confirmed by competitive binding with pertuzumab. The ADA confirmatory assay used the same bridging ELISA as the screening assay.

Confirmed positive samples underwent titration analysis. During the titration assay, samples were diluted to the minimum required dilution followed by sufficient ½ serial dilutions prior to analysis, such that the dilution series had at least one dilution below the cut point. Antibody titer values were reported as the log 10 of the endpoint dilution factor. The minimum reportable titer value was 1.30 titer units.

Data from 493 baseline samples (i.e. pertuzumab-naïve individuals) from FeDeriCa were used to establish the screening cut point for FeDeriCa. To minimize the potential for false negative results, the screening cut point was set to give an untreated positive rate of approximately 5%, which was determined to be 0.735. Data from 100 baseline samples from FeDeriCa were used to establish the confirmatory cut point for FeDeriCa, which was set to give an untreated positive rate of approximately 1% and determined to be 13.5%. Using an anti-idiotypic MAb directed against pertuzumab as the positive control, the relative sensitivity for the screening assay and confirmatory assay for FeDeriCa were determined to be 3.59 ng/mL and 0.598 ng/mL, respectively.

The validation parameters are summarized in Table 14.

TABLE 14

Summary of Validated Assay Used to Detect ADAs to Pertuzumab

| | |
|---|---|
| Assay | Pertuzumab ADA ELISA |
| Biological Matrix | Human Serum |
| Positive Control | Anti-idiotypic MAb to pertuzumab |
| Minimum Dilution | 1:20 |
| Screen Cut Point factor | 0.735 |
| Confirmatory Cut Point | 13.5% |
| Relative Sensitivity (screening assay) | 3.59 ng/mL |
| Relative Sensitivity (confirmatory assay) | 0.589 ng/mL |
| Positive Control concentrations (screening assay) | 5 ng/mL (Low) 50 ng/mL (High) |
| Positive Control Concentrations (confirmatory assay) | 2.65 ng/mL (low) 50 ng/mL (high) |
| Drug Tolerance (Screening and confirmatory assay) | ≤200 µg/mL (in the presence of up to 200 µg/mL of pertuzumab, the assay can detect 100 ng/mL of the surrogate anti-idiotypic MAb to pertuzumab). |
| Minimum Reportable Titer | Log10(minimum dilution) = 1.30 titer units |
| Inter-Assay Precision Range (% CV) for screening assay | 1.97 to 27.7 |
| Intra-Assay Precision Range (% CV) for screening assay | 0 to 15.2 |
| Inter-Assay Precision Range (% CV) for confirmatory assay | 1.04 to 6.07 |
| Intra-Assay Precision Range (% CV) for confirmatory assay | 0.129 to 15.8 |
| Recovery | Acceptable in individual breast cancer serum samples |
| Interference/Cross-reactivity | Interfering: recombinant human HER2 ECD ≥4000 ng/mL Non-interfering: hemoglobin (at 10% hemolyzed human serum), lipids (up to 500 mg/dL), and trastuzumab (≤200 µg/mL) Cross-reactive: recombinant human HER2 ECD ≥100 ng/mL; PAbs to the framework of trastuzumab. Non-cross-reactive: trastuzumab up to 200 µg/mL; anti-CDR MAb to trastuzumab at 1.7 mg/mL |
| Studies | FeDeriCa |

CV = coefficient of variation; ECD = extracellular domain; HER2 = human epidermal growth factor receptor 2; IA = immunoaffinity; LLOQ = lower limit of quantification; LC-MS/MS = liquid chromatography tandem mass spectrometry; MAb = monoclonal antibody; PAb = polyclonal antibody; PK = pharmacokinetic.

ELISA Method for the Detection of Antibodies to Trastuzumab

ADAs to trastuzumab in human serum were detected using a validated ELISA that was based on the formation of bridging antibody complexes with labeled trastuzumab molecules. The assay used two conjugated reagents, biotin-conjugated trastuzumab and DIG-conjugated trastuzumab, to capture ADAs directed against trastuzumab. Bound ADAs to trastuzumab were then detected with a mouse anti-DIG antibody conjugated with HRP. A peroxidase substrate (tetramethyl benzidine) was used for color development.

The specificity of the immune response for samples that screened positive for ADA was confirmed by competitive binding with trastuzumab. The ADA confirmatory assay used the same bridging ELISA as the screening assay.

Confirmed ADA positive samples underwent titration analysis. During the titration assay, ADA positive samples were diluted to the minimum required dilution followed by sufficient ½ serial dilutions prior to analysis such that the dilution series had at least one dilution below the cut point. For the assay method used in FeDeriCa, antibody titer values were reported as the log 10 of the endpoint dilution factor. The minimum reportable titer value was 1.30 titer units.

For assay method used in FeDeriCa, data from 100 baseline samples (i.e., trastuzumab-naïve individuals) from FeDeriCa were used to establish the screening cut point. To minimize the potential for false negative results, the screening cut point was set to give an untreated positive rate of approximately 5%, which was determined to be 0.995. Data from the same panel of baseline samples from FeDeriCa were used to establish the confirmatory cutpoint, which was set to give an untreated positive rate of approximately 1% and determined to be 31.2%. Using rabbit polyclonal IgG antibodies against trastuzumab as the positive control, the relative sensitivity for the screening assay and confirmatory assay for FeDeriCa were determined to be 14.6 ng/mL and 8.06 ng/mL, respectively. The validation parameters are summarized in Table 15.

ECLA Method for the Detection of Antibodies to rHuPH20

ADAs to rHuPH20 in human plasma were detected using an ECL immunoassay method with the Meso Scale Discovery platform technology. The assay used two conjugated reagents, ruthenylated (sulfo-tagged) rHuPH20 and biotinylated rHuPH20, to capture ADAs directed against rHuPH20. Detection of anti-rHuPH20 binding antibodies was based on the bivalent characteristics of the antibody. The immobilized complexes of anti-rHuPH20 antibodies with the labeled rHuPH20 was detected with tripropylamine to produce a chemiluminescent signal that is proportional to the amount of anti-rHuPH20 antibodies present in the sample.

The specificity of the immune response for samples that screened positive for ADA was confirmed by competitive binding with unlabeled rHuPH20. The ADA confirmatory assay used the same ECL immunoassay as the screening assay.

Confirmed ADA positive samples underwent titration analysis. The magnitude of the confirmed antibody response was determined by serial dilution that results in an endpoint titer value defined as the dilution factor at or above the plate-specific cut point. The minimum reportable titer value was 5.

Data from a panel of 50 normal individual human K3EDTA plasma samples were used to establish the assay decision threshold, or screening cut point. To minimize the potential for false negative results, the screening cut point was set to give an untreated positive rate of approximately 5%, which was determined to be 1.17 and the confirmatory cut point (used to confirm the positive screen response via

TABLE 15

Summary of Validated Assay Used to Detect ADAs to Trastuzumab (FeDeriCa)

| | |
|---|---|
| Assay | Pertuzumab ADA ELISA |
| Biological Matrix | Human Serum |
| Positive Control | Anti-idiotypic MAb to pertuzumab |
| Minimum Dilution | 1:20 |
| Screen Cut Point factor | 0.735 |
| Confirmatory Cut Point | 13.5% |
| Relative Sensitivity (screening assay) | 3.59 ng/mL |
| Relative Sensitivity (confirmatory assay) | 0.589 ng/mL |
| Positive Control concentrations (screening assay) | 5 ng/mL (Low) 50 ng/mL (High) |
| Positive Control Concentrations (confirmatory assay) | 2.65 ng/mL (low) 50 ng/mL (high) |
| Drug Tolerance (Screening and confirmatory assay) | ≤200 µg/mL (in the presence of up to 200 µg/mL of pertuzumab, the assay can detect 100 ng/mL of the surrogate anti-idiotypic MAb to pertuzumab). |
| Minimum Reportable Titer | Log10(minimum dilution) = 1.30 titer units |
| Inter-Assay Precision Range (% CV) for screening assay | 1.97 to 27.7 |
| Intra-Assay Precision Range (% CV) for screening assay | 0 to 15.2 |
| Inter-Assay Precision Range (% CV) for confirmatory assay | 1.04 to 6.07 |
| Intra-Assay Precision Range (% CV) for confirmatory assay | 0.129 to 15.8 |
| Recovery | Acceptable in individual breast cancer serum samples |

CV = coefficient of variation; ECD = extracellular domain; HER2 = human epidermal growth factor receptor 2; IA = immunoaffinity; LLOQ = lower limit of quantification; LC-MS/MS = liquid chromatography tandem mass spectrometry; MAb = monoclonal antibody; PAb = polyclonal antibody; PK = pharmacokinetic.

competitive binding with rHuPH20) was set to give an untreated positive rate of approximately 1%, which was determined to be 32%. Using rabbit polyclonal IgG antibodies against rHuPH20 as the positive control, the relative sensitivity for the screening assay and confirmatory assay were determined to be 0.697 ng/mL and 1.21 ng/mL, respectively. The validation parameters are summarized in Table 16.

TABLE 16

Summary of Validated Assay Used to Detect ADAs to rHuPH20

| | |
|---|---|
| Assay | rHuPH20 ADA ECLA |
| Biological Matrix | Human $K_3$-EDTA Plasma |
| Positive Control | Rabbit polyclonal IgG antibodies against rHuPH20 (purified) |
| Minimum Dilution | 1:5 |
| Screen Cut Point Factor | 1.17 |
| Confirmatory Cut Point | 32% |
| Relative Sensitivity (screening assay) | 0.697 ng/mL |
| Relative Sensitivity (confirmatory assay) | 1.21 ng/mL |
| Positive Control Concentrations (screening and confirmatory assay) | 1.48 ng/mL and 20 ng/mL (Low controls for screening assay) 2.58 ng/mL and 20 ng/mL (Low controls for confirmatory assay) 5000 ng/mL (High control for screening and confirmatory assay) |
| Drug Tolerance (Screening assay) | 1 μg/mL (in the presence of up to 1 μg/mL of rHuPH20, the assay can detect 20 ng/mL of the surrogate PAbs to rHuPH20) |
| Minimum Reportable Titer | 5 |
| Inter-Assay Precision Range (% CV) for screening assay | 6.64 to 17.2 |
| Intra-Assay Precision Range (% CV) for screening assay | 0.435 to 9.18 |
| Interference | Non-interfering: ≤250 μg/mL of pertuzumab, ≤250 μg/mL trastuzumab; hemoglobin (with 5% hemolysate), lipids (with 2% intralipid) |
| Selectivity | Acceptable in breast cancer $K_3$EDTA plasma matrix |
| Studies | FeDeriCa |

ADA = anti-drug antibody; CV = coefficient of variation; ECLA = electrochemiluminescence assay; $K_3$EDTA = tripotassium ethylenediaminetetraacetic acid; rHuPH20 = recombinant human hyaluronidase;

Neutralizing Antibody (NAb) Assay

ELISAs were validated for the detection of anti-pertuzumab and anti-trastuzumab NAbs and a hyaluronidase activity assay was validated to detect anti-rHuPH20 NAbs.

Pertuzumab NAb Assay

Figure 19:
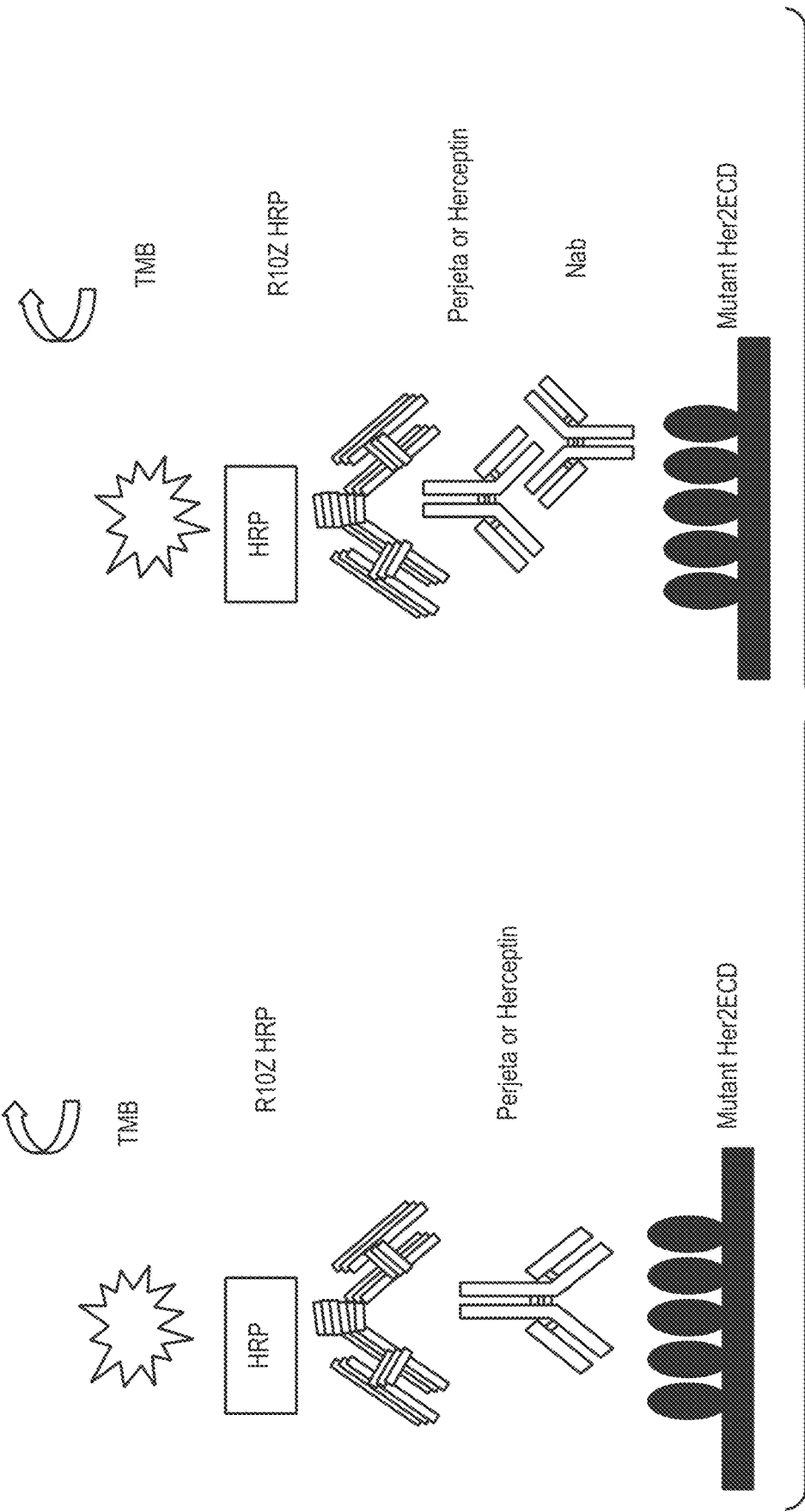
FIG. 19 depicts pertuzumab and trastuzumab neutralizing anti-drug antibody (ADA) assay. ECD=extracellular domain; HER2=human epidermal growth factor receptor 2 HRP=horseradish peroxidase; NAb=neutralizing antibody; TMB=tetramethylbenzidine peroxidase. Notes: the figure on the left shows the assay when NAb is not detected in the sample. The figure on the right shows the assay when NAb is detected. For the pertuzumab NAb assay, the trastuzumab domain is removed from the mutant HER2 ECD and, for the trastuzumab NAb assay, the pertuzumab domain is removed.

The pertuzumab NAb assay is a qualitative assay designed to detect NAbs directed against pertuzumab in human serum using a magnetic bead extraction with acid dissociation treatment prior to an ELISA. An affinity purified mouse mAb against pertuzumab from hyperimmunized BALB/c mice was used as the source for the positive controls. NAb controls (normalization control [NC], low-positive control [LPC], and high-positive control [HPC]) and study samples were incubated in 2 M acetic acid to dissociate anti-pertuzumab antibodies from pertuzumab. The dissociated samples were neutralized with a 2 M Tris-HCl solution containing biotinylated pertuzumab and room-temperature incubation. The anti-pertuzumab antibodies were captured by binding to biotinylated pertuzumab and immobilized on streptavidin-coated magnetic beads. This bead complex was then isolated with a magnet and washed. Next, the antibodies were released from the bead complex with an acidic solution containing 100 mM glycine HCl/150 mM NaCl. Then the acidic sample and NAb control solutions were neutralized with 100 mM Trizma Base and incubated overnight with 20.0 ng/mL pertuzumab (final drug concentration in a sample was 10.0 ng/mL). Following the overnight incubation, the neutralized NAb controls and study samples were transferred to a pre-coated and pre-blocked ELISA plate and incubated. During the incubation, pertuzumab in the sample bound to the immobilized mutant HER2 ECD that was specific for pertuzumab binding only. The presence of NAbs in the samples blocks the binding of pertuzumab to the mutant HER2 ECD, which results in a decrease in absorbance readings. Unbound material was removed with a wash step. Horseradish peroxidase (HRP) conjugated to anti-human IgG fragment crystallizable (Fc; Fcγ-pan:10061 [R10Z8E9]) was then added to the plate and incubated. Finally, tetramethylbenzidine peroxidase (TMB) substrate was added to develop color. The substrate development was stopped with the addition of 1 M phosphoric acid. The plate was read on a plate reader at 450 nm for detection absorbance and at 630 nm for reference absorbance. See FIG. 19.

The minimum required dilution (MRD) for this assay was determined to be ½ and all study samples were analyzed at the assay MRD. Samples with raw optical density (OD) responses at or below the cutpoint (mean NC×established cutpoint factor, 0.903) were considered NAb positive, whereas samples with raw OD responses above the cutpoint were considered negative. The presence of pertuzumab in the sample may interfere with the detection of NAbs in the assay, where it was determined that the assay can detect 500 ng/mL of the surrogate positive source material in the presence of up to 50 μg/mL of pertuzumab.

Trastuzumab NAb Assay

The trastuzumab NAb assay is a qualitative assay designed to detect NAbs directed against trastuzumab in human serum using a magnetic bead extraction with acid dissociation treatment prior to an ELISA. An affinity purified rabbit polyclonal antibody against trastuzumab from hyperimmunized New Zealand White rabbits was used as the source for the positive controls. NAb controls (NC, LPC, and HPC) and study samples were incubated in 2 M acetic acid to dissociate anti-trastuzumab antibodies from trastuzumab. The dissociated samples were neutralized with a 2 M Tris-HCl solution containing biotinylated trastuzumab and room-temperature incubation. The anti-trastuzumab antibodies were captured by binding to biotinylated trastuzumab and immobilized on streptavidin-coated magnetic beads. This bead complex was then isolated with a magnet and washed. Next, the antibodies were released from the bead complex with an acidic solution containing 100 mM glycine HCl/150 mM NaCl. Then the acidic sample and NAb control solutions were neutralized with 100 mM Trizma Base and incubated overnight with 24.0 ng/mL trastuzumab (final drug concentration in a sample was 12.0 ng/mL). Following the overnight incubation, the neutralized NAb controls and study samples were transferred to a pre-coated and pre-blocked ELISA plate and incubated. During the incubation, trastuzumab in the sample bound to the immobilized mutant HER2 ECD that was specific for trastuzumab binding only. The presence of NAbs in the samples blocks the binding of trastuzumab to the mutant HER2 ECD, which results in a decrease in absorbance readings. Unbound material was removed with a wash step. HRP conjugated to anti-human IgG Fc (Fcγ-pan:10061 [R10Z8E9]) was then added to the plate and incubated. Finally, TMB substrate was added to develop color. The substrate development was stopped with the addition of 1 M phosphoric acid. The plate was read on a plate reader at 450 nm for detection absorbance and at 630 nm for reference absorbance.

The MRD for this assay was determined to be ½ and all study samples were analyzed at the assay MRD. Samples with raw OD responses at or below the cutpoint (mean NC×established cutpoint factor, 0.905) were considered NAb positive, whereas samples with raw OD responses above the cutpoint were considered negative. The presence of trastuzumab in the sample may interfere with the detection of NAbs in the assay, where it was determined that the assay can detect 500 ng/mL of the surrogate positive source material in the presence of up to 100 μg/mL of trastuzumab.

rHuPH20 NAb Assay

The method for the detection of antibodies present in human K3EDTA plasma capable of neutralizing rHuPH20 activity in vitro is an endpoint assay. The assay measures the ability of antibodies present in human plasma samples to neutralize the in vitro hyaluronidase function of rHuPH20 by measuring the reduction in hydrolysis of a biotinylated hyaluronan substrate of large molecular weight (approximately 1.2 MDa) non-covalently bound to plastic, multi-well microtiter plates. A neutralizing, polyclonal rabbit, anti-rHuPH20 IgG was used as an assay-positive control at three quality-control levels; pooled human plasma served as the negative control. The test plasma and positive and negative controls were diluted to the assay MRD (1/100) and then pre-incubated with a defined concentration of rHuPH20 to allow for binding of anti-rHuPH20 NAbs. After the pre-incubation period, samples were transferred into individual wells in a microtiter plate that was coated with biotinylated hyaluronan. After a fixed period of enzymatic reaction, all unbound complexes were washed away, and the remaining bound, biotinylated hyaluronan was detected by addition of HRP conjugated to streptavidin and, subsequently, a TMB substrate. Color development in each well was inversely proportional to the activity of rHuPH20, was measured using a microplate spectrophotometer, and was reported as optical density at 450 nm.

The NAb cutpoint factor with a 0.1% false-positive error rate (FPER) was determined to be 4.275. Later, with a low-concentration, positive-control sample, the 1.0% FPER was established. After SC dosing, rHuPH20 is not detected in circulation, therefore, there is no potential for drug interference.

ADA/NAB Results

Figure 20:
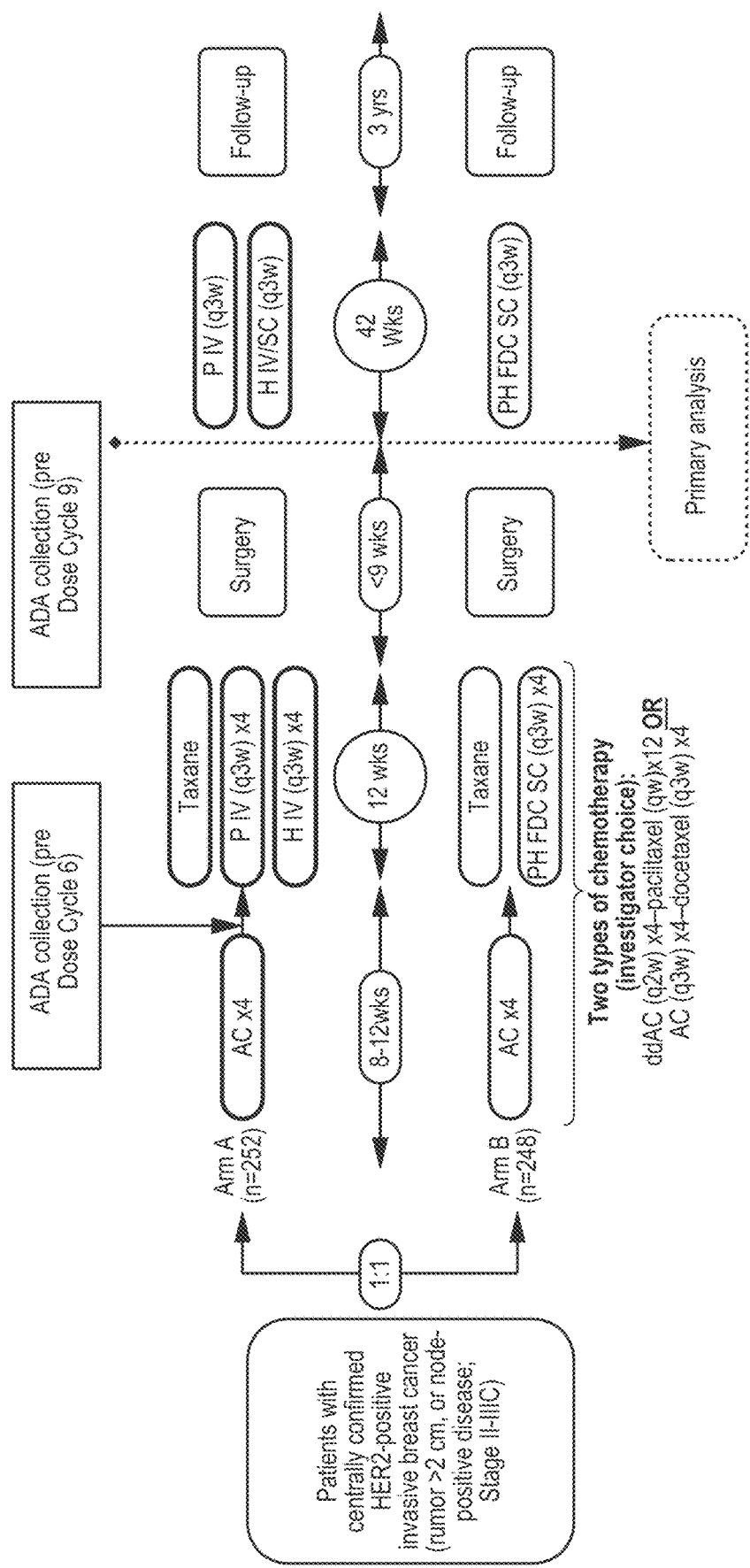
FIG. 20 depicts key anti-drug antibody (ADA) collection timepoints during the FeDeriCa study.

The incidence of treatment-emergent ADAs was comparable between both the P+H IV and PH FDC SC treatment arms. The key ADA collection timepoints are shown in FIG. 20, with a first timepoint being predose Cycle 6, and a second timepoint predose Cycle 9. Additional ADA collection timepoints analyzed were predose Cycle 13 (during the adjuvant phase) and 3 months follow up (no specific phase) (1 ADA test at predose Cycle 13 timepoint and 4 ADA tests at 3 months follow up timepoint out of 231, 232, and 225 patients for anti-pertuzumab, anti-trastuzumab, and anti-rHuPH20, respectively). In the P+H IV arm, the incidence of treatment-emergent ADAs to pertuzumab and trastuzumab was 3.0% (7/237 patients) and 0.4% (1/237 patients), respectively. In the PH FDC SC arm, the incidence of treatment-emergent ADAs to pertuzumab and trastuzumab, and anti-rHuPH20 antibodies was 4.8% (11/231 patients), 0.9% (2/232 patients), and 0.9% (2/225 patients), respectively. Discrepancy in numbers of evaluable patients were due to sample collection issues, including samples not collected or collected incorrectly, and/or other sample operational logistics. Among patients who tested positive for ADAs to pertuzumab, neutralizing anti-pertuzumab antibodies were detected in one patient in the P+H IV arm and in one patient in the PH FDC SC arm. Among patients who tested positive for ADAs to trastuzumab, neutralizing anti-trastuzumab antibodies were detected in one patient treated in the PH FDC SC arm.

The exploratory analyses indicated that the occurrence of treatment-emergent ADAs to pertuzumab and trastuzumab, and/or anti-rHuPH20 antibodies (including neutralizing antibodies) did not appear to have any clinical consequences with respect to PK, efficacy (i.e. tpCR) or safety (i.e., IRR or ARR). However, due to the small number of ADA-positive patients, data are insufficient for robust assessments.

What is claimed is:

1. A method of treating HER2-positive early breast cancer patients comprising subcutaneously administering a therapeutically effective amount of a fixed dose combination (FDC) co-formulation of pertuzumab, trastuzumab, and hyaluronidase to said HER2-positive patients, said method comprising administering to said HER2-positive patients 8 cycles of neoadjuvant chemotherapy with concurrent administration of 4 cycles of said FDC during cycles 5 to 8, wherein:
   (a) said neoadjuvant chemotherapy comprises:
      (i) 4 cycles of 60 mg/m$^2$ doxorubicin and 600 mg/m$^2$ cyclophosphamide every 2 weeks followed by 80 mg/m$^2$ paclitaxel weekly for 12 weeks; or
      (ii) 4 cycles of 60 mg/m$^2$ doxorubicin and 600 mg/m$^2$ cyclophosphamide every 3 weeks followed by 4 cycles of docetaxel at 75 mg/m$^2$ for the first cycle and then 100 mg/m$^2$ for subsequent cycles if tolerated every 3 weeks;
   (b) said FDC is administered to said HER2-positive patients every 3 weeks for 4 cycles as a loading dose FDC comprising 1200 mg pertuzumab, 600 mg trastuzumab and 30,000 units of hyaluronidase, followed by maintenance dose FDC comprising 600 mg pertuzumab, 600 mg trastuzumab and 20,000 units of hyaluronidase; and
   (c) said therapeutically effective amount causes a pathological complete response rate of about 60% or more in said HER2-positive patients; and
   (d) said therapeutically effective amount results in ≤0.4% treatment-emergent neutralizing anti-pertuzumab antibodies in said HER2-positive patients.

2. The method of claim 1, wherein said neoadjuvant chemotherapy comprises 4 cycles of 60 mg/m$^2$ doxorubicin and 600 mg/m$^2$ cyclophosphamide every 2 weeks followed by 80 mg/m$^2$ paclitaxel weekly for 12 weeks.

3. The method of claim 2, wherein said therapeutically effective amount causes a pathological complete response rate of 66.7% in said HER2-positive patients.

4. The method of claim 1, wherein said neoadjuvant chemotherapy comprises 4 cycles of 60 mg/m$^2$ doxorubicin and 600 mg/m$^2$ cyclophosphamide every 3 weeks followed by 4 cycles of docetaxel at 75 mg/m$^2$ for the first cycle and then 100 mg/m$^2$ for subsequent cycles if tolerated every 3 weeks.

5. The method of claim 1, comprising administering maintenance dose FDC to said HER2-positive patients following surgery every 3 weeks for about 1 year (up to 18 cycles).

6. The method of claim 1, wherein said HER2-positive patients have hormone receptor-negative cancer.

7. The method of claim 6, wherein said therapeutically effective amount causes a pathological complete response rate of 70.8% in said HER2-positive patients.

8. The method of claim 1, wherein said HER2-positive patients have stage II-IIIA cancer.

9. The method of claim 1, wherein said HER2-positive patients have locally advanced, inflammatory, or early stage breast cancer (either greater than 2 cm in diameter or node positive).

10. The method of claim 1, wherein said therapeutically effective amount results in an incidence of hypersensitivity ≤1.2% in said HER2-positive patients.

* * * * *

UNITED STATES PATENT AND TRADEMARK OFFICE
CERTIFICATE OF CORRECTION

| | |
|---|---|
| PATENT NO. | : 12,252,549 B2 |
| APPLICATION NO. | : 17/304909 |
| DATED | : March 18, 2025 |
| INVENTOR(S) | : Tanja Badovinac-Crnjevic et al. |

Page 1 of 1

It is certified that error appears in the above-identified patent and that said Letters Patent is hereby corrected as shown below:

On the Title Page

Item [72], Lines 3-4, delete "Welwyn Garden (GB);" and insert -- Welwyn Garden City (GB); --

In the Claims

Column 103, Line 49, Claim 1 delete "hyaluronidase; and" and insert -- hyaluronidase; --

Column 104, Line 29, Claim 3 delete "affective amount" and insert -- effective amount --

Signed and Sealed this
Twenty-second Day of April, 2025

Coke Morgan Stewart
*Acting Director of the United States Patent and Trademark Office*

SEQUENCE LISTING

```
<160> NUMBER OF SEQ ID NOS: 22

<210> SEQ ID NO 1
<211> LENGTH: 195
<212> TYPE: PRT
<213> ORGANISM: Homo sapiens

<400> SEQUENCE: 1
```

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
                100                 105                 110

Gly Gly Leu Arg Glu Leu Gln Leu Arg Ser Leu Thr Glu Ile Leu Lys
            115                 120                 125

Gly Gly Val Leu Ile Gln Arg Asn Pro Gln Leu Cys Tyr Gln Asp Thr
        130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
                180                 185                 190

Leu Thr Arg
        195

<210> SEQ ID NO 2
<211> LENGTH: 124
<212> TYPE: PRT
<213> ORGANISM: Homo sapiens

<400> SEQUENCE: 2

Thr Val Cys Ala Gly Gly Cys Ala Arg Cys Lys Gly Pro Leu Pro Thr
1               5                   10                  15

Asp Cys Cys His Glu Gln Cys Ala Ala Gly Cys Thr Gly Pro Lys His
                20                  25                  30

Ser Asp Cys Leu Ala Cys Leu His Phe Asn His Ser Gly Ile Cys Glu
            35                  40                  45

Leu His Cys Pro Ala Leu Val Thr Tyr Asn Thr Asp Thr Phe Glu Ser
        50                  55                  60

Met Pro Asn Pro Glu Gly Arg Tyr Thr Phe Gly Ala Ser Cys Val Thr
65                  70                  75                  80

Ala Cys Pro Tyr Asn Tyr Leu Ser Thr Asp Val Gly Ser Cys Thr Leu
                85                  90                  95

Val Cys Pro Leu His Asn Gln Glu Val Thr Ala Glu Asp Gly Thr Gln
                100                 105                 110

Arg Cys Glu Lys Cys Ser Lys Pro Cys Ala Arg Val
            115                 120

<210> SEQ ID NO 3
<211> LENGTH: 169
<212> TYPE: PRT
<213> ORGANISM: Homo sapiens

<400> SEQUENCE: 3

Cys Tyr Gly Leu Gly Met Glu His Leu Arg Glu Val Arg Ala Val Thr
1               5                   10                  15

Ser Ala Asn Ile Gln Glu Phe Ala Gly Cys Lys Lys Ile Phe Gly Ser
            20                  25                  30

Leu Ala Phe Leu Pro Glu Ser Phe Asp Gly Asp Pro Ala Ser Asn Thr
        35                  40                  45

Ala Pro Leu Gln Pro Glu Gln Leu Gln Val Phe Glu Thr Leu Glu Glu
    50                  55                  60

Ile Thr Gly Tyr Leu Tyr Ile Ser Ala Trp Pro Asp Ser Leu Pro Asp
65                  70                  75                  80

Leu Ser Val Phe Gln Asn Leu Gln Val Ile Arg Gly Arg Ile Leu His
                85                  90                  95

Asn Gly Ala Tyr Ser Leu Thr Leu Gln Gly Leu Gly Ile Ser Trp Leu
            100                 105                 110

Gly Leu Arg Ser Leu Arg Glu Leu Gly Ser Gly Leu Ala Leu Ile His
        115                 120                 125

His Asn Thr His Leu Cys Phe Val His Thr Val Pro Trp Asp Gln Leu
    130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165

<210> SEQ ID NO 4
<211> LENGTH: 142
<212> TYPE: PRT
<213> ORGANISM: Homo sapiens

<400> SEQUENCE: 4

Cys His Gln Leu Cys Ala Arg Gly His Cys Trp Gly Pro Gly Pro Thr
1               5                   10                  15

Gln Cys Val Asn Cys Ser Gln Phe Leu Arg Gly Gln Glu Cys Val Glu
            20                  25                  30

Glu Cys Arg Val Leu Gln Gly Leu Pro Arg Glu Tyr Val Asn Ala Arg
        35                  40                  45

His Cys Leu Pro Cys His Pro Glu Cys Gln Pro Gln Asn Gly Ser Val
    50                  55                  60

Thr Cys Phe Gly Pro Glu Ala Asp Gln Cys Val Ala Cys Ala His Tyr
65                  70                  75                  80

Lys Asp Pro Pro Phe Cys Val Ala Arg Cys Pro Ser Gly Val Lys Pro
                85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
    130                 135                 140

<210> SEQ ID NO 5
<211> LENGTH: 107
<212> TYPE: PRT
<213> ORGANISM: Mus musculus

<400> SEQUENCE: 5

Asp Thr Val Met Thr Gln Ser His Lys Ile Met Ser Thr Ser Val Gly
1               5                   10                  15

```
Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 6
<211> LENGTH: 119
<212> TYPE: PRT
<213> ORGANISM: Mus musculus

<400> SEQUENCE: 6

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

Thr Phe Gly Gln Gly Thr Lys Val Glu Ile Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115
```

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 16
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30
```

```
Thr Met Asp Trp Val Arg Gln Ala Pro Gly Lys Gly Leu Glu Trp Val
     35                  40                  45
Ala Asp Val Asn Pro Asn Ser Gly Gly Ser Ile Tyr Asn Gln Arg Phe
 50                  55                  60
Lys Gly Arg Phe Thr Leu Ser Val Asp Arg Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asn Leu Gly Pro Ser Phe Tyr Phe Asp Tyr Trp Gly Gln Gly
             100                 105                 110
Thr Leu Val Thr Val Ser Ser Ala Ser Thr Lys Gly Pro Ser Val Phe
         115                 120                 125
Pro Leu Ala Pro Ser Ser Lys Ser Thr Ser Gly Gly Thr Ala Ala Leu
     130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                 165                 170                 175
Gln Ser Ser Gly Leu Tyr Ser Leu Ser Ser Val Val Thr Val Pro Ser
             180                 185                 190
Ser Ser Leu Gly Thr Gln Thr Tyr Ile Cys Asn Val Asn His Lys Pro
         195                 200                 205
Ser Asn Thr Lys Val Asp Lys Lys Val Glu Pro Lys Ser Cys Asp Lys
     210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                 245                 250                 255
Arg Thr Pro Glu Val Thr Cys Val Val Val Asp Val Ser His Glu Asp
             260                 265                 270
Pro Glu Val Lys Phe Asn Trp Tyr Val Asp Gly Val Glu Val His Asn
         275                 280                 285
Ala Lys Thr Lys Pro Arg Glu Glu Gln Tyr Asn Ser Thr Tyr Arg Val
     290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                 325                 330                 335
Thr Ile Ser Lys Ala Lys Gly Gln Pro Arg Glu Pro Gln Val Tyr Thr
             340                 345                 350
Leu Pro Pro Ser Arg Glu Glu Met Thr Lys Asn Gln Val Ser Leu Thr
         355                 360                 365
Cys Leu Val Lys Gly Phe Tyr Pro Ser Asp Ile Ala Val Glu Trp Glu
     370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                 405                 410                 415
Ser Arg Trp Gln Gln Gly Asn Val Phe Ser Cys Ser Val Met His Glu
             420                 425                 430
Ala Leu His Asn His Tyr Thr Gln Lys Ser Leu Ser Leu Ser Pro Gly
         435                 440                 445
Lys
```

```
<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Asp or Ser

<400> SEQUENCE: 17

Gly Phe Thr Phe Thr Asp Tyr Thr Met Xaa
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Val Asn Pro Asn Ser Gly Gly Ser Ile Tyr Asn Gln Arg Phe Lys
1               5                   10                  15

Gly

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Leu Gly Pro Ser Phe Tyr Phe Asp Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ala Ser Gln Asp Val Ser Ile Gly Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Tyr or Glu
```

```
<220> FEATURE:
<221> NAME/KEY: MOD_RES
<222> LOCATION: (7)..(7)
<223> OTHER INFORMATION: Thr or Ser

<400> SEQUENCE: 21

Ser Ala Ser Tyr Xaa Xaa Xaa
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Tyr Tyr Ile Tyr Pro Tyr Thr
1               5
```